US012741123B2

(12) United States Patent
Shevgoor et al.

(10) Patent No.: US 12,741,123 B2
(45) Date of Patent: Sep. 22, 2026

(54) SAFETY IV CATHETER WITH V-CLIP INTERLOCK AND NEEDLE TIP CAPTURE

(71) Applicant: Becton, Dickinson and Company, Franklin Lakes, NJ (US)

(72) Inventors: Siddarth K. Shevgoor, Laguna Beach, CA (US); Weston Harding, Lehi, UT (US); John Stokes, Pleasant View, UT (US); Jon Burkholz, Salt Lake City, UT (US); Stephen Bornhoft, Sandy, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 17/974,341

(22) Filed: Oct. 26, 2022

(65) Prior Publication Data

US 2023/0039751 A1 Feb. 9, 2023

Related U.S. Application Data

(63) Continuation of application No. 15/525,390, filed as application No. PCT/US2015/059748 on Nov. 9, 2015, now Pat. No. 11,511,052.

(Continued)

(51) Int. Cl.
*A61M 25/06* (2006.01)
*A61M 5/32* (2006.01)
(Continued)

(52) U.S. Cl.
CPC ...... *A61M 25/0618* (2013.01); *A61M 5/3243* (2013.01); *A61M 5/348* (2013.01);
(Continued)

(58) Field of Classification Search
CPC .......... A61M 25/0612; A61M 25/0618; A61M 25/0625; A61M 25/0631
See application file for complete search history.

(56) References Cited

U.S. PATENT DOCUMENTS 3,585,996 A 6/1971 Reynolds et al.
4,332,249 A 6/1982 Joslin
(Continued)

FOREIGN PATENT DOCUMENTS

AU 2006203663 B2 2/2008
AU 2006203664 2/2008
(Continued)

OTHER PUBLICATIONS

US 5755409 A, Aug. 7, 1029, Sigmund (withdrawn).
(Continued)

*Primary Examiner* — Emily L Schmidt
(74) *Attorney, Agent, or Firm* — Dickinson Wright, PLLC

(57) ABSTRACT

A catheter assembly (10) comprises a catheter (22), a needle (12) having a sharp distal tip, a catheter hub (14) housing the catheter (22), the catheter hub (14) having a collar (34) including a notch (36), a needle shield (20) connected to the catheter hub (14) when the needle (12) is in a first position, and a clip (40) disposed in the needle shield (20) that cooperates with the needle (12), wherein the clip (40) engages the catheter hub (14) in the first position of the needle (12), and the clip (40) disengages the catheter hub (14) via the notch (36) when the needle (12) is retracted to a second position to cover at least a portion of the needle (12). The clip (40) is mounted in the outer housing (38) of the needle shield (20) via a spade (66) having an outer wall (70) exposed to the outside of the needle shield (20), in order to reduce the overall width of the needle shield (20).

13 Claims, 81 Drawing Sheets

Related U.S. Application Data

(60) Provisional application No. 62/220,629, filed on Sep. 18, 2015, provisional application No. 62/077,760, filed on Nov. 10, 2014.

(51) Int. Cl.
*A61M 5/34* (2006.01)
*A61M 25/00* (2006.01)

(52) U.S. Cl.
CPC .... *A61M 25/0606* (2013.01); *A61M 25/0631* (2013.01); *A61M 5/3293* (2013.01); *A61M 25/0014* (2013.01)

(56) References Cited

U.S. PATENT DOCUMENTS

| | | | |
|---|---|---|---|
| 4,387,879 | A | 6/1983 | Tauschinski |
| 4,524,805 | A | 6/1985 | Hoffman |
| 4,622,964 | A | 11/1986 | Flynn |
| 4,762,516 | A | 8/1988 | Luther et al. |
| 4,809,679 | A | 3/1989 | Shimonaka et al. |
| 4,842,591 | A | 6/1989 | Luther |
| 4,850,961 | A | 7/1989 | Wanderer et al. |
| 4,871,356 | A | 10/1989 | Haindl et al. |
| 4,917,668 | A | 4/1990 | Haindl |
| 4,935,010 | A | 6/1990 | Cox et al. |
| 4,946,133 | A | 8/1990 | Johnson et al. |
| 4,948,092 | A | 8/1990 | Kasper et al. |
| 4,978,344 | A | 12/1990 | Dombrowski et al. |
| 5,000,740 | A | 3/1991 | Ducharme et al. |
| 5,032,116 | A | 7/1991 | Peterson et al. |
| 5,053,014 | A | 10/1991 | Van Heugten |
| 5,092,845 | A | 3/1992 | Chang |
| 5,108,380 | A | 4/1992 | Herlitze et al. |
| 5,156,596 | A | 10/1992 | Balbierz et al. |
| 5,215,525 | A | 6/1993 | Sturman |
| 5,215,528 | A | 6/1993 | Purdy et al. |
| 5,228,453 | A | 7/1993 | Sepetka |
| 5,290,246 | A | 3/1994 | Yamamoto et al. |
| 5,300,045 | A * | 4/1994 | Plassche, Jr. ..... A61M 25/0618 604/161 |
| 5,322,518 | A | 6/1994 | Schneider et al. |
| 5,328,482 | A | 7/1994 | Sircom et al. |
| 5,348,544 | A | 9/1994 | Sweeney et al. |
| 5,391,152 | A | 2/1995 | Patterson |
| 5,405,323 | A | 4/1995 | Rogers et al. |
| 5,417,569 | A | 5/1995 | Perisse |
| 5,419,766 | A | 5/1995 | Chang et al. |
| 5,423,766 | A | 6/1995 | Di Cesare |
| 5,458,658 | A | 10/1995 | Sircom |
| 5,501,675 | A | 3/1996 | Erskine |
| 5,533,974 | A | 7/1996 | Gaba |
| 5,538,508 | A | 7/1996 | Steyn |
| 5,558,651 | A | 9/1996 | Crawford et al. |
| 5,575,777 | A | 11/1996 | Cover et al. |
| 5,584,809 | A | 12/1996 | Gaba |
| 5,596,996 | A | 1/1997 | Johanson |
| 5,662,610 | A * | 9/1997 | Sircom ............... A61M 5/3273 604/110 |
| 5,697,907 | A | 12/1997 | Gaba |
| 5,718,688 | A | 2/1998 | Wozencroft |
| 5,749,857 | A | 5/1998 | Cuppy |
| 5,772,636 | A | 6/1998 | Brimhall et al. |
| 5,817,069 | A | 10/1998 | Arnett |
| 5,851,196 | A | 12/1998 | Arnett |
| 5,853,393 | A | 12/1998 | Bogert |
| 5,858,002 | A | 1/1999 | Jesch |
| 5,879,337 | A | 3/1999 | Kuracina et al. |
| 5,911,710 | A | 6/1999 | Berry et al. |
| 5,951,515 | A | 9/1999 | Osterlind |
| 5,954,698 | A | 9/1999 | Pike |
| 5,967,490 | A | 10/1999 | Pike |
| 6,001,080 | A | 12/1999 | Kuracina et al. |
| 6,042,876 | A | 3/2000 | Deem |
| 6,117,108 | A | 9/2000 | Woehr et al. |
| 6,213,978 | B1 | 4/2001 | Voyten |
| 6,221,047 | B1 | 4/2001 | Greene et al. |
| 6,224,569 | B1 | 5/2001 | Brimhall et al. |
| 6,379,333 | B1 | 4/2002 | Brimhall et al. |
| D459,802 | S | 7/2002 | Cindrich |
| 6,425,884 | B1 | 7/2002 | Wemmert et al. |
| 6,443,929 | B1 | 9/2002 | Kuracina et al. |
| 6,506,181 | B2 | 1/2003 | Meng et al. |
| 6,595,981 | B2 | 7/2003 | Huet |
| 6,616,630 | B1 | 9/2003 | Woehr et al. |
| 6,629,959 | B2 | 10/2003 | Kuracina et al. |
| 6,652,486 | B2 | 11/2003 | Bialecki et al. |
| 6,709,419 | B2 | 3/2004 | Woehr |
| D491,266 | S | 6/2004 | Cindrich et al. |
| 6,749,588 | B1 * | 6/2004 | Howell ............ A61M 25/0625 604/110 |
| 6,860,871 | B2 | 3/2005 | Kuracina et al. |
| 6,883,778 | B1 | 4/2005 | Newton et al. |
| 6,972,002 | B2 | 12/2005 | Thorne |
| RE38,996 | E | 2/2006 | Crawford et al. |
| 7,226,434 | B2 | 6/2007 | Carlyon et al. |
| 7,374,554 | B2 | 5/2008 | Menzi et al. |
| 7,500,965 | B2 | 3/2009 | Menzi et al. |
| 7,530,965 | B2 | 5/2009 | Villa et al. |
| 7,534,231 | B2 | 5/2009 | Kuracina et al. |
| 7,597,681 | B2 | 10/2009 | Sutton et al. |
| 7,632,245 | B1 | 12/2009 | Cowan et al. |
| 7,651,476 | B2 | 1/2010 | Kohler |
| 7,722,569 | B2 | 5/2010 | Soderholm et al. |
| 7,731,687 | B2 | 6/2010 | Menzi et al. |
| 7,736,332 | B2 | 6/2010 | Carlyon et al. |
| 7,736,339 | B2 | 6/2010 | Woehr et al. |
| 7,927,314 | B2 | 4/2011 | Kuracina et al. |
| 7,988,664 | B2 | 8/2011 | Fiser et al. |
| 8,235,945 | B2 | 8/2012 | Baid |
| 8,308,691 | B2 | 11/2012 | Woehr et al. |
| 8,328,762 | B2 | 12/2012 | Woehr et al. |
| 8,333,735 | B2 | 12/2012 | Woehr et al. |
| 8,337,463 | B2 | 12/2012 | Woehr et al. |
| 8,348,893 | B2 | 1/2013 | Carlyon |
| 8,357,119 | B2 | 1/2013 | Stout et al. |
| 8,361,020 | B2 | 1/2013 | Stout |
| 8,361,038 | B2 | 1/2013 | McKinnon et al. |
| 8,382,718 | B2 | 2/2013 | Woehr |
| 8,388,583 | B2 | 3/2013 | Stout et al. |
| 8,414,539 | B1 | 4/2013 | Kuracina et al. |
| 8,419,688 | B2 | 4/2013 | Woehr et al. |
| 8,444,605 | B2 | 5/2013 | Kuracina et al. |
| 8,460,247 | B2 | 6/2013 | Woehr et al. |
| 8,469,928 | B2 | 6/2013 | Stout et al. |
| 8,496,623 | B2 | 7/2013 | Burkholz |
| 8,523,828 | B2 | 9/2013 | Callahan |
| 8,540,728 | B2 | 9/2013 | Woehr et al. |
| 8,545,454 | B2 | 10/2013 | Kuracina et al. |
| 8,591,467 | B2 | 11/2013 | Walker et al. |
| 8,591,468 | B2 | 11/2013 | Woehr et al. |
| 8,597,249 | B2 | 12/2013 | Woehr et al. |
| 8,764,711 | B2 | 7/2014 | Kuracina et al. |
| 8,827,965 | B2 | 9/2014 | Woe et al. |
| 8,926,564 | B2 | 1/2015 | King et al. |
| 8,951,230 | B2 | 2/2015 | Tanabe et al. |
| 9,056,188 | B2 | 6/2015 | Hager et al. |
| 9,089,671 | B2 | 7/2015 | Stout et al. |
| 9,114,241 | B2 | 8/2015 | Stout et al. |
| 9,149,625 | B2 | 10/2015 | Woehr et al. |
| 9,149,626 | B2 | 10/2015 | Woehr et al. |
| 9,278,180 | B2 | 3/2016 | Wong |
| 9,370,641 | B2 | 6/2016 | Woehr et al. |
| 9,408,632 | B2 | 8/2016 | Erskine |
| 9,592,152 | B2 | 3/2017 | Griffis et al. |
| 9,717,886 | B2 | 8/2017 | Kuehn et al. |
| 10,729,890 | B2 | 8/2020 | Harding et al. |
| 2001/0053895 | A1 | 12/2001 | Vaillancourt |
| 2002/0128604 | A1 | 9/2002 | Nakajima |
| 2002/0169418 | A1 | 11/2002 | Menzi et al. |
| 2003/0057392 | A1 | 3/2003 | Ito |
| 2003/0060771 | A1 | 3/2003 | Bialecki et al. |
| 2003/0060774 | A1 | 3/2003 | Woehr et al. |

(56) References Cited

U.S. PATENT DOCUMENTS

| | | | |
|---|---|---|---|
| 2003/0136932 A1 | 7/2003 | Doyle | |
| 2003/0195471 A1 | 10/2003 | Woehr et al. | |
| 2004/0116856 A1 | 6/2004 | Woehr et al. | |
| 2004/0204681 A1 | 10/2004 | Thoresen et al. | |
| 2004/0204689 A1 | 10/2004 | Lynn | |
| 2004/0225260 A1 | 11/2004 | Villa et al. | |
| 2005/0010176 A1 | 1/2005 | Dikeman et al. | |
| 2005/0043684 A1 | 2/2005 | Basta et al. | |
| 2005/0075609 A1 | 4/2005 | Latona | |
| 2005/0107740 A1 | 5/2005 | Jensen et al. | |
| 2005/0113755 A1 | 5/2005 | Greene et al. | |
| 2006/0074384 A1 | 4/2006 | Kohler | |
| 2006/0155245 A1 | 7/2006 | Woehr | |
| 2006/0178635 A1 | 8/2006 | Callaway | |
| 2006/0200080 A1 | 9/2006 | Abulhaj | |
| 2006/0264828 A1 | 11/2006 | Woehr et al. | |
| 2007/0038186 A1 | 2/2007 | Sutton et al. | |
| 2007/0083162 A1 | 4/2007 | O'Reagan et al. | |
| 2007/0129689 A1 | 6/2007 | Woehr et al. | |
| 2007/0176414 A1 | 8/2007 | McBee et al. | |
| 2007/0270754 A1 | 11/2007 | Soderholm et al. | |
| 2008/0065015 A1 | 3/2008 | Fisher et al. | |
| 2008/0097343 A1 | 4/2008 | Woehr | |
| 2008/0140004 A1 | 6/2008 | Thorne et al. | |
| 2008/0140011 A1 | 6/2008 | Hager et al. | |
| 2008/0147009 A1 | 6/2008 | Nilsson et al. | |
| 2008/0208132 A1 | 8/2008 | Funamura et al. | |
| 2008/0243086 A1 | 10/2008 | Hager et al. | |
| 2009/0088696 A1 | 4/2009 | Harding et al. | |
| 2009/0137958 A1 | 5/2009 | Erskine | |
| 2009/0163861 A1 | 6/2009 | Carlyon | |
| 2009/0182280 A1 | 7/2009 | Glowacki et al. | |
| 2009/0281499 A1* | 11/2009 | Harding | A61M 25/0618 604/164.08 |
| 2009/0312711 A1 | 12/2009 | Brimhall | |
| 2010/0137803 A1 | 6/2010 | Funamura et al. | |
| 2010/0137815 A1 | 6/2010 | Kuracina et al. | |
| 2010/0191189 A1 | 7/2010 | Harding et al. | |
| 2010/0204648 A1 | 8/2010 | Stout et al. | |
| 2010/0204660 A1 | 8/2010 | McKinnon et al. | |
| 2010/0217208 A1 | 8/2010 | Snow | |
| 2010/0222746 A1 | 9/2010 | Burkholz | |
| 2011/0046570 A1 | 2/2011 | Stout et al. | |
| 2011/0054402 A1 | 3/2011 | Tanabe et al. | |
| 2011/0054403 A1 | 3/2011 | Tanabe et al. | |
| 2011/0060286 A1 | 3/2011 | Tanabe et al. | |
| 2011/0160662 A1 | 6/2011 | Stout et al. | |
| 2011/0160671 A1 | 6/2011 | Tanabe et al. | |
| 2011/0213307 A1 | 9/2011 | Kawai et al. | |
| 2011/0288482 A1 | 11/2011 | Farrell et al. | |
| 2011/0301551 A1 | 12/2011 | Koehler et al. | |
| 2012/0065612 A1 | 3/2012 | Stout et al. | |
| 2012/0078200 A1 | 3/2012 | Woehr et al. | |
| 2012/0123354 A1 | 5/2012 | Woehr | |
| 2012/0136311 A1 | 5/2012 | Knutsson et al. | |
| 2012/0220957 A1 | 8/2012 | Kuracina et al. | |
| 2012/0238966 A1 | 9/2012 | Kuracina et al. | |
| 2012/0277679 A1 | 11/2012 | Steube | |
| 2013/0030370 A1 | 1/2013 | Walker et al. | |
| 2013/0090607 A1 | 4/2013 | McKinnon et al. | |
| 2013/0090609 A1 | 4/2013 | Sonderegger et al. | |
| 2013/0096504 A1 | 4/2013 | Walker et al. | |
| 2013/0165868 A1 | 6/2013 | Isaacson et al. | |
| 2013/0178807 A1 | 7/2013 | Baid | |
| 2013/0184645 A1 | 7/2013 | Baid | |
| 2013/0226141 A1 | 8/2013 | King et al. | |
| 2013/0245567 A1 | 9/2013 | Tremblay | |
| 2013/0253443 A1 | 9/2013 | Woehr et al. | |
| 2013/0310751 A1 | 11/2013 | Davis et al. | |
| 2013/0324930 A1 | 12/2013 | Fuchs et al. | |
| 2014/0012203 A1 | 1/2014 | Woehr et al. | |
| 2014/0018738 A1 | 1/2014 | Steube | |
| 2014/0058329 A1 | 2/2014 | Walker et al. | |
| 2014/0276434 A1 | 9/2014 | Woehr et al. | |
| 2014/0303561 A1 | 10/2014 | Li | |
| 2014/0364809 A1 | 12/2014 | Isaacson et al. | |
| 2015/0151088 A1 | 6/2015 | Lim et al. | |
| 2015/0238733 A1 | 8/2015 | bin Abdulla | |
| 2016/0015941 A1 | 1/2016 | Tanabe et al. | |
| 2016/0106959 A1 | 4/2016 | Woehr | |
| 2016/0158503 A1 | 6/2016 | Woehr | |
| 2016/0158526 A1 | 6/2016 | Woehr | |
| 2017/0348518 A1 | 12/2017 | Ma et al. | |

FOREIGN PATENT DOCUMENTS

| | | | |
|---|---|---|---|
| CA | 2133053 | A1 | 3/1995 |
| CN | 1758929 | A | 4/2006 |
| CN | 1871043 | A | 11/2006 |
| CN | 101466431 | A | 6/2009 |
| CN | 101573153 | | 11/2009 |
| CN | 101573154 | A | 11/2009 |
| CN | 101573155 | A | 11/2009 |
| CN | 101791447 | A | 8/2010 |
| CN | 202005932 | U | 10/2011 |
| CN | 202682467 | U | 1/2013 |
| CN | 202844312 | U | 4/2013 |
| CN | 103124578 | A | 5/2013 |
| CN | 203196075 | U | 9/2013 |
| CN | 203493994 | U | 3/2014 |
| CN | 106470607 | A | 3/2017 |
| EP | 0352928 | A1 | 1/1990 |
| EP | 0570530 | B1 | 8/1999 |
| EP | 1 892 003 | A1 | 2/2008 |
| EP | 1558311 | A1 | 8/2008 |
| EP | 2204204 | A1 | 7/2010 |
| EP | 2228093 | A1 | 9/2010 |
| EP | 1240916 | B2 | 4/2011 |
| EP | 2343095 | A1 | 7/2011 |
| EP | 2489393 | A1 | 8/2012 |
| EP | 2566543 | A1 | 3/2013 |
| EP | 2803376 | A1 | 11/2014 |
| JP | H1057497 | A | 3/1998 |
| JP | 2001514943 | A | 9/2001 |
| JP | 2002126080 | A | 5/2002 |
| JP | 2002263197 | A | 9/2002 |
| JP | 2008173206 | A | 7/2008 |
| JP | 2010099534 | A | 5/2010 |
| JP | 2011115630 | A | 6/2011 |
| JP | 3170612 | U | 8/2011 |
| JP | 2012-517327 | A | 8/2012 |
| JP | 2012517326 | A | 8/2012 |
| JP | 2012519057 | A | 8/2012 |
| JP | 2013527005 | A | 6/2013 |
| JP | 2013192868 | A | 9/2013 |
| JP | 2017533770 | A | 11/2017 |
| SG | 173383 | | 8/2011 |
| WO | 1993005840 | A2 | 4/1993 |
| WO | 1995022364 | A1 | 8/1995 |
| WO | 9924092 | | 5/1999 |
| WO | 2001012249 | A1 | 2/2001 |
| WO | 193940 | A2 | 12/2001 |
| WO | 0195958 | A1 | 12/2001 |
| WO | 2003011381 | | 2/2003 |
| WO | 2004004819 | A1 | 1/2004 |
| WO | 2005042073 | A1 | 5/2005 |
| WO | 2007/139740 | A2 | 12/2007 |
| WO | 2008064332 | A2 | 5/2008 |
| WO | 2009142878 | A1 | 11/2009 |
| WO | 2009154824 | A1 | 12/2009 |
| WO | 2010/093792 | A1 | 2/2010 |
| WO | 2011/162886 | A2 | 12/2011 |
| WO | 2012/020633 | A1 | 2/2012 |
| WO | 2012/139034 | A1 | 10/2012 |
| WO | 2013014639 | A1 | 1/2013 |
| WO | 2013016373 | A1 | 1/2013 |
| WO | 2013051242 | A1 | 4/2013 |
| WO | 2013052666 | A1 | 4/2013 |
| WO | 2013137348 | A1 | 9/2013 |
| WO | 2013162461 | A1 | 10/2013 |
| WO | 2014054166 | A1 | 4/2014 |
| WO | 2014126865 | A1 | 8/2014 |
| WO | 2014197656 | A1 | 12/2014 |
| WO | 2015024904 | A1 | 2/2015 |

(56) References Cited

FOREIGN PATENT DOCUMENTS

| | | | |
|---|---|---|---|
| WO | 2015161296 | A1 | 10/2015 |
| WO | 2016077234 | A1 | 5/2016 |
| WO | 2014162377 | A1 | 2/2017 |

OTHER PUBLICATIONS

Singapore Office Action dated Jan. 29, 2020 in Singapore Patent Application No. 11201708370P.

Japanese Office Action dated Jan. 28, 2020 in Japanese Patent Application No. 2017-554341.

Singapore Office Action dated Nov. 12, 2019 in Singapore Patent Application No. 11201708371S.

Brazilian Office Action dated Feb. 4, 2020 in Brazilian Patent Application No. 112015030658-6.

MEDIKIT Co., Ltd., Dual Protection Safety I.V. Catheter—Supercath 5: A New Generation of Safety I.V. Catheter, Medikit, Manufacturer TOGO Medikit Co., Ltd., IV IVBB080001-B61G2S, Approximately 2008 (3 Pages Total).

* cited by examiner 40
64
62
60
68
76
70
72
66
74

64
60
62
78
76
68
80
82
70
66
72
84
74

40
64
60
62
68
66
76
84
78
82
86

64
40
60
68
84
66
82

40
64
62
84
82
66

64
40
62
60
80
78
76
68
86
72
70
74

64
40
60
62
80
78
68
76
70
72
86
74
84

40
66
76
60
64
84
62
82
86

40
62
86
84
82
64
60
76
66

710
732
736
712
716
734
728
724
714
726
718
720
736

736
734
732
712
722
728
730
716
714
718
724
720
726

SAFETY IV CATHETER WITH V-CLIP INTERLOCK AND NEEDLE TIP CAPTURE

RELATED APPLICATIONS

This application is a continuation of U.S. Nonprovisional application Ser. No. 15/525,390, filed May 9, 2017, which is a national stage application, filed under 35 U.S.C. § 371, of International Application No. PCT/US2015/059748, filed Nov. 9, 2015, which claims the benefit under 35 U.S.C. § 119(e) of U.S. Provisional Patent Application Ser. No. 62/077,760, filed on Nov. 10, 2014, and U.S. Provisional Patent Application Ser. No. 62/220,629, filed on Sep. 18, 2015. Each of the foregoing applications is hereby incorporated by reference in its entirety.

FIELD

Various exemplary embodiments of the invention relate to catheters.

BACKGROUND

Catheter assemblies are used to place a catheter into the vascular system of a patient. Once in place, catheters such as intravenous catheters may be used to infuse fluids including normal saline, medicinal compounds, and/or nutritional compositions into a patient in need of such treatment. Catheters additionally enable the removal of fluids from the circulatory system and monitoring of conditions within the vascular system of the patient.

SUMMARY OF THE INVENTION

It is an aspect of the present invention to provide a catheter assembly in which an improved clip and needle shield are used for needle protection. The improved arrangement is more compact, provides increased needle protection, and reduces the size and complexity of the catheter assembly. The improved clip provides a more narrow design, increased strength and flexibility, and a variety of mounting configurations to secure the clip to the needle shield. The addition of a release notch in a collar of a catheter hub and disengagement of the clip via the notch allows the needle shield to be more compact than in the prior art. In the prior art, without the notch, the clip has to travel a longer distance to disengage the catheter hub. In addition, the width of the needle shield is reduced by an improved attachment interface between the clip and the needle shield. Specifically, a spade attaches the clip to the needle shield with an outer surface of the spade exposed to an outside of the needle shield.

The foregoing and/or other aspects of the present invention can be achieved by providing a catheter assembly comprising a catheter, a needle having a sharp distal tip disposed in the catheter, a catheter hub housing the catheter and the needle, the catheter hub having a notch, a needle shield connected to the catheter hub when the needle is in a first position, and a clip disposed in the needle shield that cooperates with the needle, wherein the clip engages the collar in the first position of the needle, the clip disengages the collar via the notch when the needle is retracted to a second position to enclose or cover at least a portion of the needle.

The foregoing and/or other aspects of the present invention can be achieved by also providing a catheter assembly comprising a catheter, a needle having a sharp distal tip disposed in the catheter, a catheter hub housing the catheter and the needle, a needle shield configured to be connected to the catheter hub, and a clip disposed in the needle shield that cooperates with the needle, the clip including a spade that attaches the clip to the needle shield, wherein an outer surface of the spade is exposed to an outside of the catheter assembly.

BRIEF DESCRIPTION OF THE DRAWINGS

The above aspects and features of the present invention will be more apparent from the description for the exemplary embodiments of the present invention taken with reference to the accompanying drawings, in which:

FIG. 119 illustrates the operation of a second embodiment of a catheter hub valve actuator in a free state;

FIG. 120 illustrates the operation of the second embodiment of the catheter hub valve actuator in the compressed state;

FIG. 121 illustrates another embodiment of the catheter hub valve actuator;

FIG. 122 illustrates an exemplary blood flashback feature of the catheter assembly;

FIG. 123 illustrates the needle of the blood flashback feature of the catheter assembly of FIG. 122;

FIG. 124 illustrates a second exemplary blood flashback feature of the catheter assembly;

FIG. 125 illustrates the second exemplary blood flashback feature of the catheter assembly of FIG. 124 with blood flashback in two places;

FIG. 126 illustrates a third exemplary blood flashback features of the catheter assembly with blood flashback in three places;

FIG. 127 illustrates a right side view of the exemplary embodiment of the actuator of FIG. 121;

FIG. 128 illustrates a cross sectional view of the actuator of FIG. 127 in a catheter hub assembly;

FIG. 129 illustrates the cross sectional view of the catheter hub assembly of FIG. 128 when penetrating a septum;

FIG. 130 illustrates a left perspective cross sectional view of the catheter hub assembly of FIG. 128 when penetrating a septum;

Figure 131:
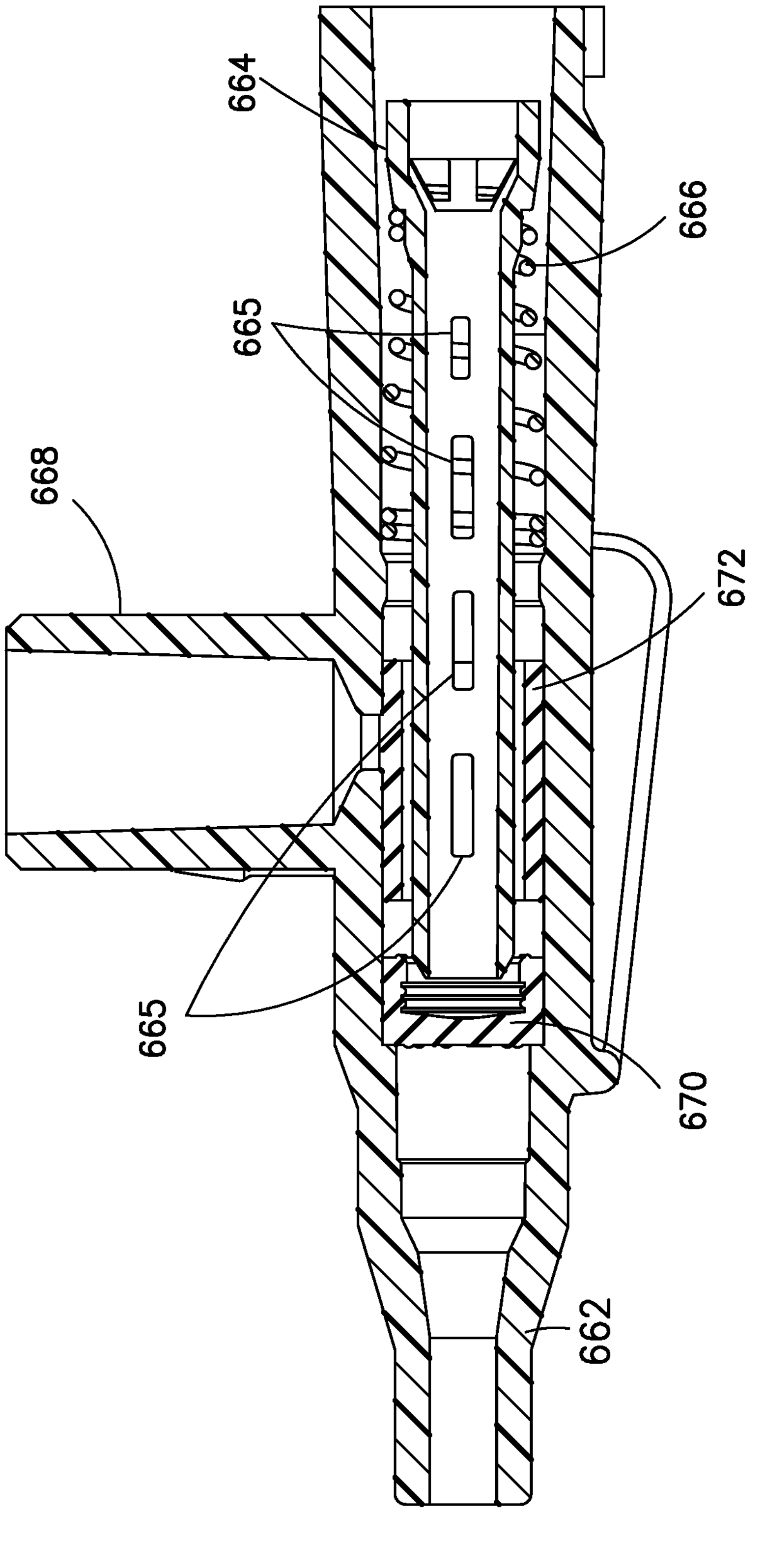
Figure 132:
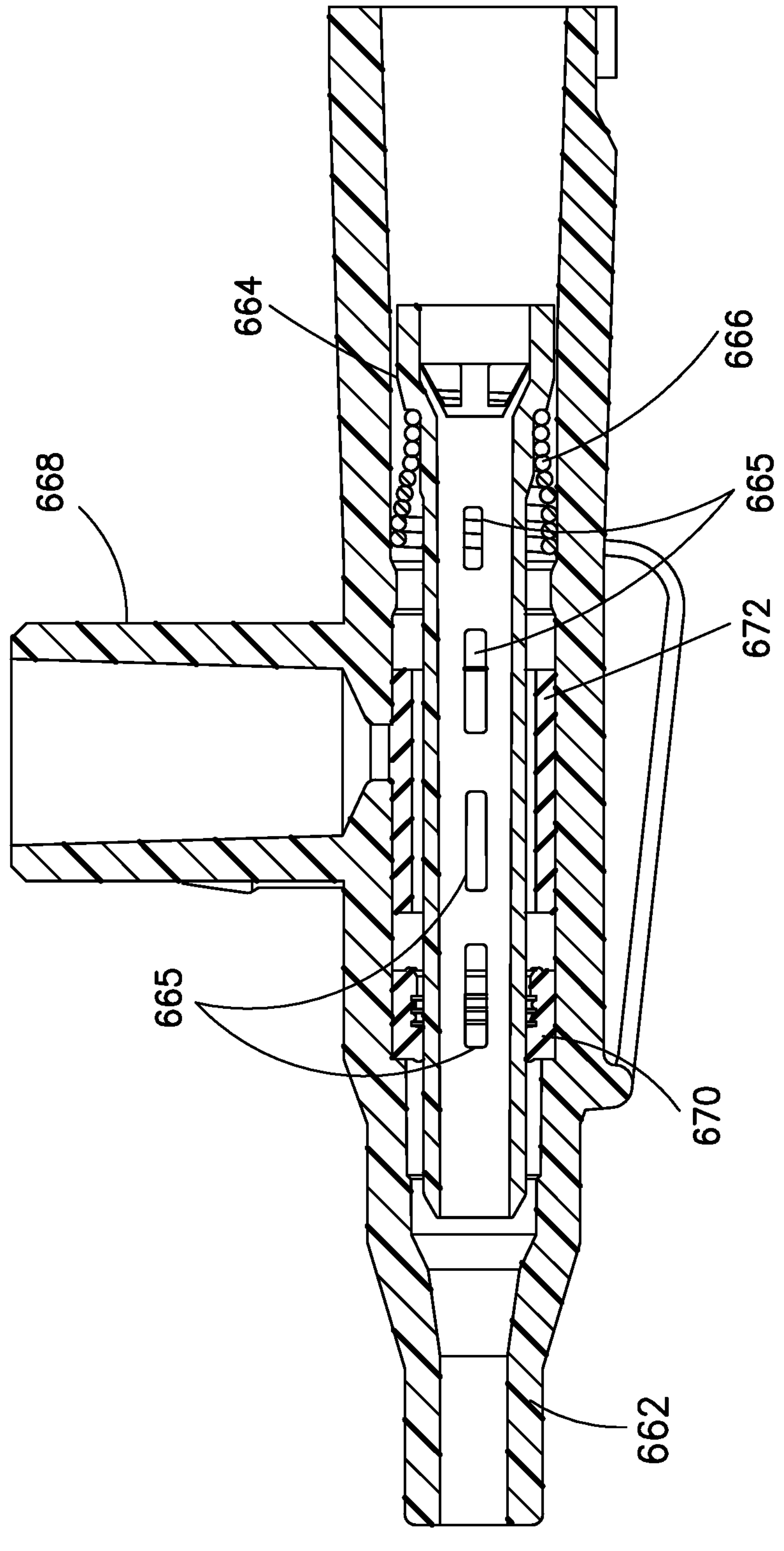
Figure 133:
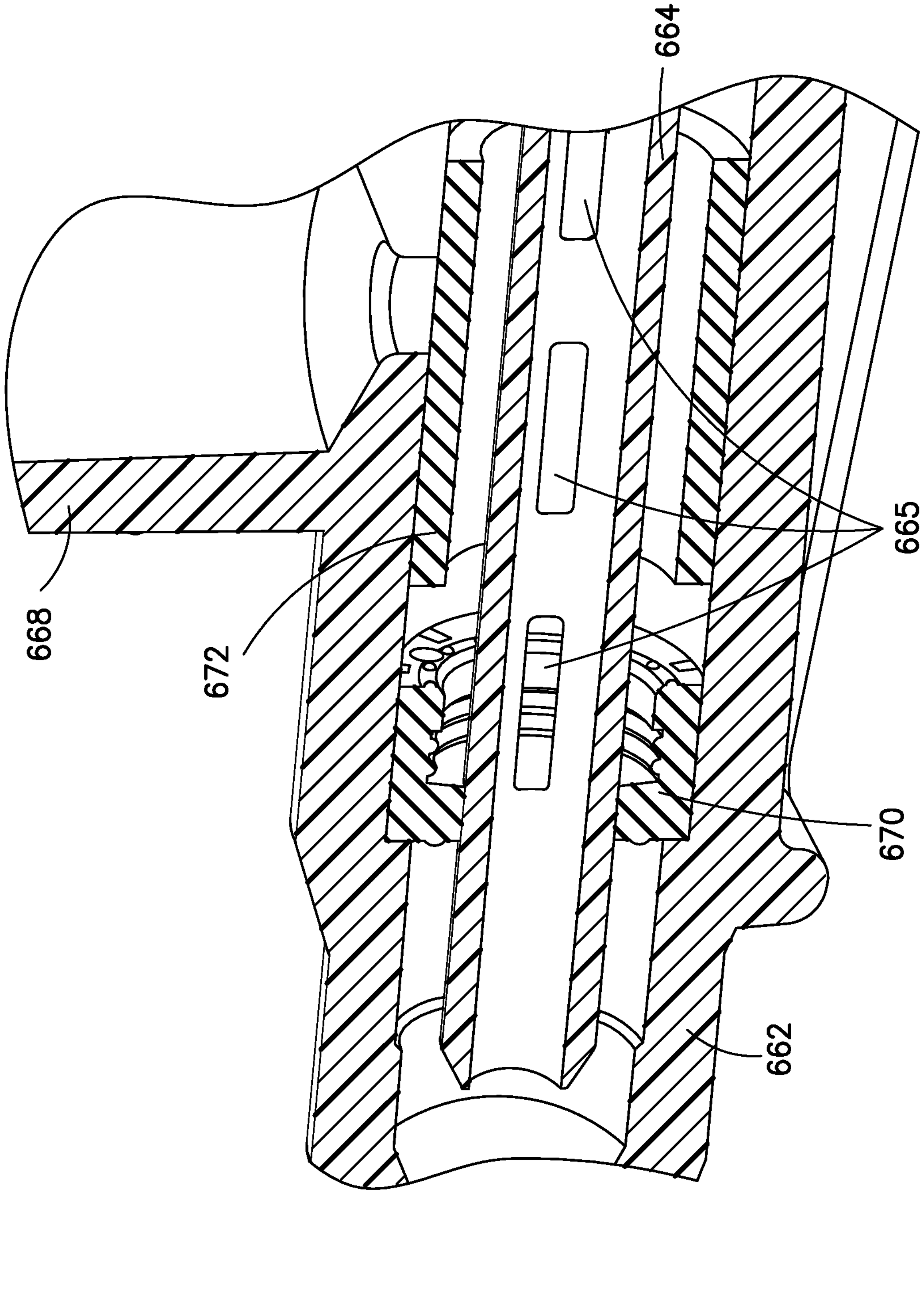

FIG. 131 illustrates a cross sectional view of another exemplary embodiment of a catheter hub assembly;

FIG. 132 illustrates the cross sectional view of the catheter hub assembly of FIG. 131 when penetrating a septum; and FIG. 133 illustrates a left perspective cross sectional view of the catheter hub assembly of FIG. 131 when penetrating a septum.

DETAILED DESCRIPTION OF EXEMPLARY EMBODIMENTS

The catheter assembly disclosed herein is an improvement over that disclosed in commonly owned U.S. Patent Application Publication No. 2014/0364809, which is incorporated herein by reference.

FIGS. 1-12 illustrate a catheter assembly 10 includes a hollow metal introducer needle 12, a catheter hub 14, a needle hub 16, and a needle shield 20. The needle 12 has a sharpened and beveled distal end and initially extends through the needle shield 20 and the catheter hub 14. A flexible catheter tube 22 extends from the distal end of the catheter hub 14, with the introducer needle 12 passing through the catheter tube 22. Initially, the needle 12 is inserted into a patient's vein. The catheter tube 22 is carried by the needle 12 into the vein. After the catheter tube 22 is inserted, the needle 12 is removed from the patient's vein and the catheter hub 14. The needle shield 20 encloses or covers the tip of the needle 12 and provides protection from being stuck by the needle 12 during and after the needle's retraction from the catheter hub 14. The needle shield 20 can be used with a variety of different catheters.

As illustrated in FIGS. 12-20, the catheter assembly includes the catheter hub 14 and the flexible catheter tube 22 extending from the catheter hub 14. A metal wedge 24 is positioned in the catheter hub 14 to retain the catheter tube 22. A resilient septum 26 is positioned to control fluid flow through the catheter hub 14. An actuator 28 is moveably positioned in the catheter hub 14 to engage the septum 26. A biasing member 30 engages the actuator 28 to bias the actuator 28 in the proximal direction.

The resilient septum 26 has one or more pre-formed slits which are normally closed to selectively prevent unwanted fluid flow through the septum 26. For example, the septum 26 can have three slits forming three triangular flaps that open when engaged by the actuator 28. The septum 26 is made from an elastic material, for example silicone rubber, that provides the resilient closing force for the slits. Other septum 26 configurations may be used as would be understood by one of ordinary skill in the art.

The actuator 28 and the biasing member 30, for example a metal or plastic compression spring, are positioned in the catheter hub 14. The actuator 28 engages the septum 26 to open the slits and permit fluid flow through the catheter hub 14. The biasing member 30 is capable of returning the actuator 28 to a position that allows the slits to close, preventing fluid flow through the catheter hub 14.

As best shown in the exemplary embodiment of FIGS. 21-29, the catheter hub 14 includes a proximal end having external Luer thread 32 and a notched collar 34. The collar 34 extends around at least a portion of the catheter hub 14 and is preferably disposed at a proximal end of the catheter hub 14. The collar 34 has a break, opening or notch 36 separating first and second ends of the collar 34.

A portion of the collar 34 includes an outer diameter that is greater than a portion of an outer diameter of the catheter hub 14 adjacent to the collar 34. Specifically, a portion of the outer diameter of the collar 34 is elevated with respect to the adjacent outer diameter surface of the catheter hub 14. Additionally, the opening 36 of the collar 34 has an outer diameter substantially equal to or greater than a portion of an outer diameter of the catheter hub 14 adjacent to the collar 34.

In an exemplary embodiment, the needle shield 20 includes an outer housing 38, a resilient clip 40, and a washer 42. The outer housing 38 includes an aperture having a distal opening 44 and a proximal opening 46 to receive the needle 12. The outer housing 38 connects to the catheter hub 14 and surrounds the clip 40 and the washer 42. As best shown in FIGS. 30-39, the distal end of the outer housing 38 includes a nose 48, a top flange 50, and a base 52. When the needle shield 20 is connected to the catheter hub 14, the nose 48 extends into the interior of the catheter hub 14.

In an exemplary embodiment, the nose 48 is sized to be slightly smaller than the interior of the catheter hub 14 so as to fit with a loose tolerance. The top flange 50 is spaced from the base 52 by a pair of side recesses that receive the Luer threads 32 and prevent rotation of the catheter hub 14 with respect to the needle shield 20 when assembled. The base 52 includes a projection 54 having a curved top surface and curved cut-out portion 56. The projection 54 is sized to fit in the opening 36 of the collar 34 and the cut-out portion 56 is sized to allow the collar 34 to pass therethrough.

According to an exemplary embodiment illustrated in FIGS. 40-48, the clip 40 is a substantially V-shaped resilient clip 40 having a first leg 60 and a second leg 62 connected by an angled or curved V section 64. The first leg 60 includes a substantially U-shaped spade 66 having an angled lead-in portion 68. The spade 66 includes an outer wall 70 and an inner wall 72 connected by a bottom 74. A pair of barbs 76 extends outwardly from the inner wall 72 of the spade 66. A first flag 78 extends from the second leg 62 toward the first leg 60 and a second flag 80 extends from the first leg 60 toward the second leg 62. A foot 82 extends outwardly from the first flag 78 away from the first and second legs 60, 62, and a latch 84 extends upwardly from the foot 84 and is positioned between the first and second legs 60, 62. Specifically, the latch 84 is disposed between a plane representing the first leg 60 and a plane representing the second let 62. Such a configuration is desired to create a more compact clip 40. An optional stiffener 86 can extend downwardly from the foot 82.

FIGS. 49-75 illustrate alternate embodiments of the clip 710 that have similar features to the preferred embodiment of clip 40 in FIGS. 40-48 as described above. The details of the alternate embodiments of the clip 710, specifically the features that distinguish from the clip 40 in FIGS. 40-48, are described below. For brevity, the explanation of the similar features of the clip in FIGS. 40-75 is not repeated but rather understood by one skilled in the art base on the prior description herein. The features of the exemplary embodiments of FIGS. 49-75 may be combined with features of the other exemplary embodiments disclosed herein as appropriate.

Figure 1:
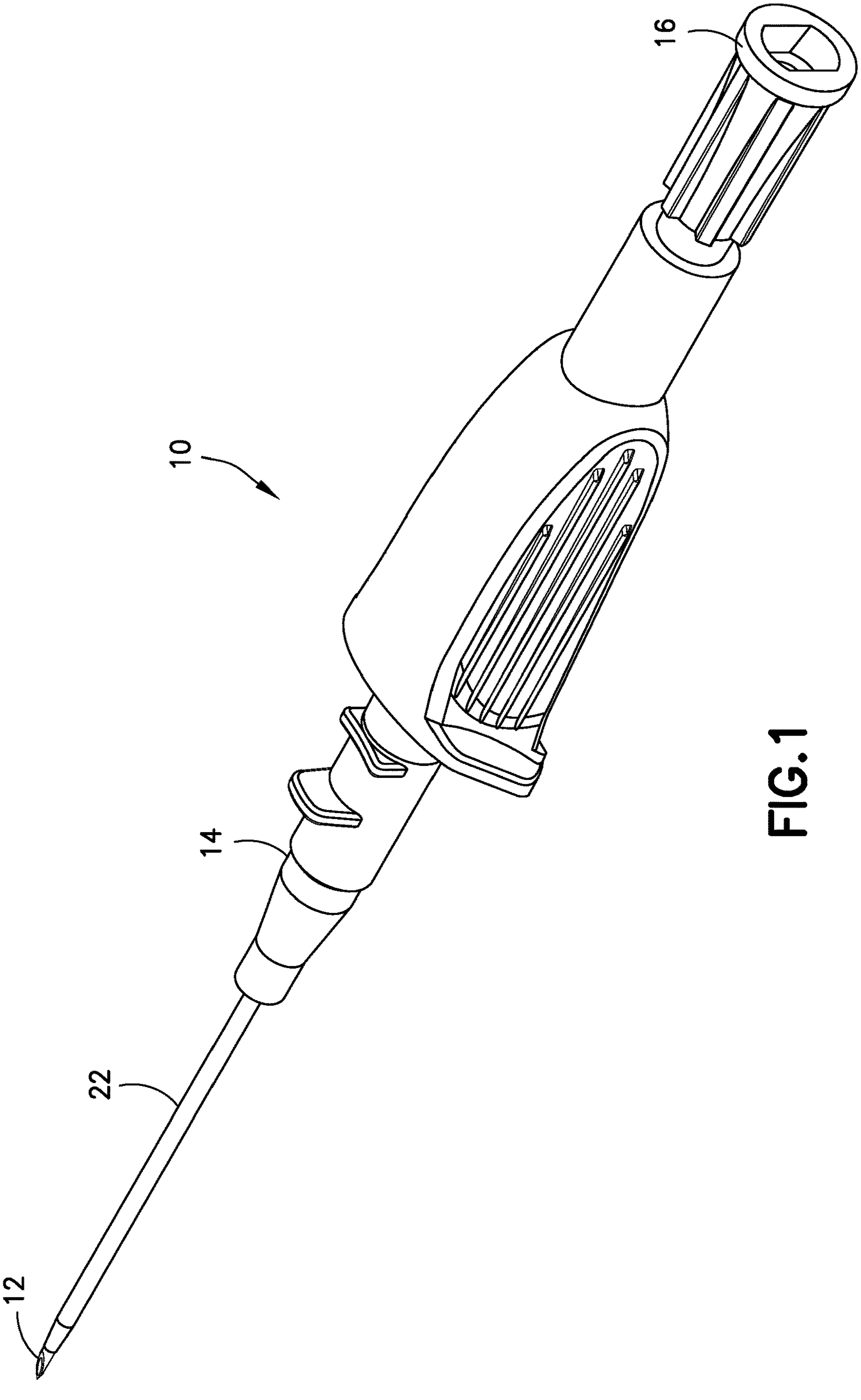
FIG. 1 illustrates a top left perspective view of a catheter assembly in accordance with an embodiment of the present invention.
Figure 2:
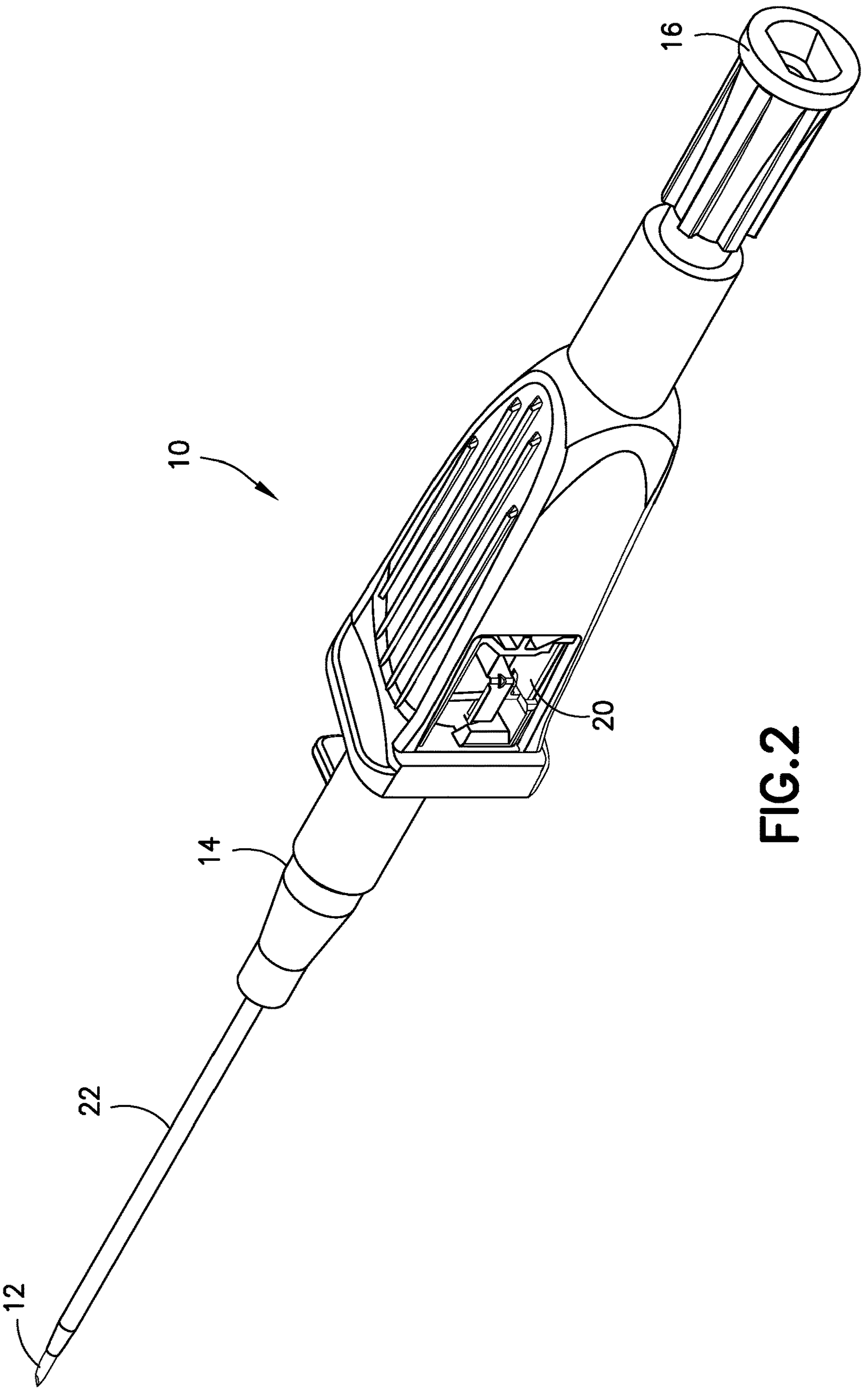
FIG. 2 illustrates a side left perspective view of a catheter assembly.
Figure 3:
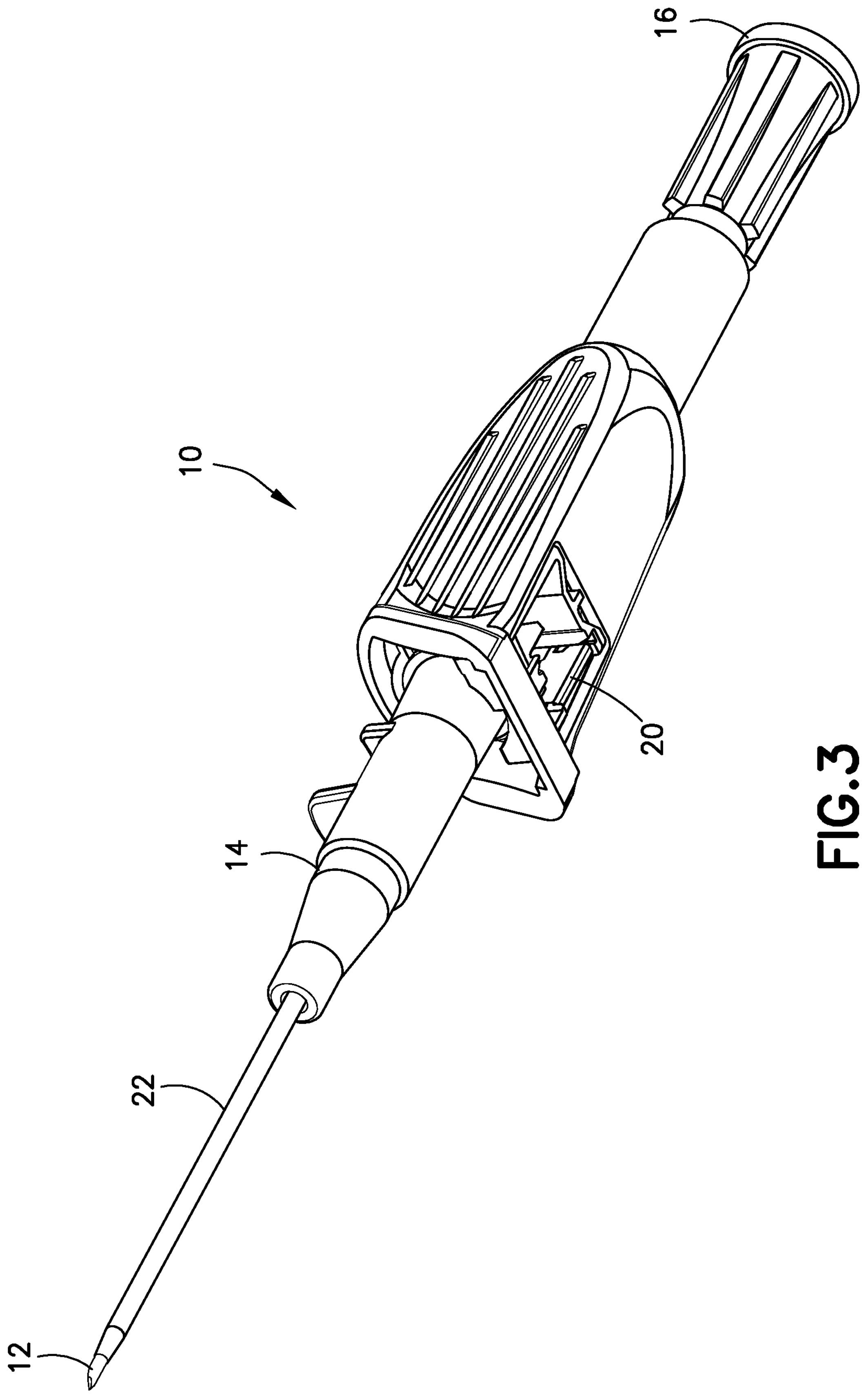
FIG. 3 illustrates an alternate side left perspective view of a catheter assembly.
Figure 4:
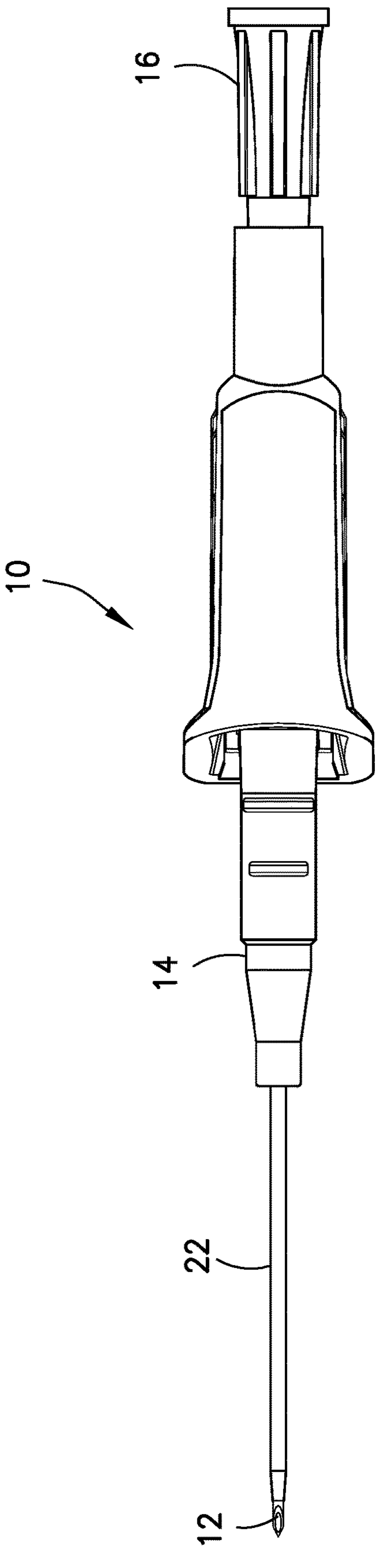
FIG. 4 illustrates a top plan view of the catheter assembly.
Figure 5:
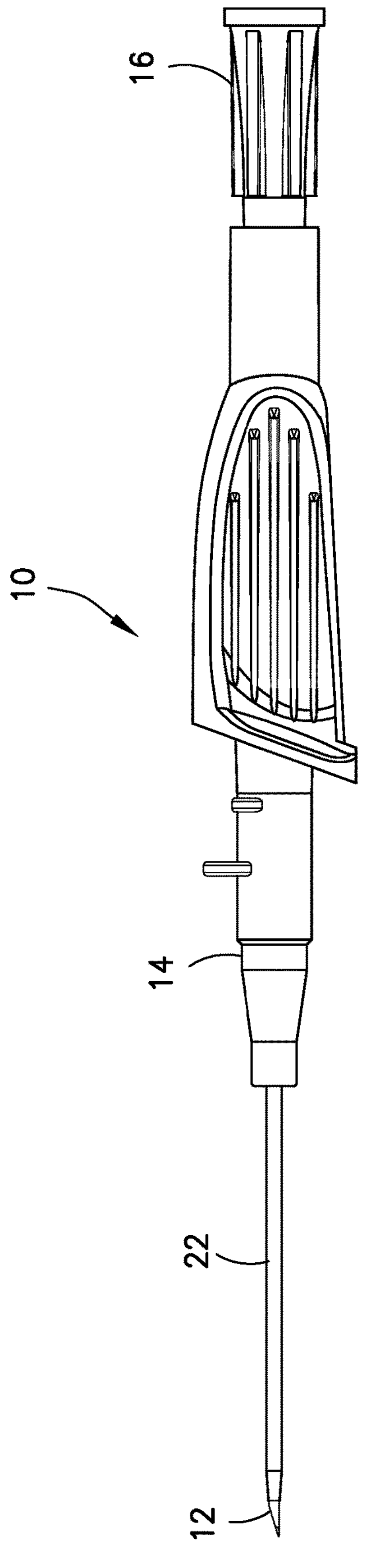
FIG. 5 illustrates a right side elevation view of the catheter assembly.
Figure 6:
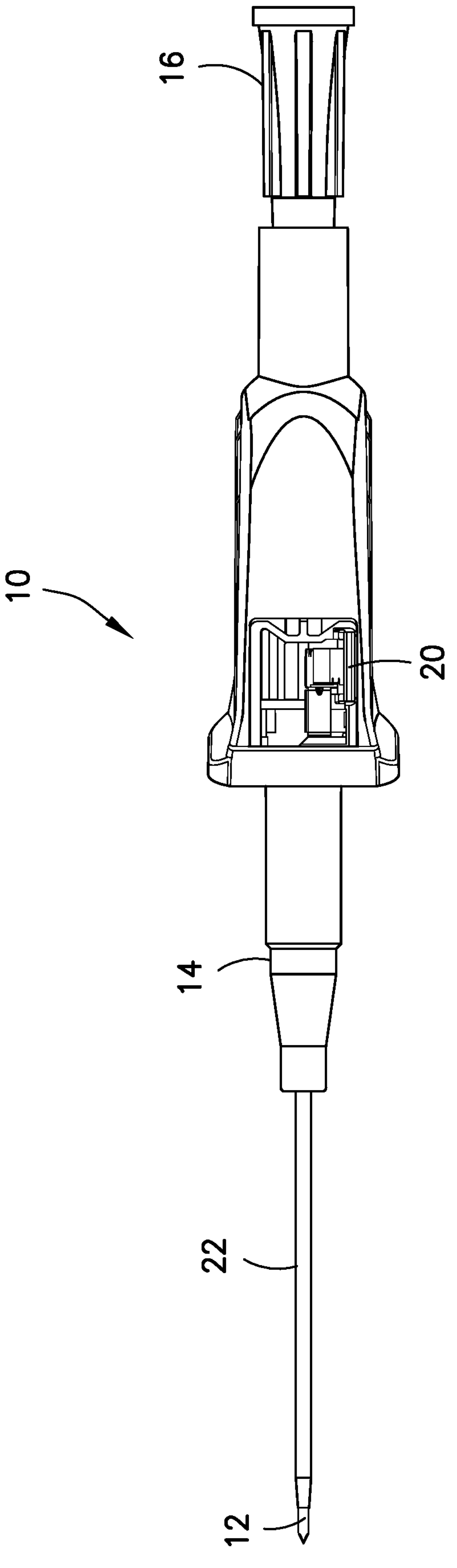
FIG. 6 illustrates a bottom plan view of the catheter assembly.
Figure 7:
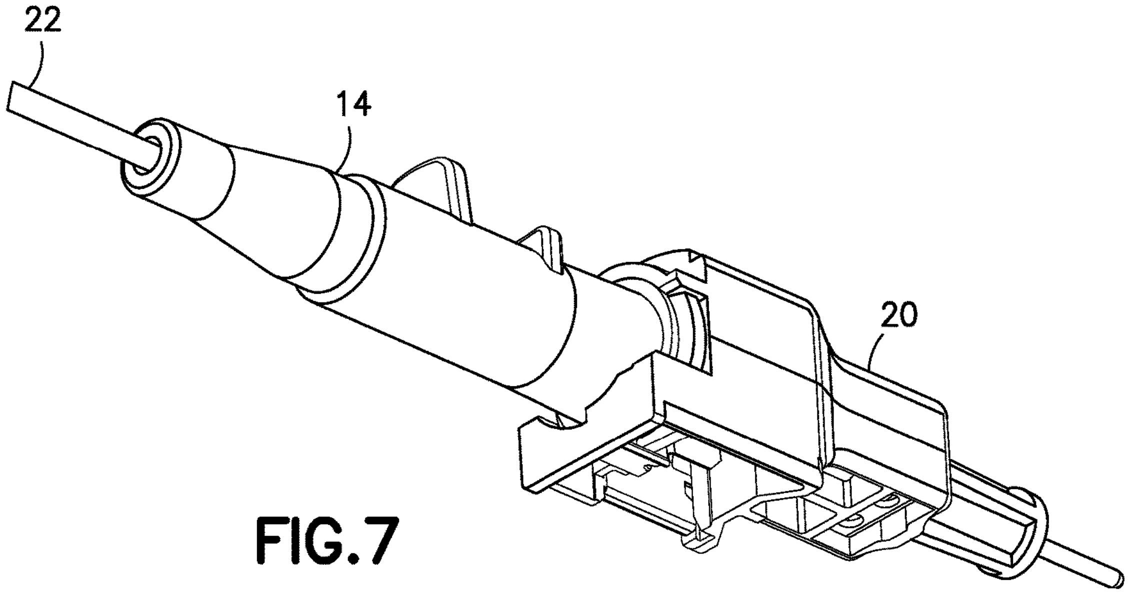
FIG. 7 illustrates a left perspective view of the assembled catheter hub, needle shield, and needle of the catheter assembly.
Figure 8:
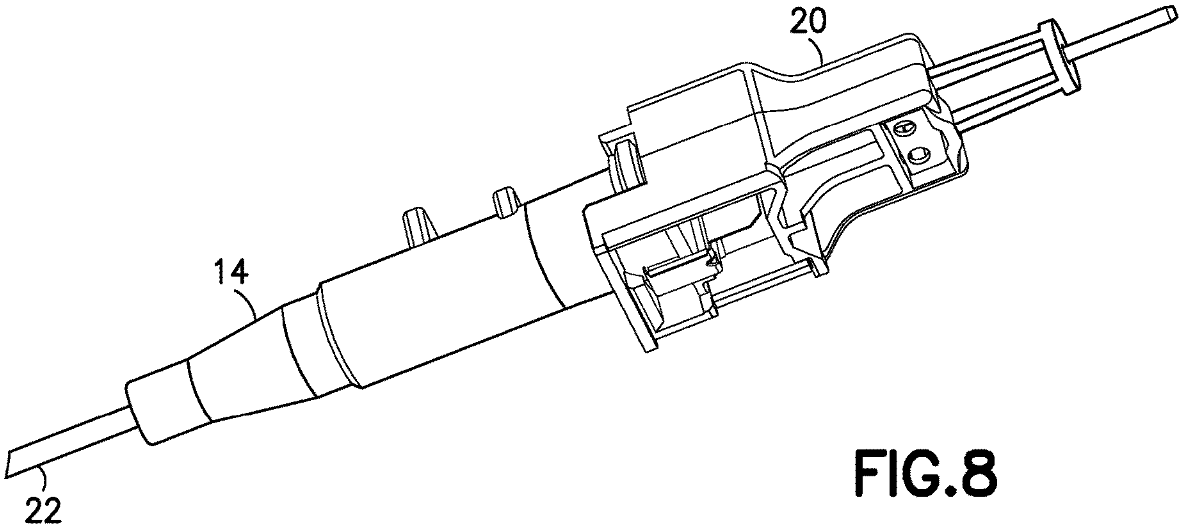
FIG. 8 illustrates a right perspective view of the assembled catheter hub, needle shield, and needle of the catheter assembly.
Figure 9:
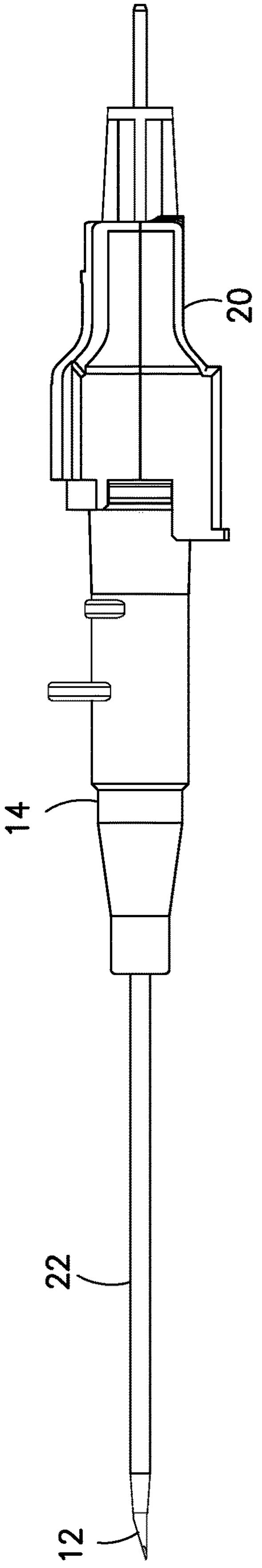
FIG. 9 illustrates a right side elevation view of the assembled catheter hub, needle shield, and needle of the catheter assembly.
Figure 10:
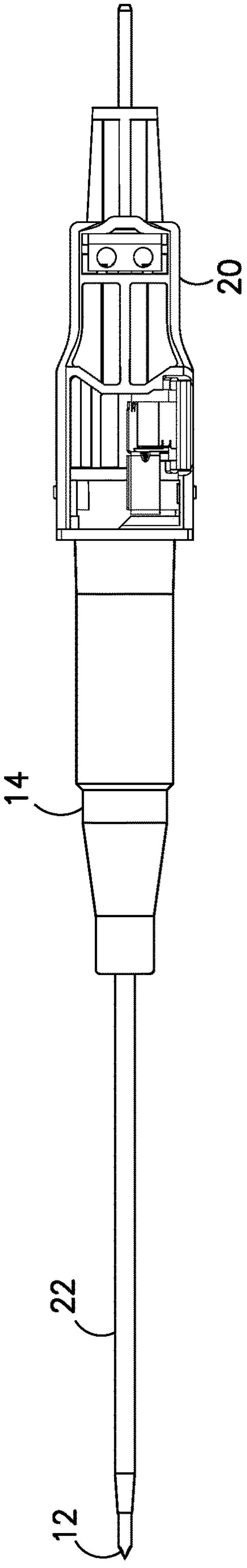
FIG. 10 illustrates a bottom plan view of the assembled catheter hub, needle shield, and needle of the catheter assembly.
Figure 11:
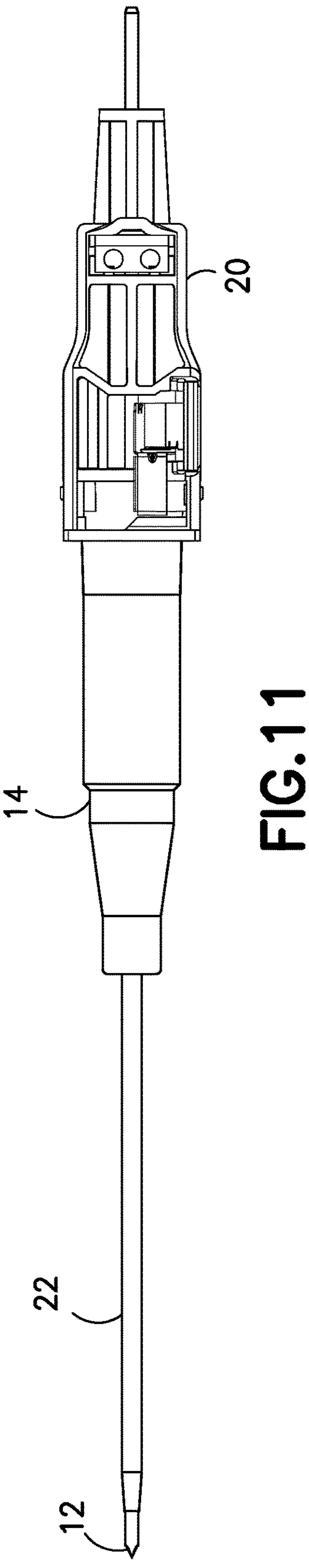
FIG. 11 illustrates a bottom plan view of the assembled catheter hub, needle shield, and needle of the catheter assembly.
Figure 12:
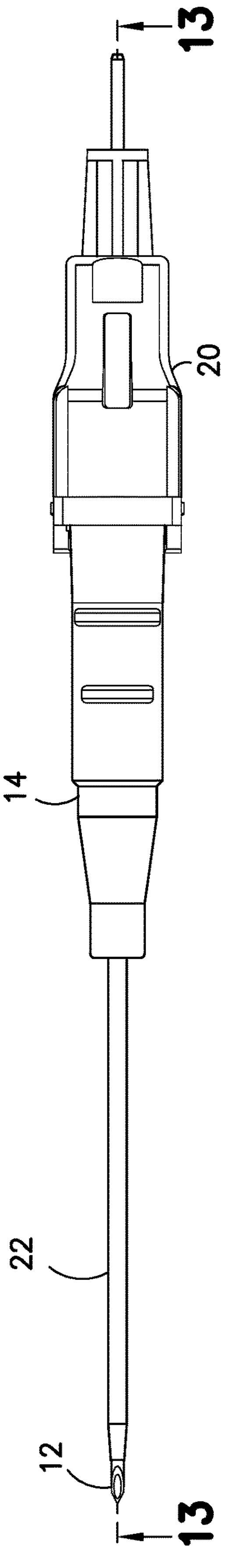
FIG. 12 illustrates a top plan view of the assembled catheter hub, needle shield, and needle of the catheter assembly.
Figure 13:
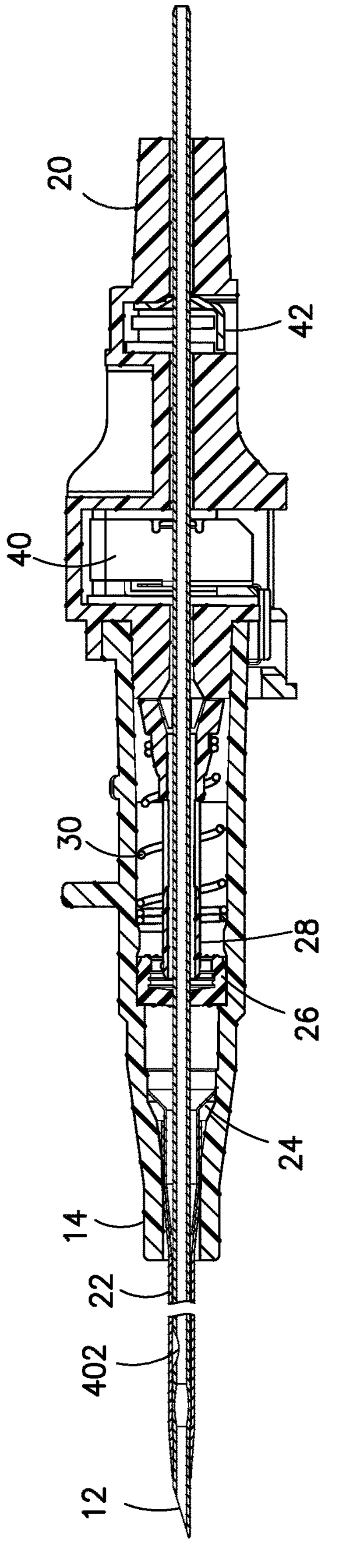
FIG. 13 illustrates a cross sectional view of a right side elevation view of the assembled catheter hub, needle shield, and needle of the catheter assembly.
Figure 14:
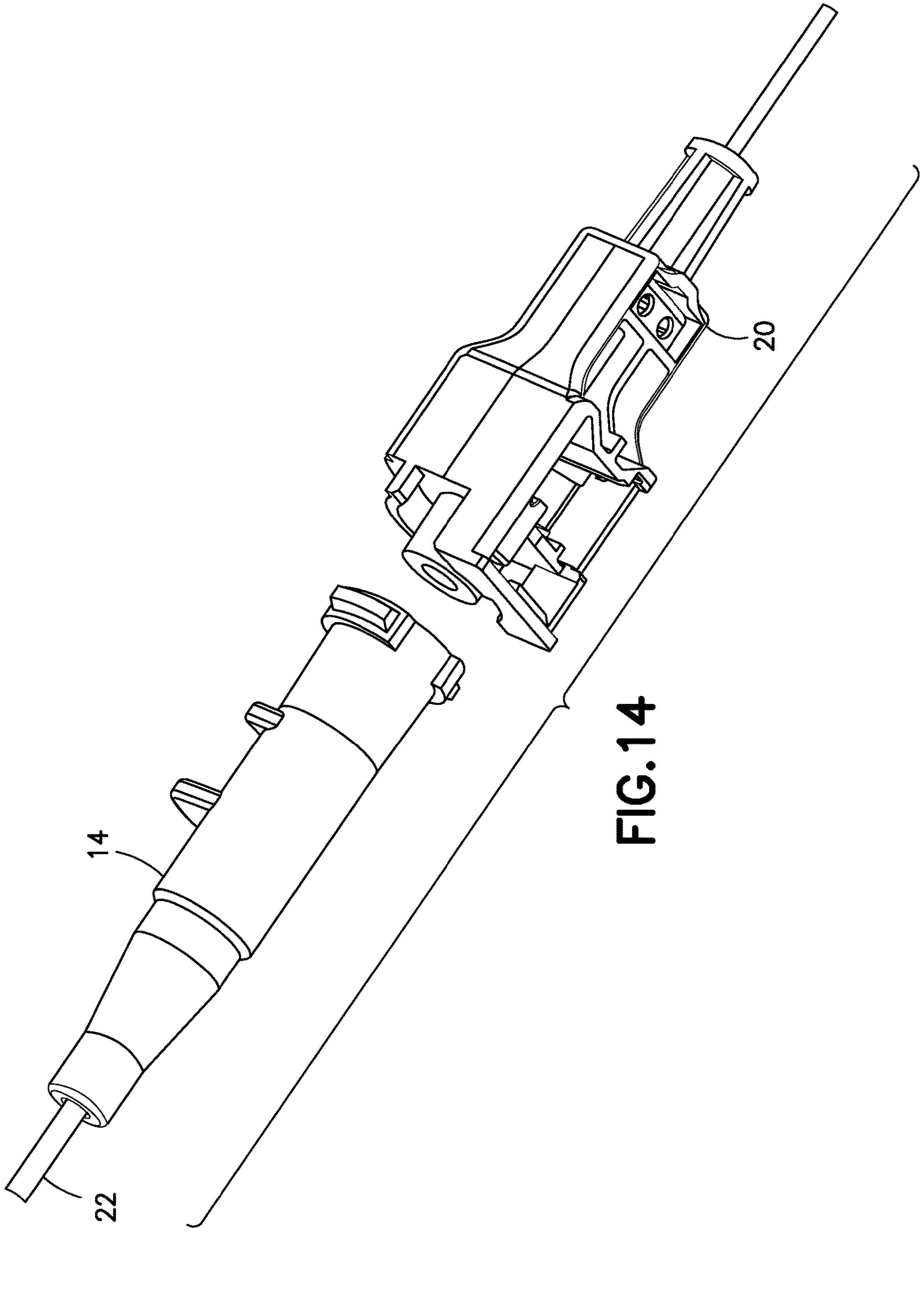
FIG. 14 illustrates a left perspective view of the separated catheter hub, needle shield, and needle of the catheter assembly.
Figure 15:
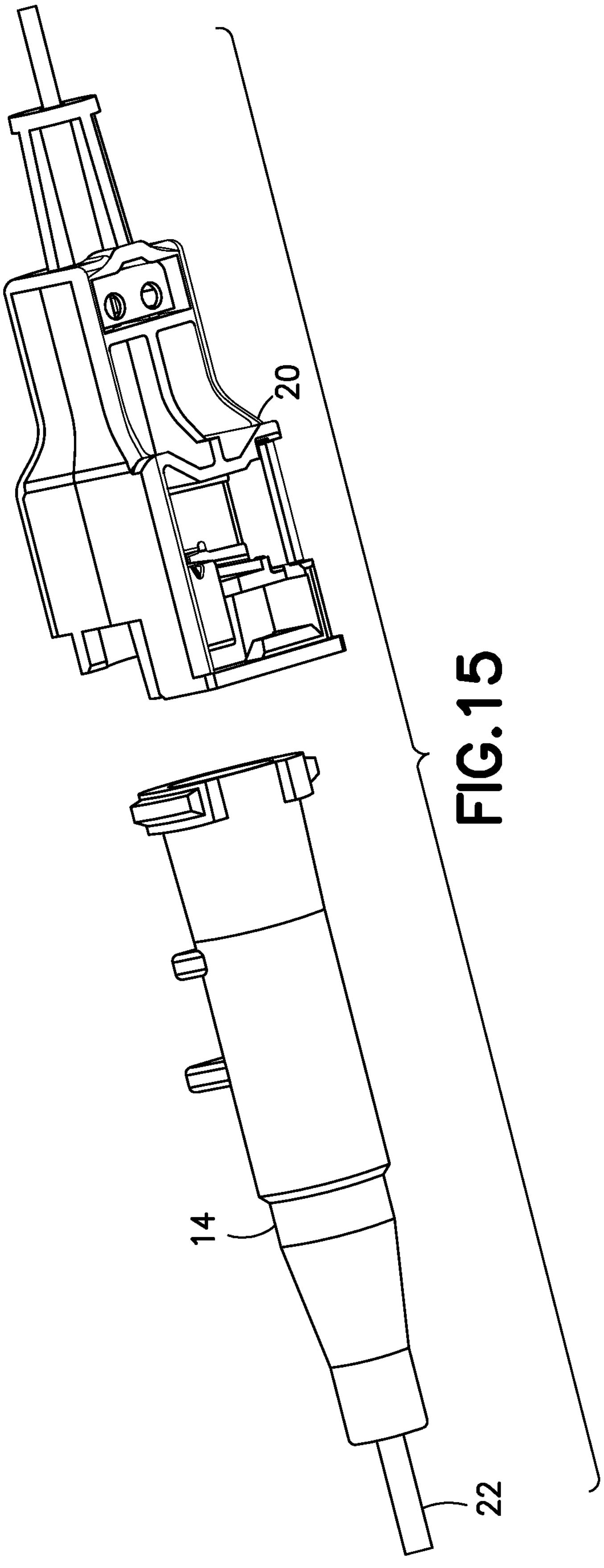
FIG. 15 illustrates a right perspective view of the separated catheter hub, needle shield, and needle of the catheter assembly.
Figure 16:
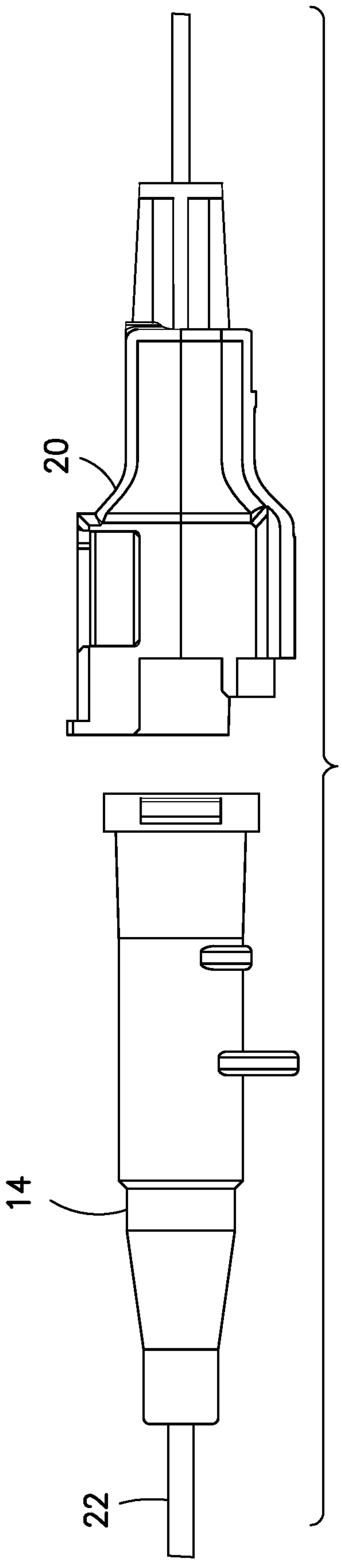
FIG. 16 illustrates a right side elevation view of the separated catheter hub, needle shield, and needle of the catheter assembly.
Figure 17:
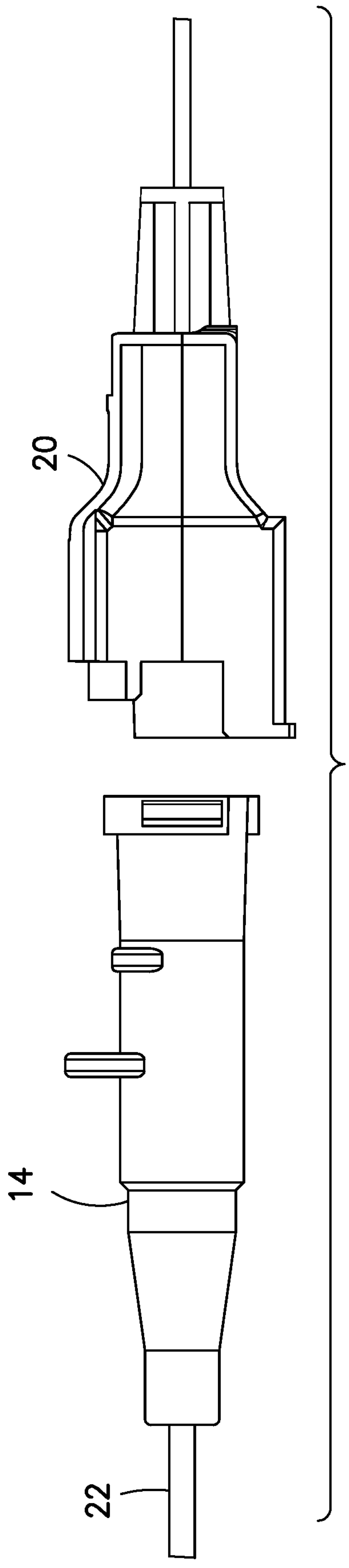
FIG. 17 illustrates a second right side elevation view of the separated catheter hub, needle shield, and needle of the catheter assembly.
Figure 18:
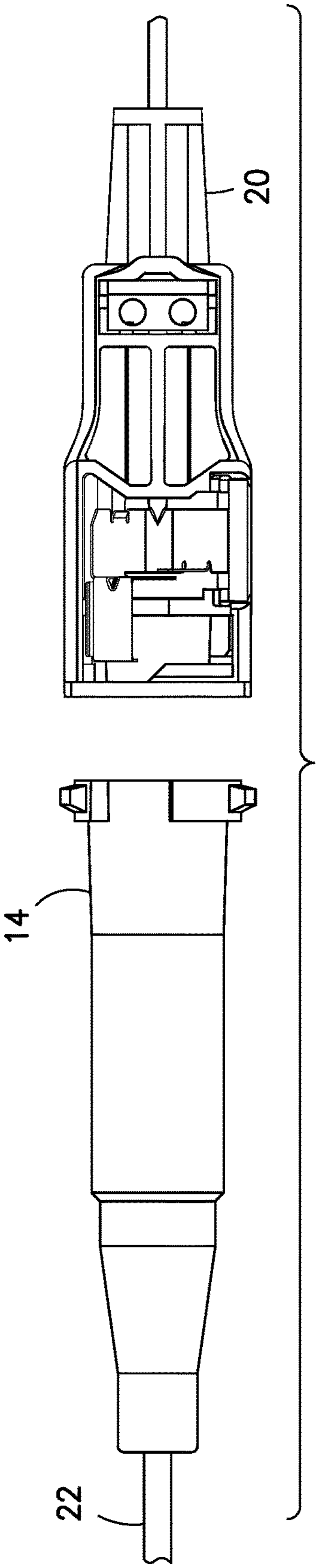
FIG. 18 illustrates a bottom plan view of the separated catheter hub, needle shield, and needle of the catheter assembly.
Figure 19:
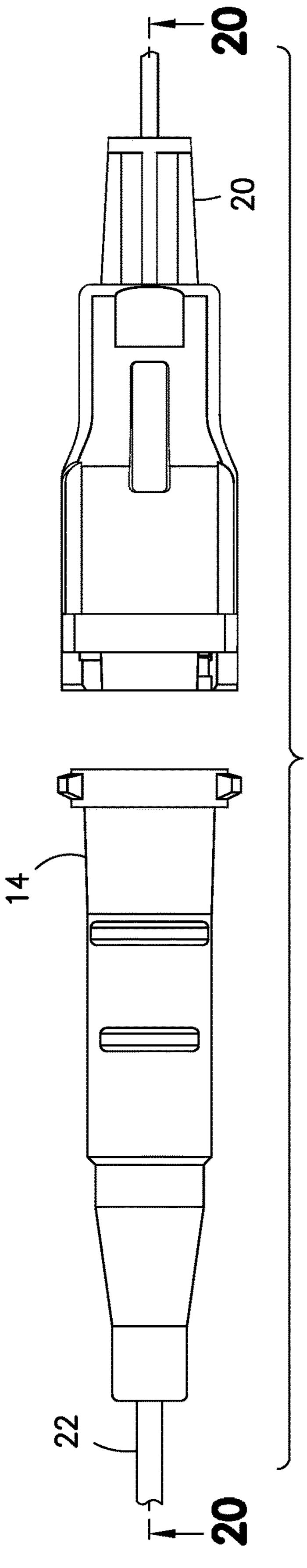
FIG. 19 illustrates a top plan view of the separated catheter hub, needle shield, and needle of the catheter assembly.
Figure 20:
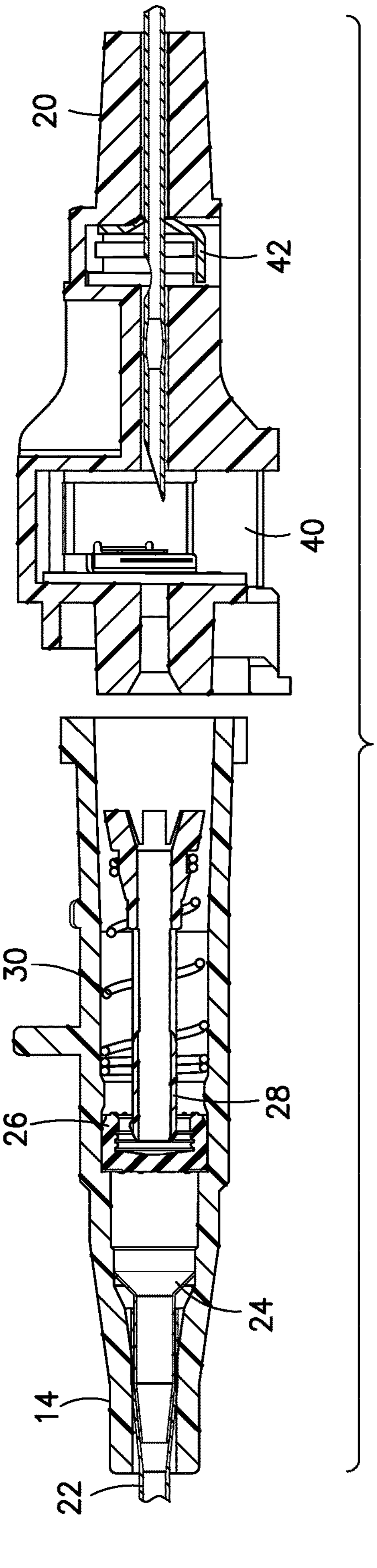
FIG. 20 illustrates a cross sectional view of a right side elevation view of the separated catheter hub, needle shield, and needle of the catheter assembly.
Figure 21:
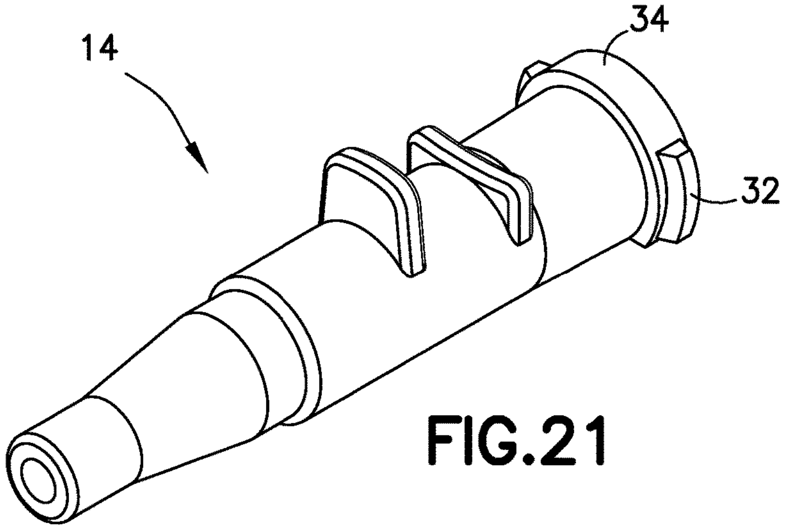
FIG. 21 is a right perspective view of the catheter hub of the catheter assembly.
Figure 22:
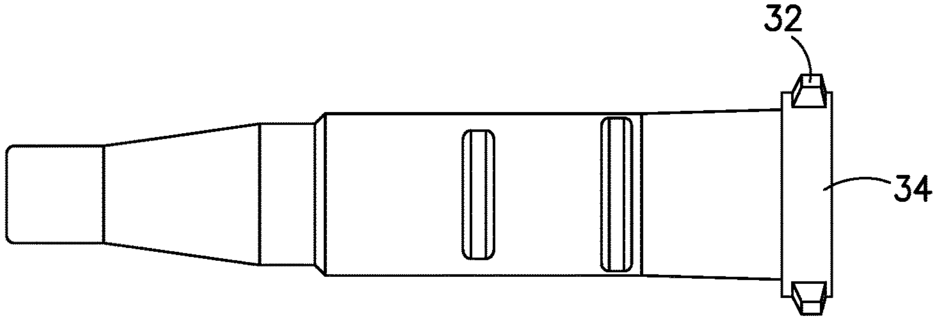
FIG. 22 is a top plan view of the catheter hub of the catheter assembly.
Figure 23:
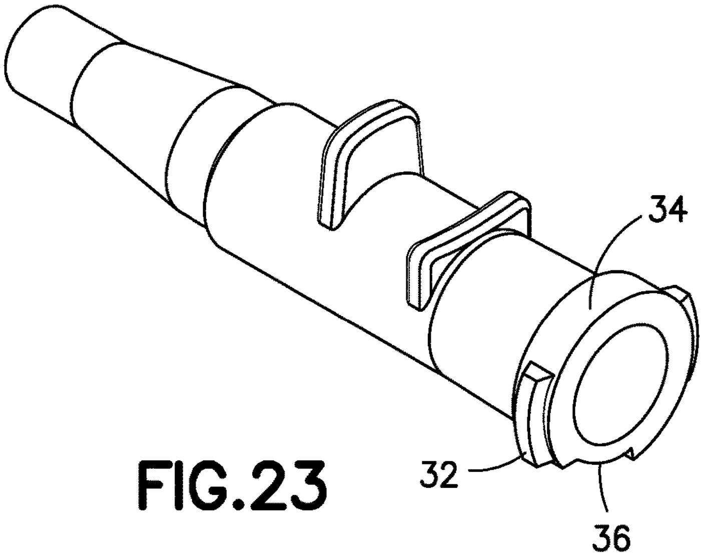
FIG. 23 is a left perspective view of the catheter hub of the catheter assembly.
Figure 24:
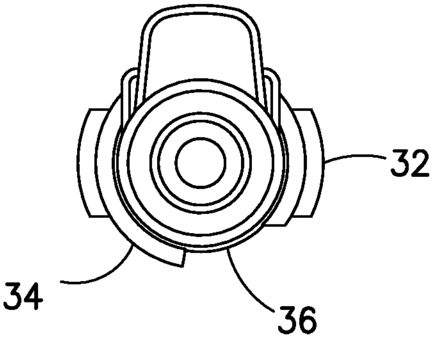
FIG. 24 is a front side view of the catheter hub of the catheter assembly.
Figure 25:
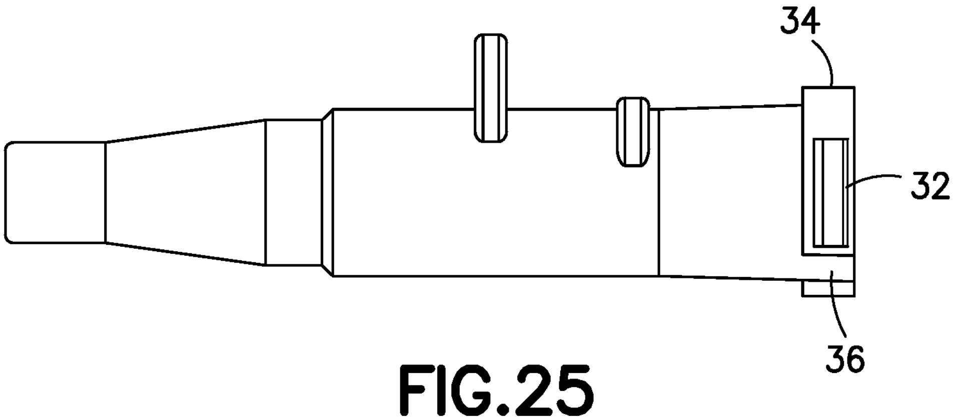
FIG. 25 is a right side view of the catheter hub of the catheter assembly.
Figure 26:
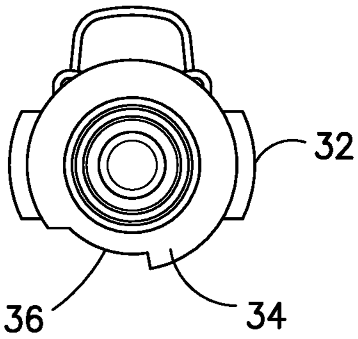
FIG. 26 is a rear side view of the catheter hub of the catheter assembly.
Figure 27:
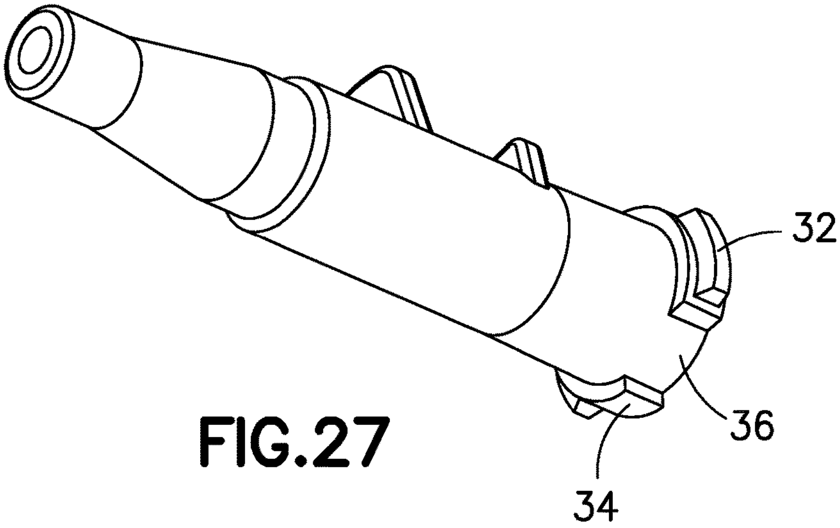
FIG. 27 is a left perspective view of the catheter hub of the catheter assembly.
Figure 28:
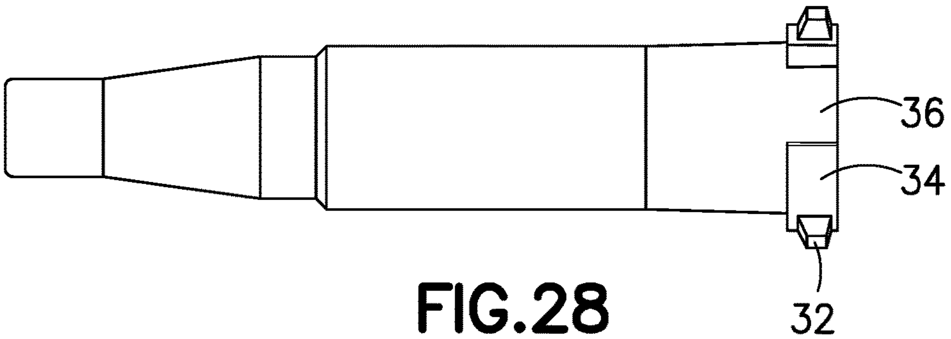
FIG. 28 is a bottom plan view of the catheter hub of the catheter assembly.
Figure 29:
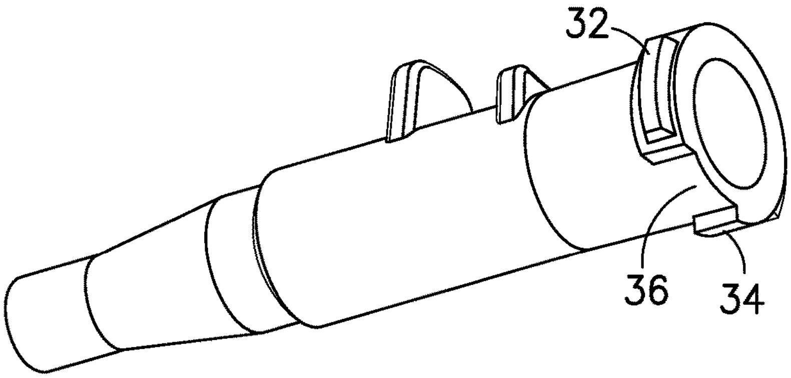
FIG. 29 is a right perspective view of the catheter hub of the catheter assembly.
Figure 30:
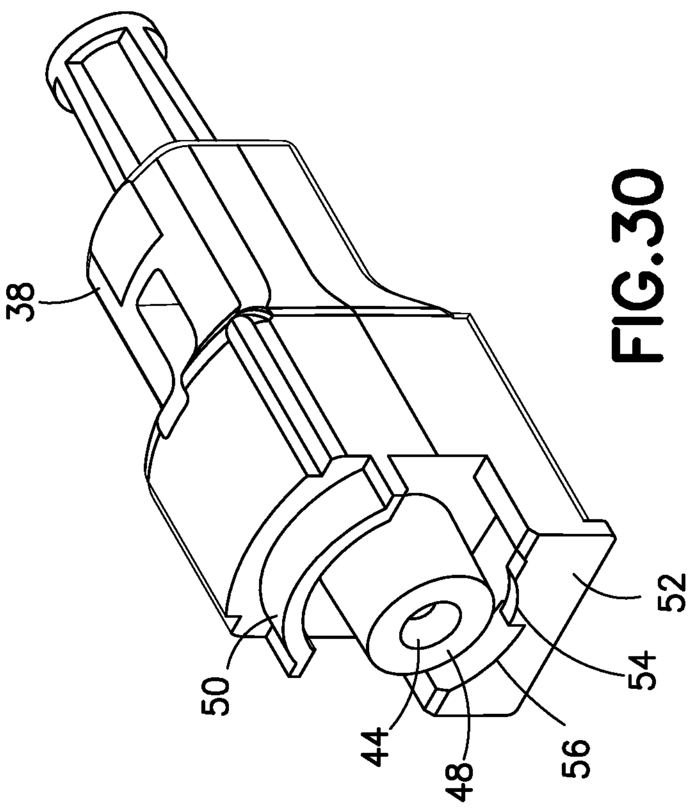
FIG. 30 illustrates a right perspective view of the needle shield outer housing of the catheter assembly.
Figure 31:
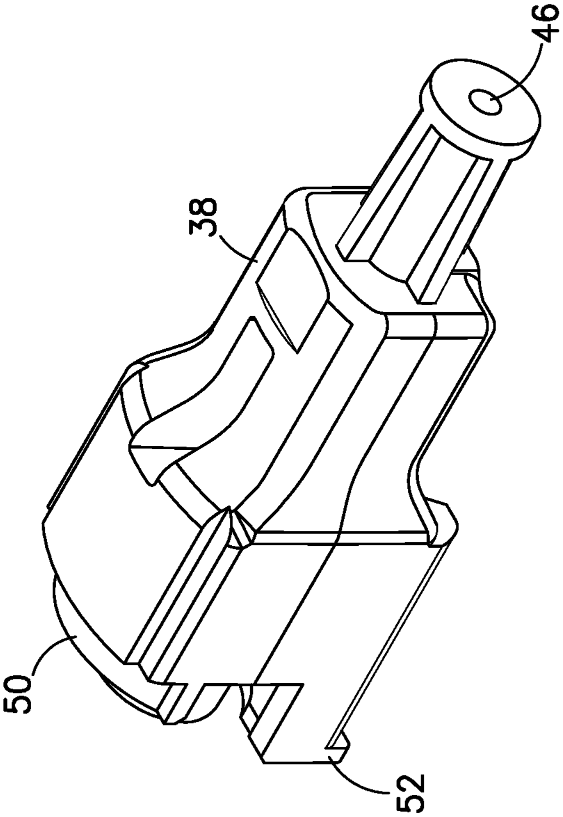
FIG. 31 illustrates a left perspective view of the needle shield outer housing of the catheter assembly.
Figure 33:
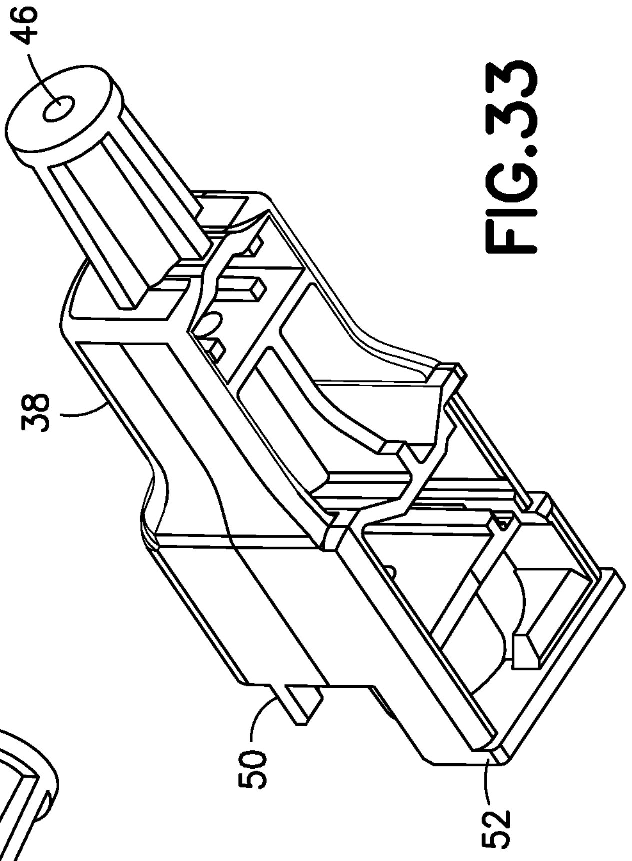
FIG. 33 illustrates a second right perspective view of the needle shield outer housing of the catheter assembly.
Figure 32:
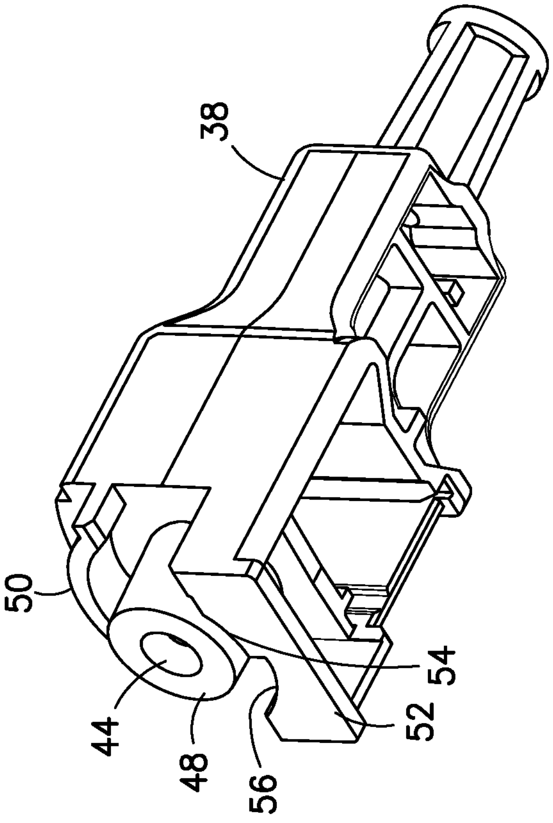
FIG. 32 illustrates a second left perspective view of the needle shield outer housing of the catheter assembly.
Figure 34:
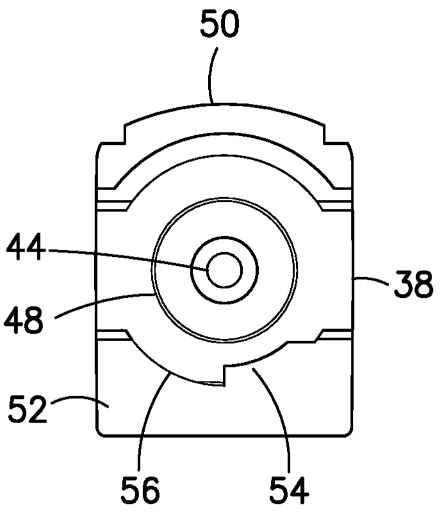
FIG. 34 illustrates a front side elevation view of the needle shield outer housing of the catheter assembly.
Figure 35:
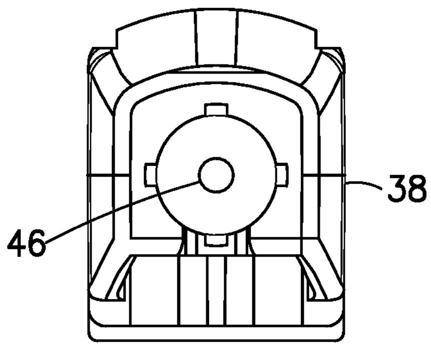
FIG. 35 illustrates a rear side elevation view of the needle shield outer housing of the catheter assembly.
Figure 36:
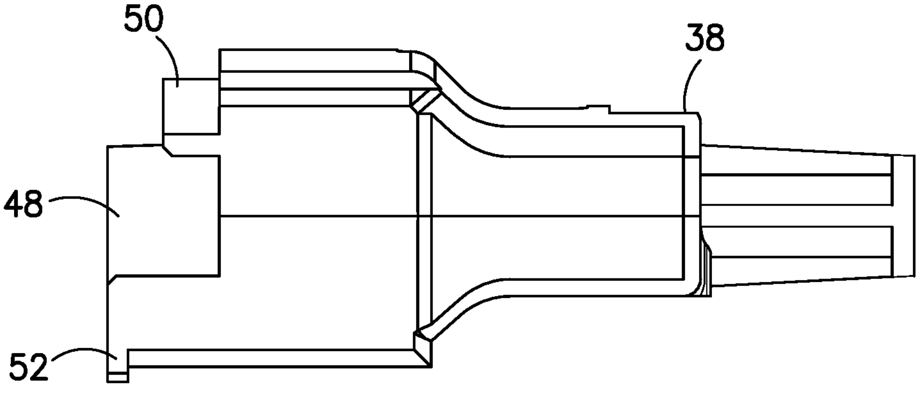
FIG. 36 illustrates a right side elevation view of the needle shield outer housing of the catheter assembly.
Figure 37:
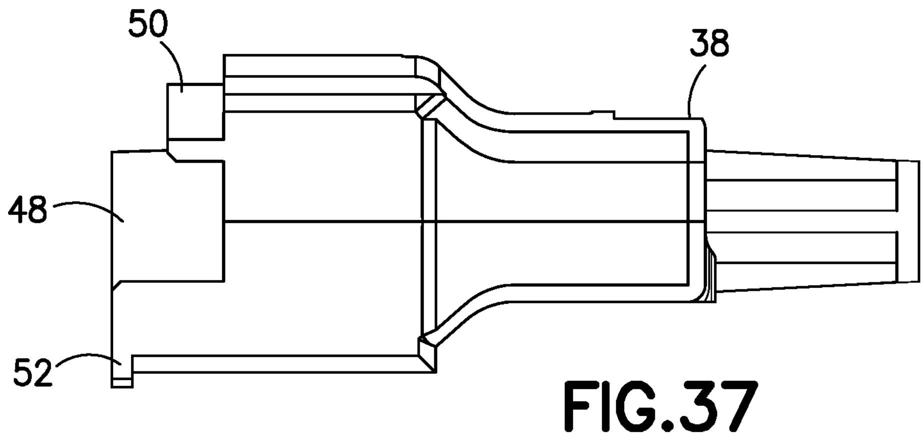
FIG. 37 illustrates a right side elevation view of the needle shield outer housing of the catheter assembly.
Figure 38:
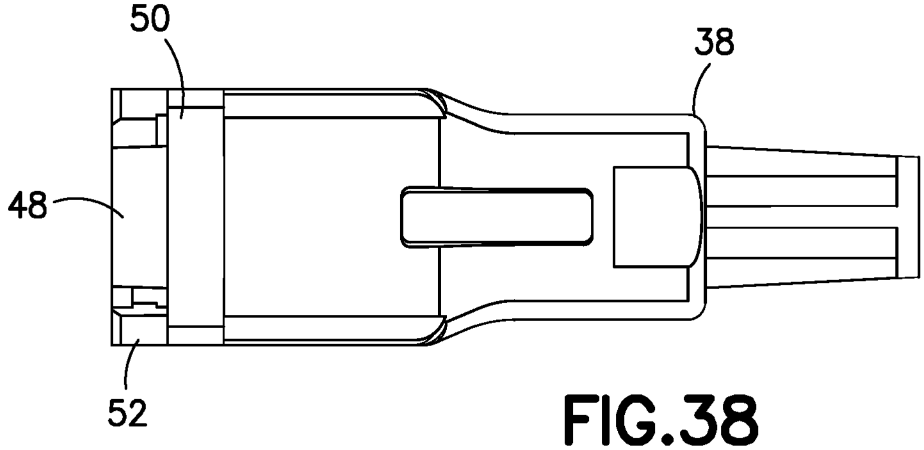
FIG. 38 illustrates a top plan view of the needle shield outer housing of the catheter assembly.
Figure 39:
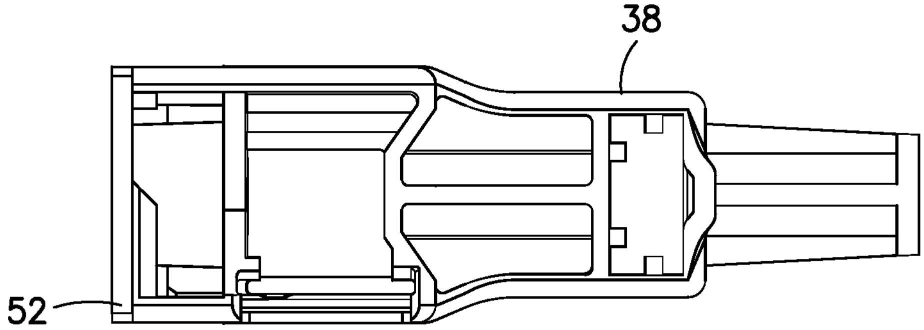
FIG. 39 illustrates a bottom plan view of the needle shield outer housing of the catheter assembly.
Figure 40:
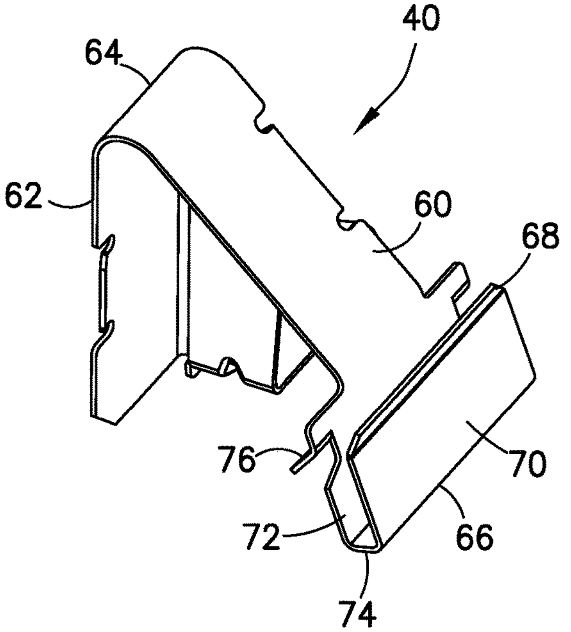
FIG. 40 illustrates a left perspective view of the V-shaped metal clip of the catheter assembly.
Figure 41:
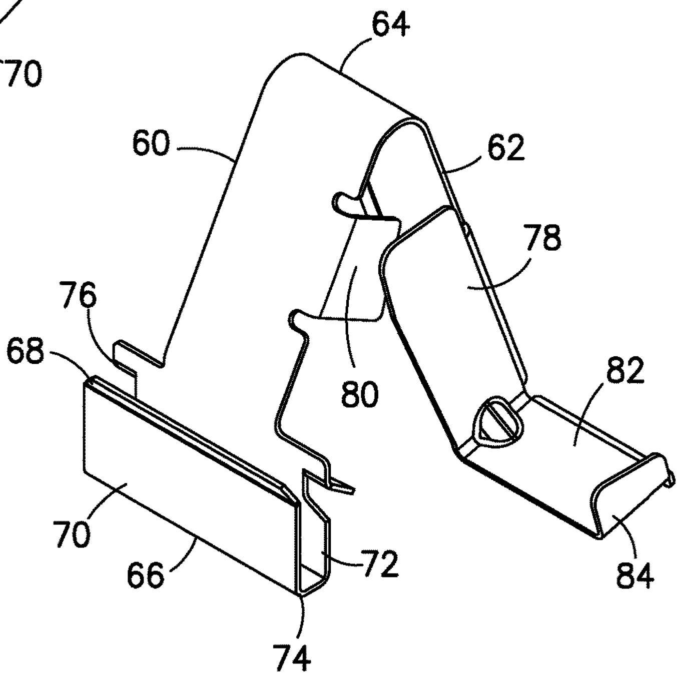
FIG. 41 illustrates a right perspective view of the V-shaped metal clip of the catheter assembly.
Figure 42:
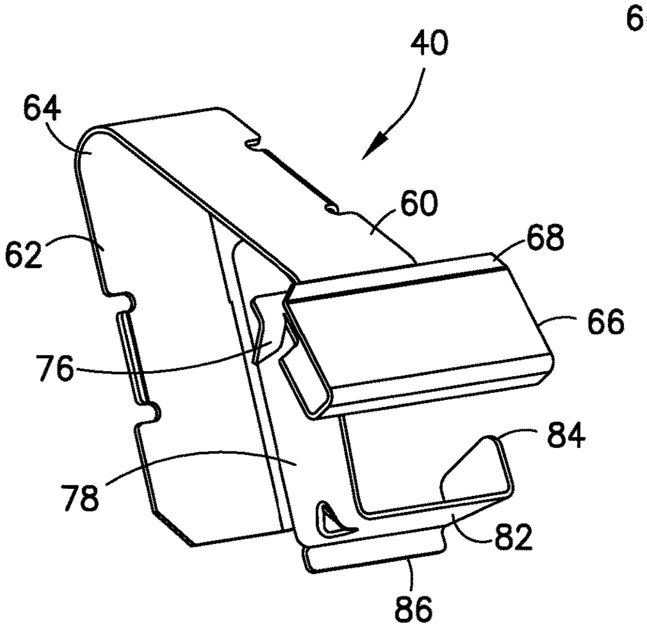
FIG. 42 illustrates a second right perspective view of the V-shaped metal clip of the catheter assembly.
Figure 43:
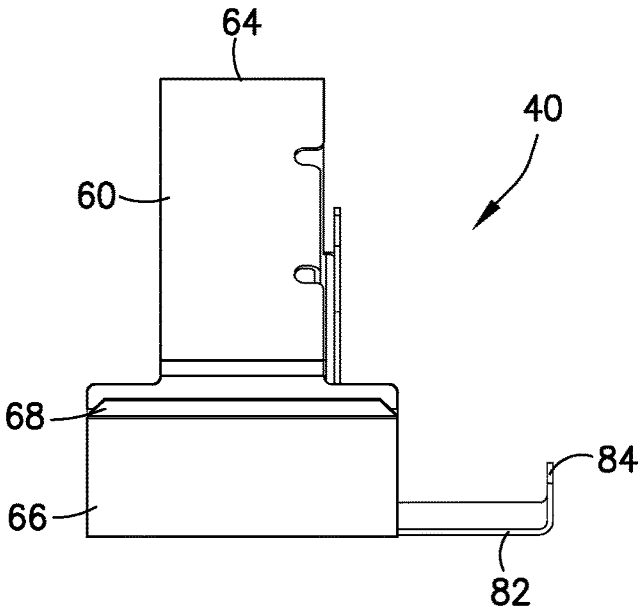
FIG. 43 illustrates a front elevation view of the V-shaped metal clip of the catheter assembly.
Figure 44:
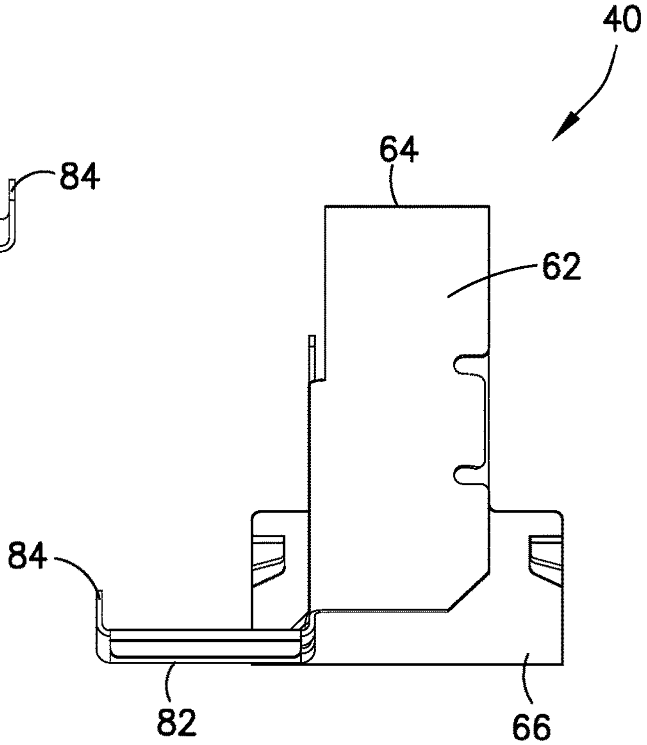
FIG. 44 illustrates a rear elevation view of the V-shaped metal clip of the catheter assembly.
Figure 45:
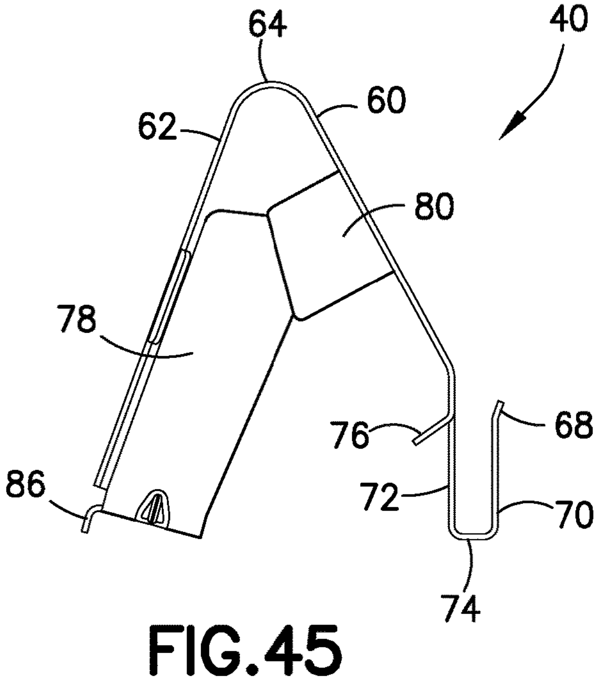
FIG. 45 illustrates a left side elevation view of the V-shaped metal clip of the catheter assembly.
Figure 46:
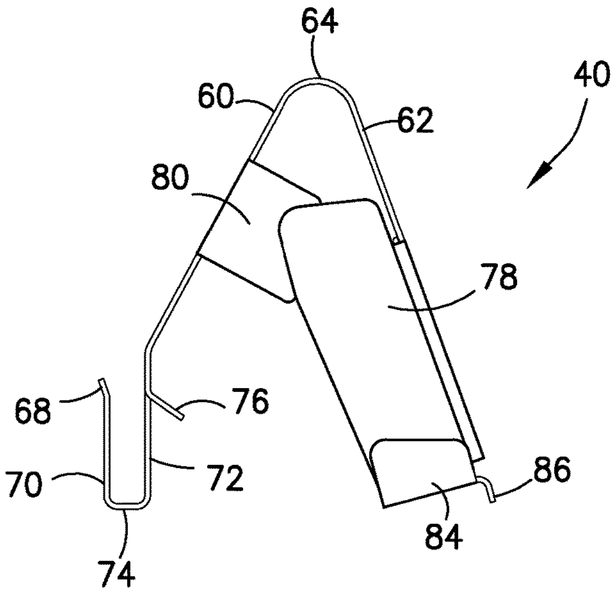
FIG. 46 illustrates a right side elevation view of the V-shaped metal clip of the catheter assembly.
Figure 47:
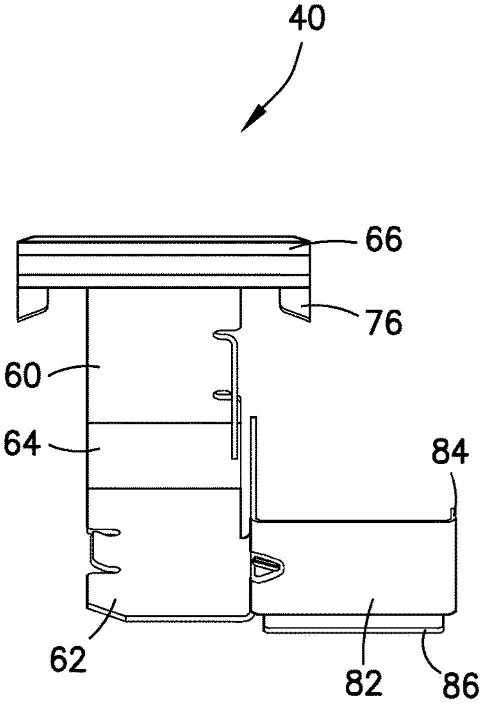
FIG. 47 illustrates a top plan view of the V-shaped metal clip of the catheter assembly.
Figure 48:
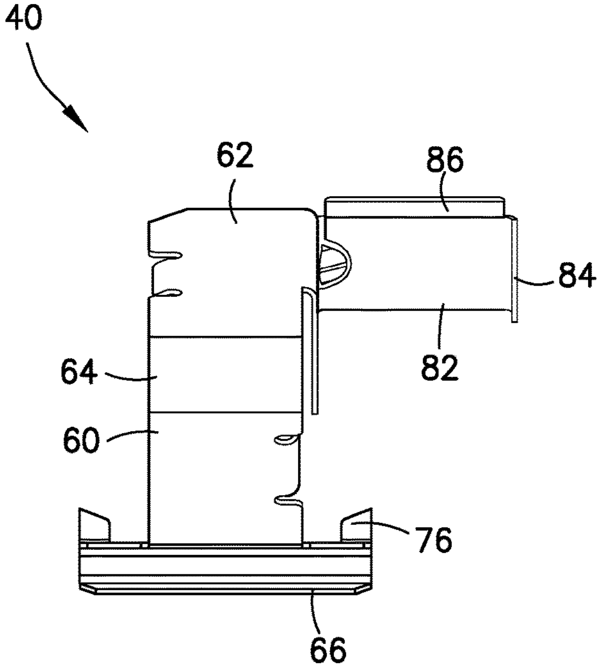
FIG. 48 illustrates a bottom plan view of the V-shaped metal clip of the catheter assembly.
Figure 49:
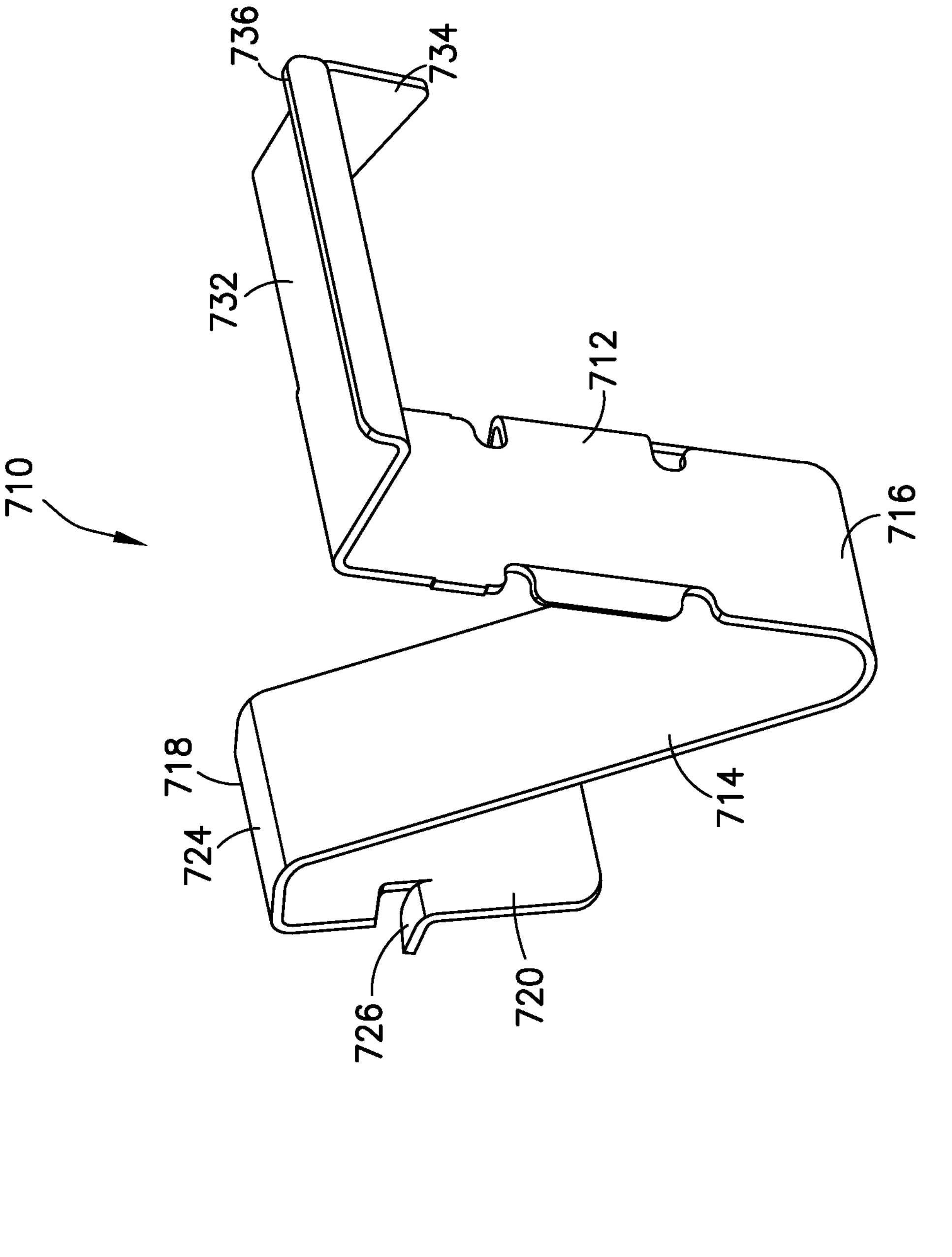
FIG. 49 illustrates a right perspective view of an alternate embodiment of the V-shaped metal clip of the catheter assembly.

FIG. 49 illustrates an alternate embodiment of a clip 710 having a substantially V shape with a first leg 712 and a second leg 714 connected by a curved section 716. The second leg 714 includes a spade 718. The spade 718 includes an outer wall 720 connected to the second leg 714 by a bottom portion 724. An inner wall of the spade 718 is not present in this embodiment because the second leg 714 is fully extended to the top of the spade 718. Thus, the spade 718 does not have a substantially U shape. A pair of barbs 726 (only one is visibly illustrated) extends outwardly from the outer wall 720 of the spade 718.

FIG. 49 further illustrates a foot 732 extends outwardly and away from the first and second legs 712, 714 and a latch

734 extends upwardly from the foot 732. The latch 734 is positioned outside an area between the first and second legs 712, 714. Specifically, the latch 734 is disposed outside of an area between a plane representing the first leg 712 and a plane representing the second leg 714. A rib 736 extends downwardly from the foot 732 to stiffen and strengthen the clip 710.

Figure 50:
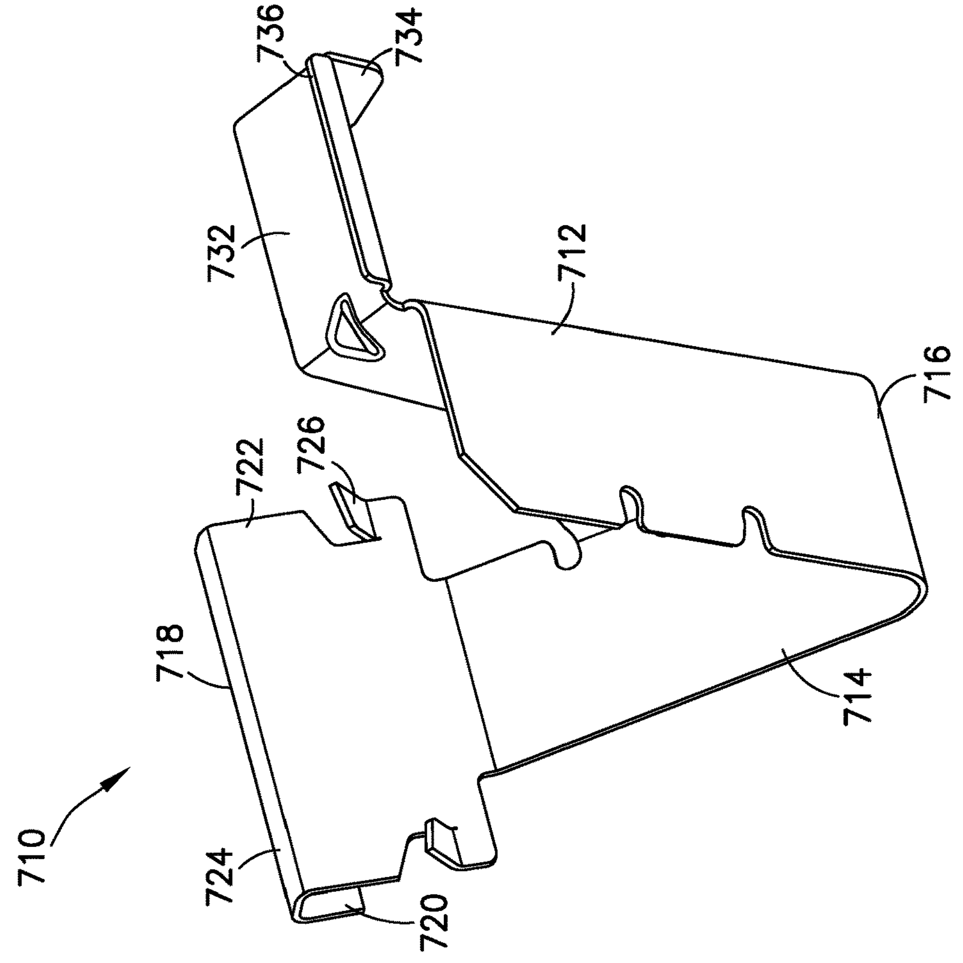
FIG. 50 illustrates a right perspective view of an alternate embodiment of the V-shaped metal clip of the catheter assembly.

FIG. 50 illustrates an alternate embodiment of a clip 710 including a U-shaped spade 718 having an outer wall 720 and an inner wall 722. The spade 718 is located on a bottom portion of the outer and inner walls 720, 722. The inner wall 722 reduces the length of the second leg 714 but the inner wall 722 includes barbs 726 that secure the clip 710 to the needle shield. Moving the barbs 726 from the outer wall 720 to the inner wall 722 advantageously makes the clip 710 narrower. Specifically, an outer wall of the needle shield can be removed while still adequately securing the clip 710. Additionally, the clip 710 includes a foot 732 and a latch 734 that are disposed between the first and second legs 712, 714. In other words, the foot 732 and latch 734 are positioned between a plane representing the first leg 712 and a plane representing the second leg 714.

Figure 51:
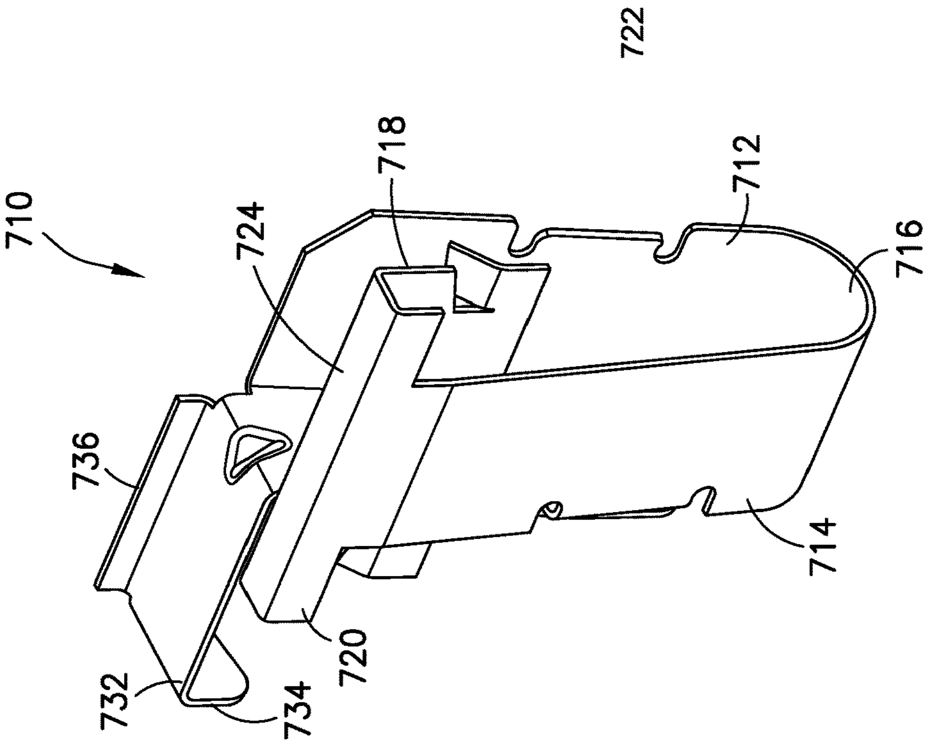
FIG. 51 illustrates a left perspective view of an alternate embodiment of the V-shaped metal clip of the catheter assembly.
Figure 52:
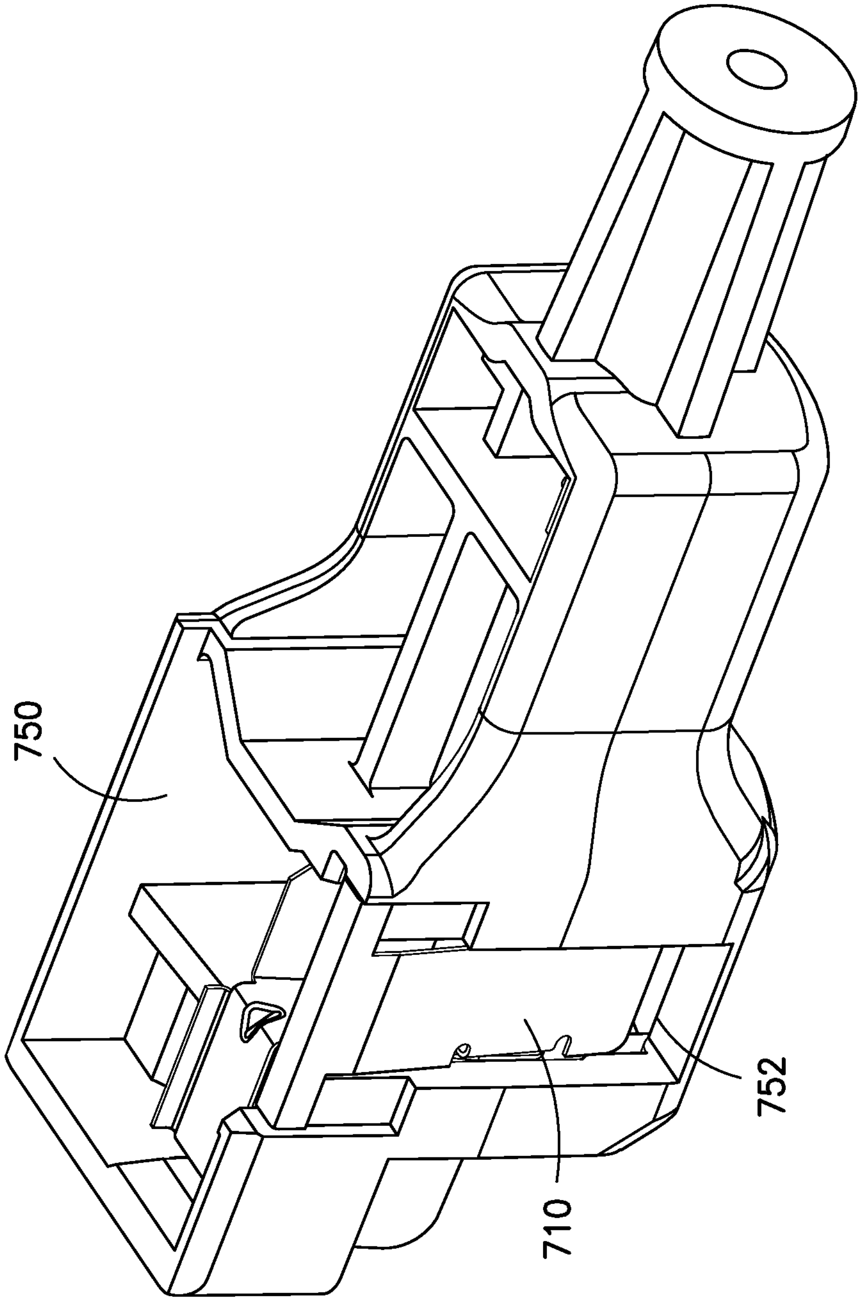
FIG. 52 illustrates a left perspective view of the V-shaped metal clip of FIG. 51 inserted into a needle shield.

FIGS. 51 and 52 illustrate an alternate embodiment of a clip 710 having a longer second leg 714 that is exposed to the outside of the needle shield 750. Specifically, the needle shield 750 is covered by the needle hub, so that the clip 710 is not exposed to the outside environment, just to the outside of the needle shield 750. The spade 718 is disposed between a plane representing the first leg 712 and a plane representing the second leg 714 making the clip 710 even narrower. Barbs (not illustrated) can also be present at the inner wall 722 of the spade 718 to secure the clip 710.

According to another alternate embodiment of the clip 710 of FIG. 51, the curved section 716 between the first and second legs 712, 714 can be a flat surface. In this manner, the spade 718 can pinch or draw the flat surface and the bottom portion 724 together. Such a design can provide increased retention of the clip 710.

The longer second leg 714 has several advantages. A longer spring leg creates a more flexible V shaped spring where the spring force is more evenly applied across the length of the second leg 714. Additionally, a more flexible clip 710 reduces the stiffness and the internal stress while improving the overall life of the spring. However, in this instance, an opening 752 in the needle shield 750 for the clip 710 for assembly access and operation reduces the stiffness and overall strength of the needle shield 750.

Figure 53:
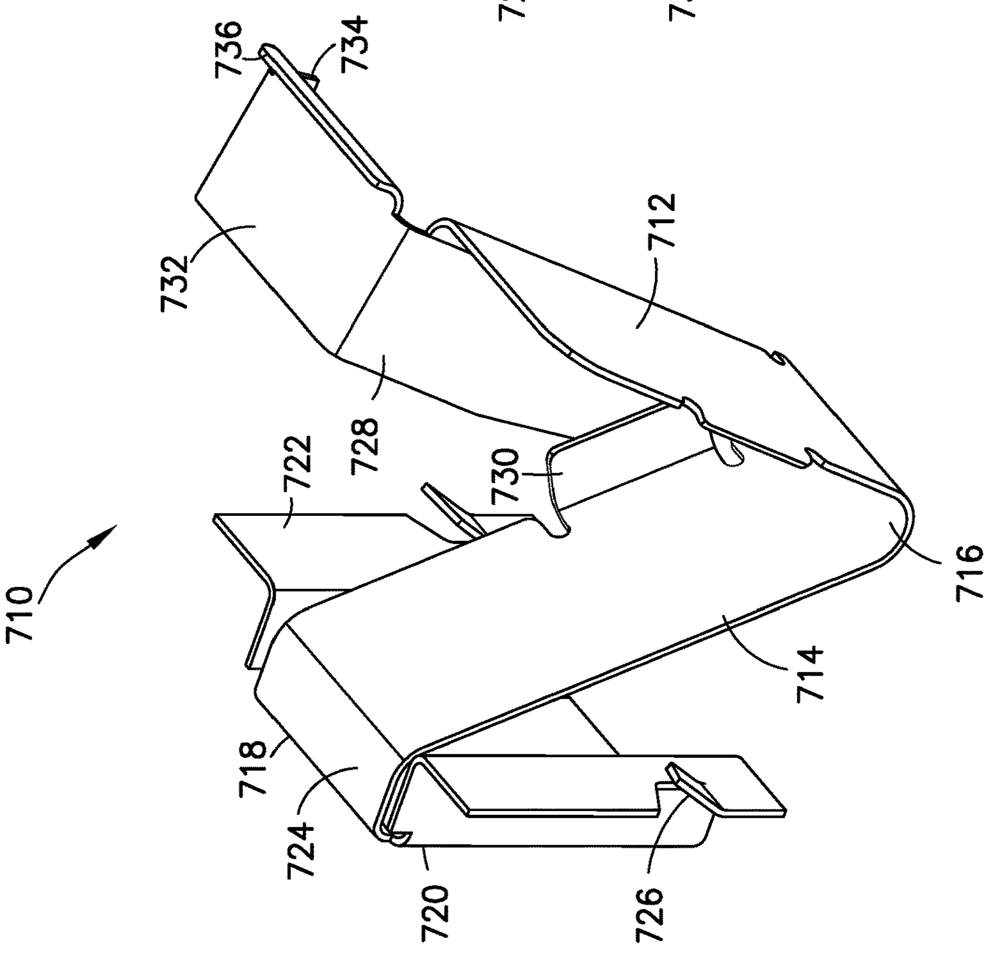
FIG. 53 illustrates a right perspective view of an alternate embodiment of the V-shaped metal clip of the catheter assembly.
Figure 54:
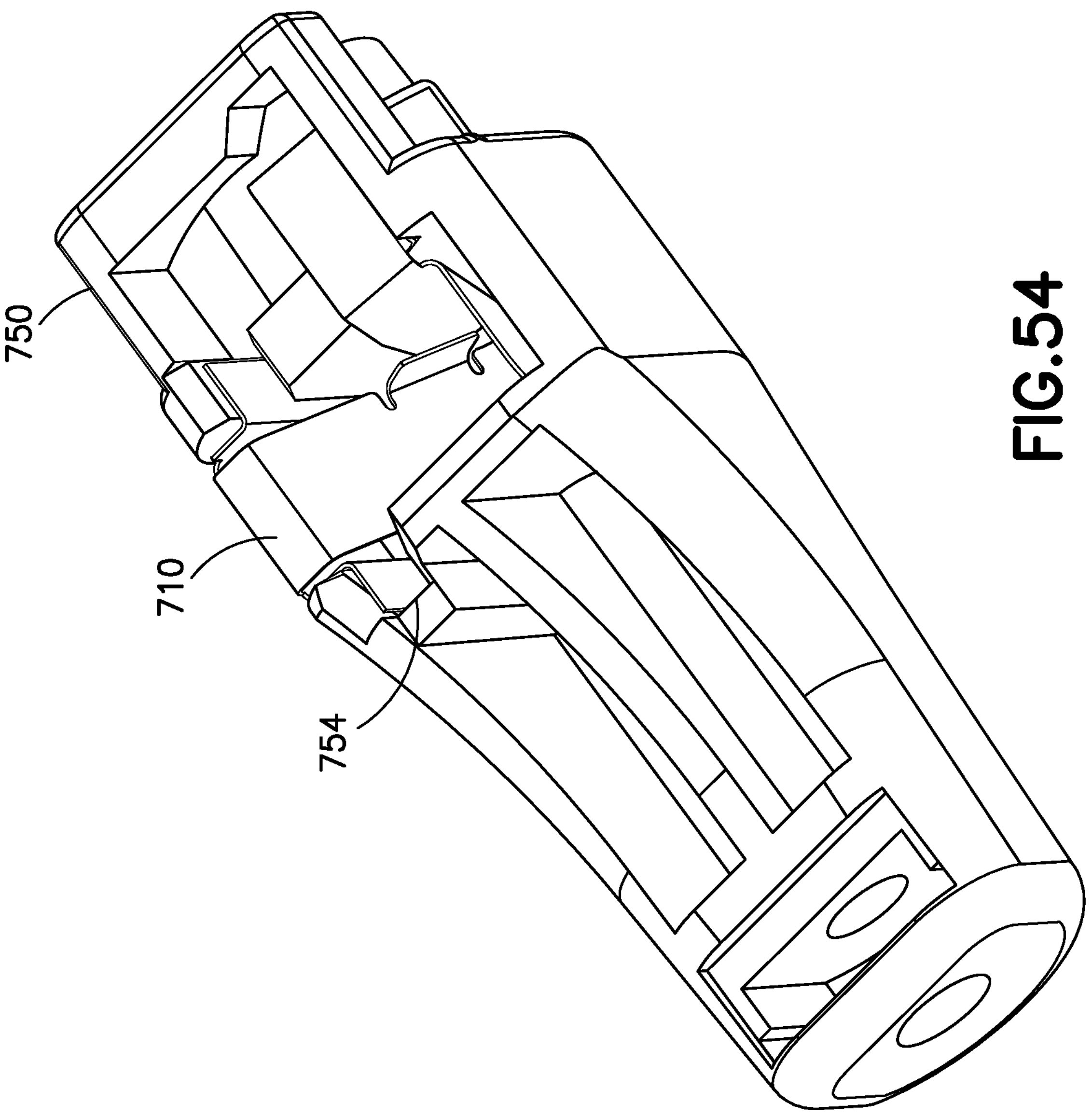
FIG. 54 illustrates a right perspective view of the V-shaped metal clip of FIG. 53 inserted into a needle shield.

FIGS. 53 and 54 illustrate an alternate embodiment of a clip 710 having a longer second leg 714 with the advantages described above. The outer wall 720 of the spade 718 extends further upward to cover the modified opening 752 of the needle shield 750 upon assembly. Accordingly, such a design can block debris or blood from entering the clip 710 and the needle shield 750 and protect the catheter assembly from the outside environment.

The clip 710 includes a first flag 728 and a second flag 730. The first flag 728 is directly connected to the first leg 712 and the foot 732 to for the following advantages. The flag design improves the overall strength of the clip 710, eases manufacturability, creates a more compact design and reduces metal scrap. On the other hand, the second flag 730 is directly connected to only the second leg 714. The two flags 728, 730 cooperate together to block the opening of the needle shield when the needle is in a retracted position inside the needle shield.

The spade 718 is not U shaped. Rather, the outer wall 720 is bent inward on both sides of the second leg 714 and then bent outward and away from each side of the second leg 714. Thus, the inner wall 722 is substantially parallel to the outer wall 720 but the inner wall 722 is not directly connected to the width of the second leg 714. On the other hand, the inner wall 722 is present adjacent to a front and rear plane of the second leg 714. Slots 754 in the needle shield 750 engage the barbs 726 and the inner wall 722 to secure the clip 710.

Although the needle shield 750 in this embodiment is stronger than in the embodiment of FIG. 52, the modified opening 752 still weakens the needle shield 750. Also, the clip 710 includes additional bends and increased complexity that pose challenges during manufacturing.

Figure 55:
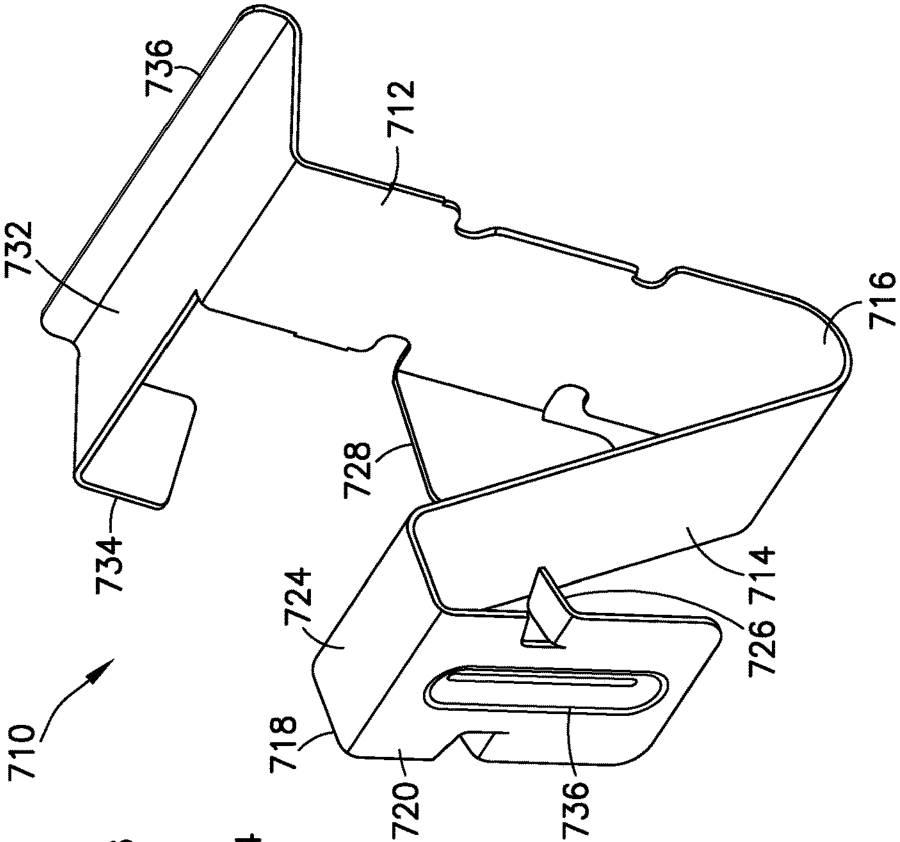
FIG. 55 illustrates a left perspective view of an alternate embodiment of the V-shaped metal clip of the catheter assembly.

FIG. 55 illustrates an alternate embodiment of a clip 710 including a rib 736 on the outer wall 720 and a rib 736 on the foot 732. When the barbs 726 of the outer wall 720 of the spade 718 engage an outer wall of the needle shield, a counteracting resistance force is applied to the clip 710. Depending on the amount of counteracting force applied, the clip 710 at the spade 718 could plastically deform or even fail. It is preferred that the clip 710 at the spade 718 only experience elastic deformation to maintain an appropriate spring life.

The rib 736 acts as a stiffener to increase the strength of the clip 710 and reduce the likelihood of the clip 710 to permanently bend or buckle. The clip 710 also includes a flag 728. The flag 728 is directly connected to the first leg 712 only. Thus, there is a gap between the flag 728 and the foot 732 to advantageously aid for the purposes of tooling in manufacturability, forming and assembly.

Figure 56:
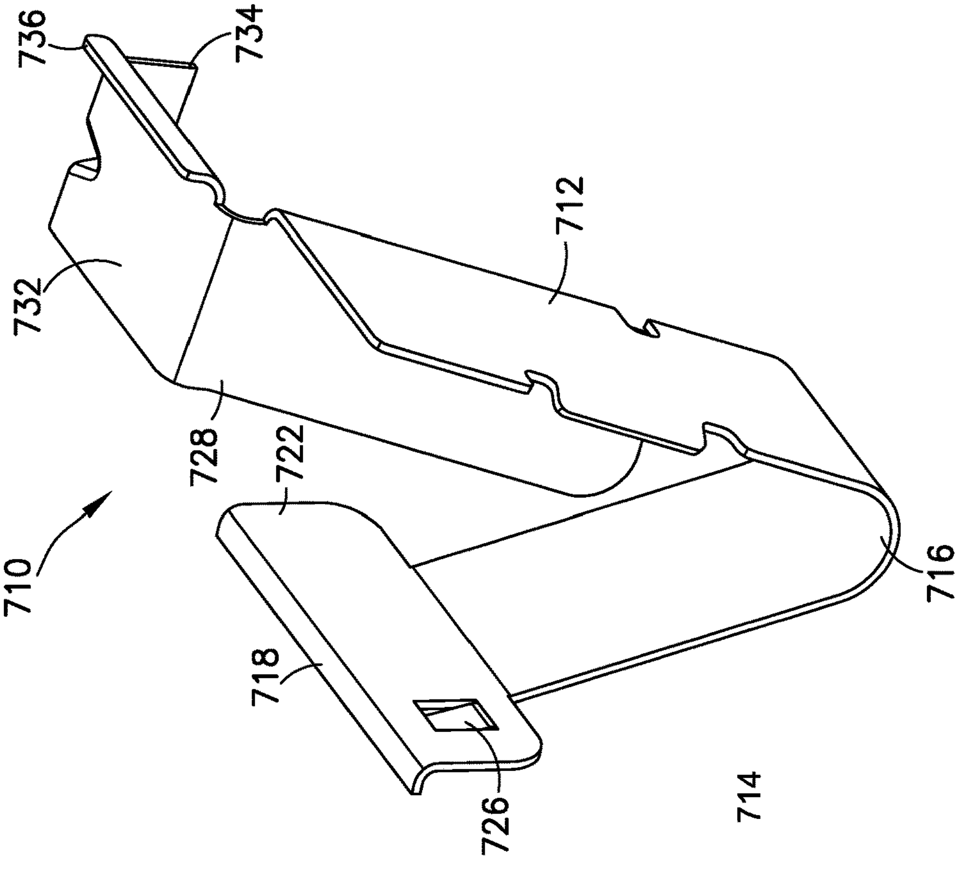
FIG. 56 illustrates a right perspective view of an alternate embodiment of the V-shaped metal clip of the catheter assembly.

FIG. 56 illustrates an alternate embodiment of a clip 710 including a spade 718 that only has an inner wall 722. The spade 718 does not have an outer wall that goes around the wall of the needle shield. The inner wall 722 includes a barb 726 that engages the needle shield when the clip 710 is assembled. Although only a single barb 726 is illustrated, another barb is contemplated on the other side of the second leg 714. A spring force in the clip 710 applies a force to secure the barb 726 of the spade 718 to the needle shield. This clip 710 configuration advantageously provides a narrower design because the clip 710 does not wrap around the outside of the needle shield. Accordingly, this design may also improve assembly.

The clip 710 also includes a flag 728. The flag 728 is directly connected to the first leg 712 and the foot 732. This clip 710 design advantageously improves the stamping operation during manufacturing by creating a more compact design and reducing the amount of scrap.

Figure 57:
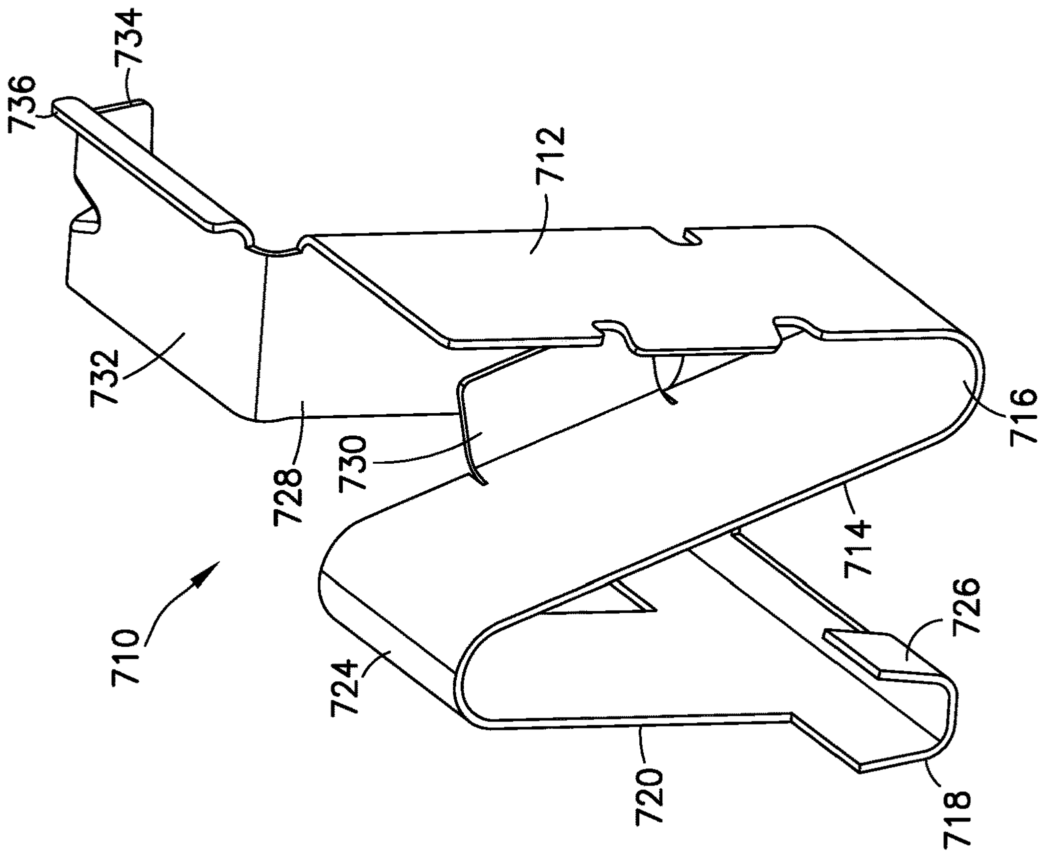
FIG. 57 illustrates a right perspective view of an alternate embodiment of the V-shaped metal clip of the catheter assembly.
Figure 58:
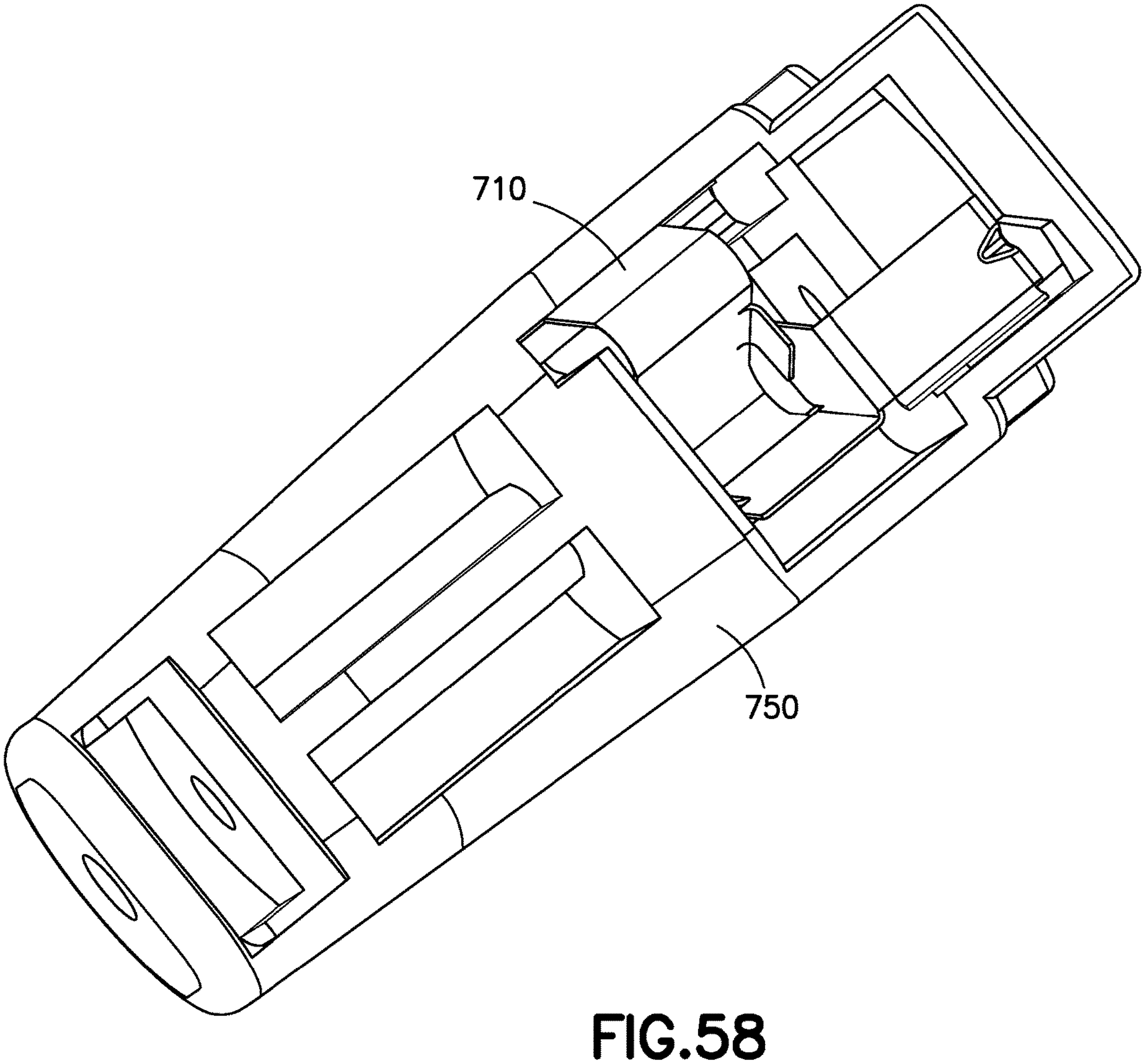
FIG. 58 illustrates a right perspective view of the V-shaped metal clip of FIG. 57 inserted into a needle shield.

FIGS. 57 and 58 illustrate an alternate embodiment of a clip 710 including a spade 718 disposed on a top surface of the outer wall 720. The spade 718 includes an outer wall 720 and barbs 726 to secure the clip 710 to the needle shield 750. The outer wall 720 is connected to the second leg 714 via the bottom portion 724 of the spade 718. This configuration of the clip 710 includes long spring legs for both the first and second legs 712, 714. The long spring legs provide the advantages of reduced stress and increased flexibility as described above.

Figure 60:
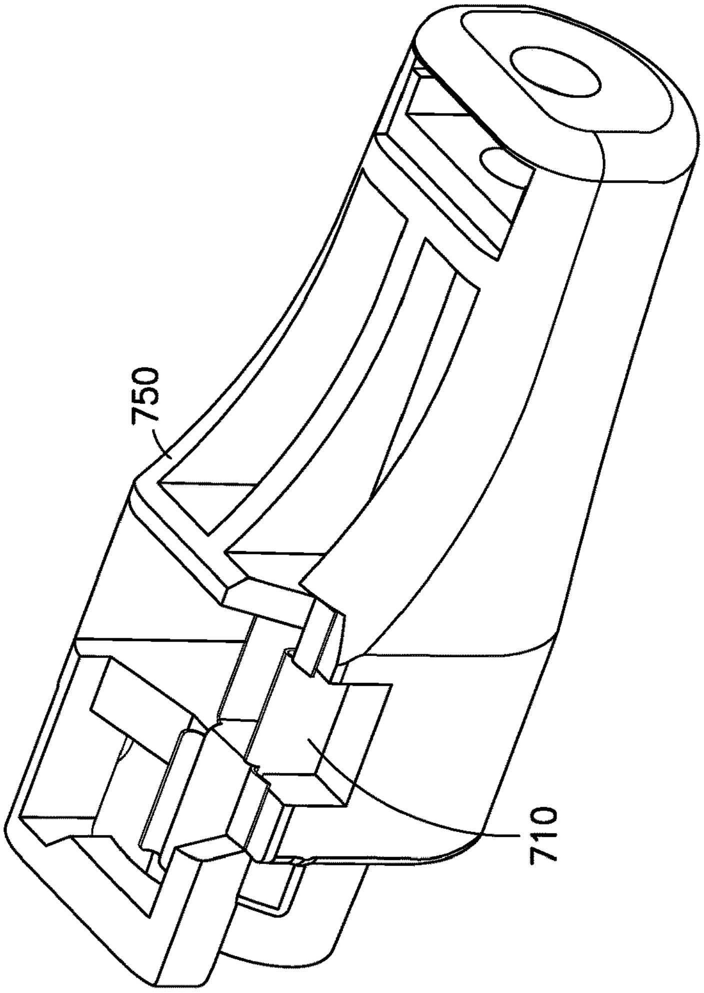
FIG. 60 illustrates a left perspective view of the V-shaped metal clip of FIG. 59 inserted into a needle shield.
Figure 59:
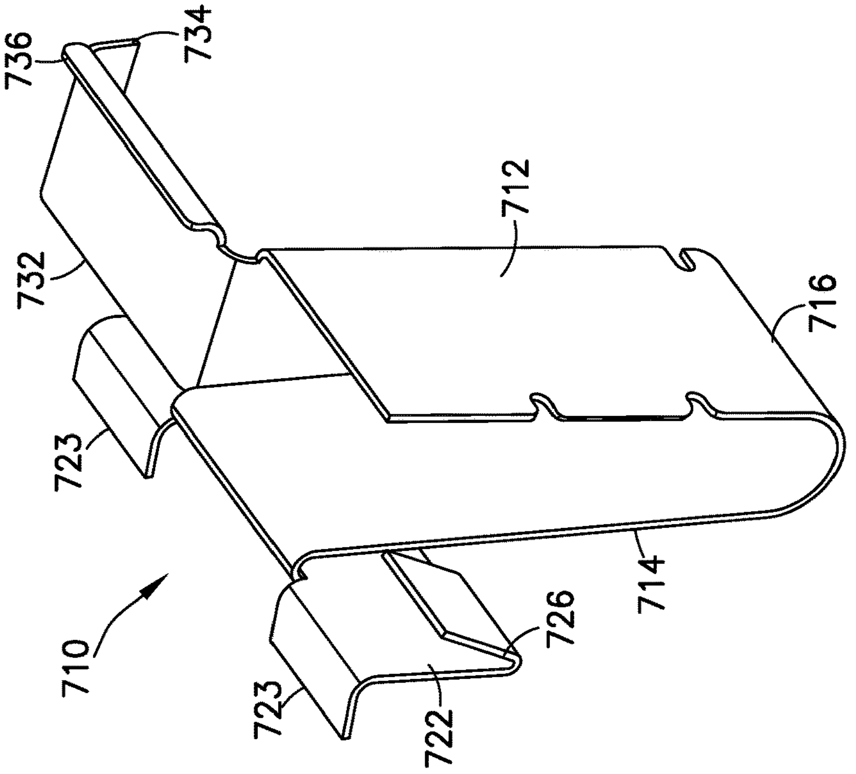
FIG. 59 illustrates a right perspective view of an alternate embodiment of the V-shaped metal clip of the catheter assembly.

FIGS. 59 and 60 illustrate an alternate embodiment of a clip 710 that does not have a spade to mount to the needle shield 50. Instead, the second leg 714 bends approximately 180 degrees (corresponds to a folded surface) at a bottom surface to form a ledge 723 on both sides of the second leg 714, an inner wall 722 and barbs 726 (on both sides, not illustrated).

When the clip 710 is assembled, the ledge 723 is disposed on a bottom surface of the needle shield 750. The inner wall 722 and barbs 726 engage an inner cavity of the needle shield 750 to secure the clip 710. This configuration allows the second leg 714 to have a longer length to achieve the advantages described above. However, the 180 degree bend can create high stress during manufacturing and in operation.

Figure 61:
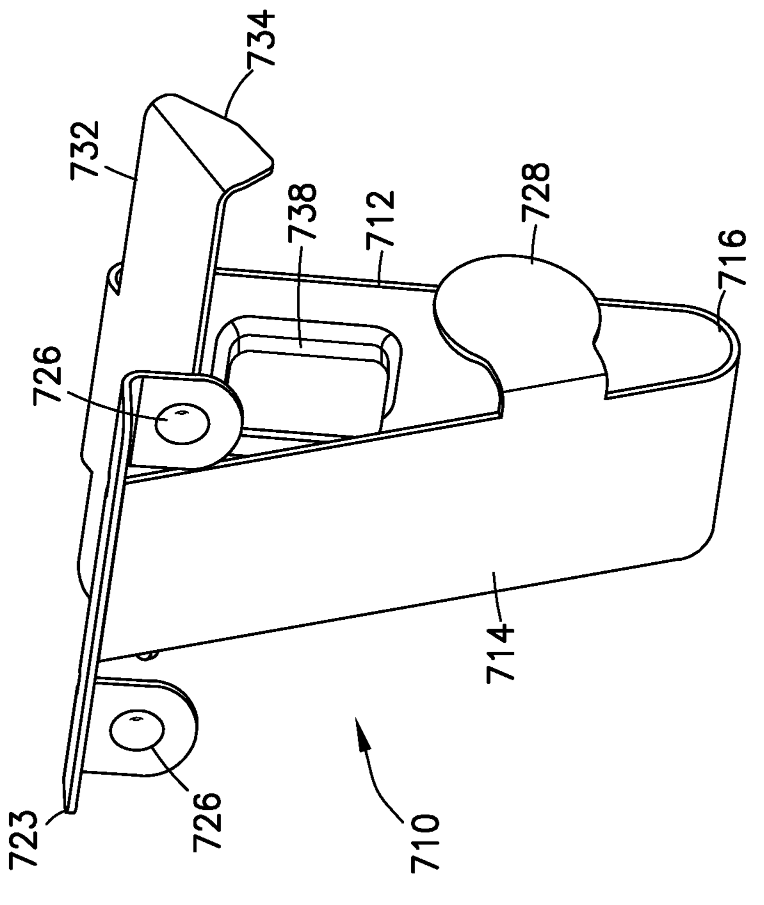
FIG. 61 illustrates a left, rear perspective view of an alternate embodiment of the V-shaped metal clip of the catheter assembly.

FIGS. 61-65 illustrate an alternate embodiment of a clip 710 in the needle shield 750. FIG. 61 illustrates the clip 710 including a long second leg 714 with a bend at a lowermost portion to form a ledge 723. The second leg 714 includes similar benefits as described above with respect to its extended length. Additionally, the clip 710 includes a mounting cavity 738 to engage and secure the clip 710 to the needle shield (as further described below).

Figure 62:
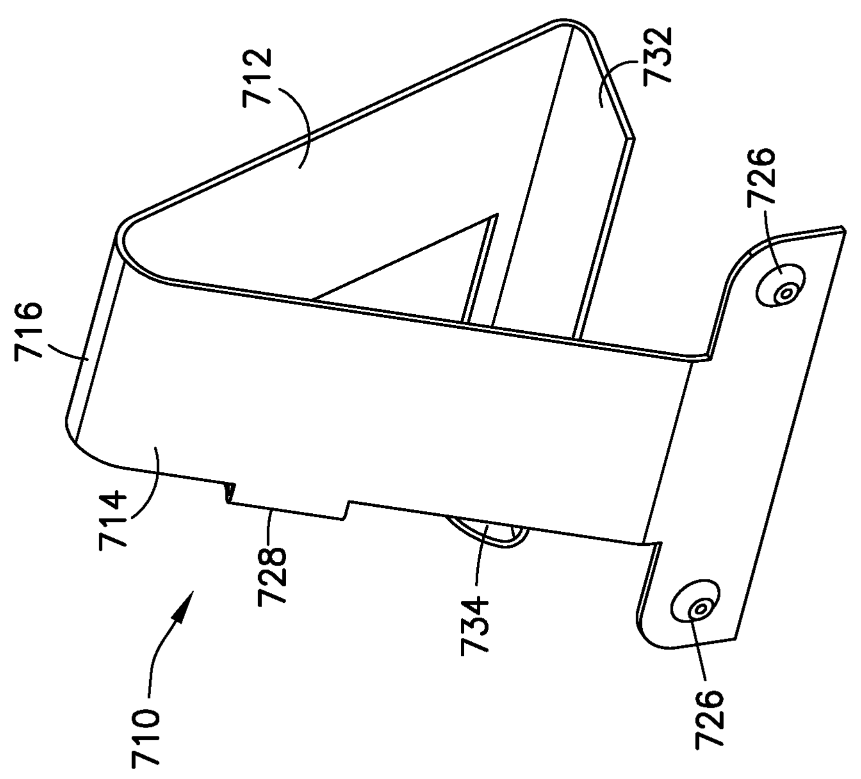
FIG. 62 illustrates a left, bottom perspective view of the V-shaped metal clip of FIG. 61 of the catheter assembly.

FIGS. 61 and 62 illustrate a foot 732 and a latch 734 on a bottom portion of the clip 710. A flag 728 is directly connected to the second leg 714. The clip 710 further includes barbs 726 attached to the ledge 723 at approximately a 90 degrees angle. The barbs 726 secure the clip 710 to the needle shield 750 (as further described below).

Figure 63:
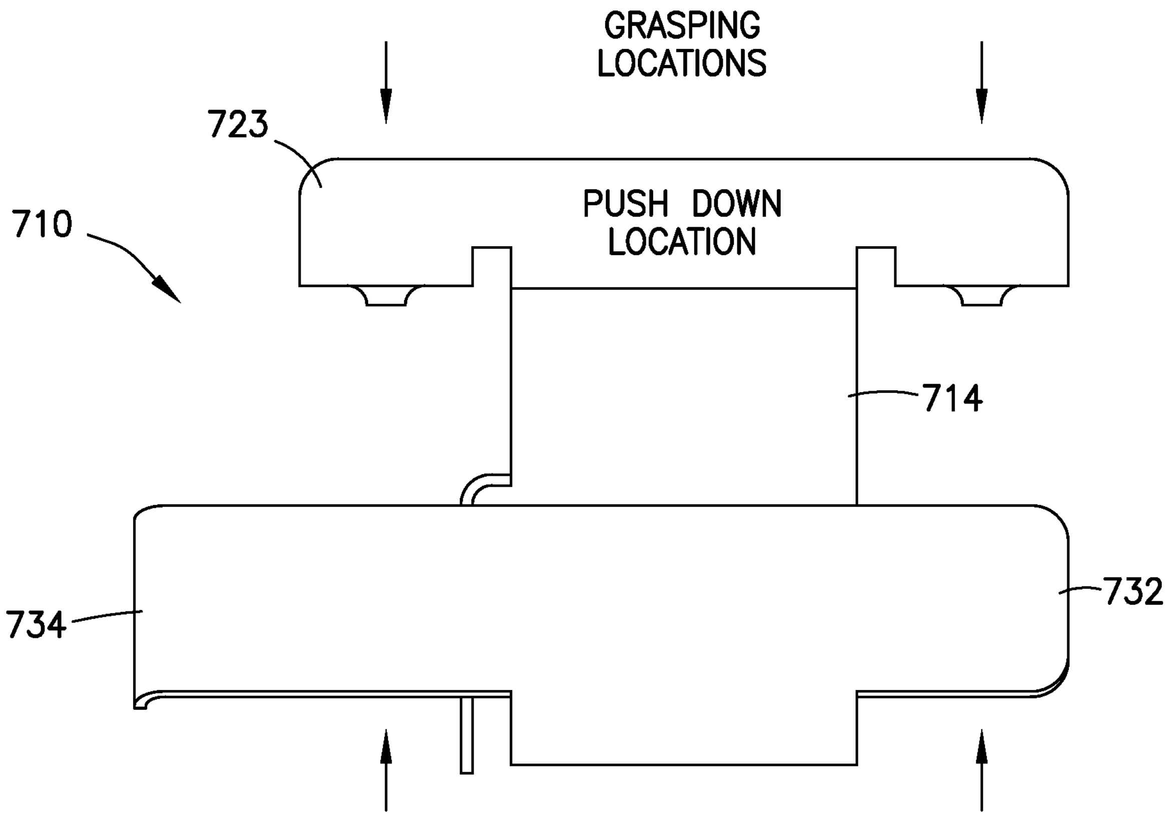
FIG. 63 illustrates a top view of the V-shaped metal clip of FIG. 61 of the catheter assembly.

FIG. 63 illustrates a top view of the clip 710 that shows how the clip 710 is assembled into the needle shield. Specifically, the user applies pressure to outside surfaces of the first and second legs 712, 714 to compress them toward each other. More specifically, the user can hold the clip 710 at an outer surface of the foot 732 and an outer surface of the ledge 723 (see arrows indicating grasping locations) and pull these two surfaces together to initiate assembly. Such a configuration aids in the assembly of the clip 710 into the needle shield.

Figure 64:
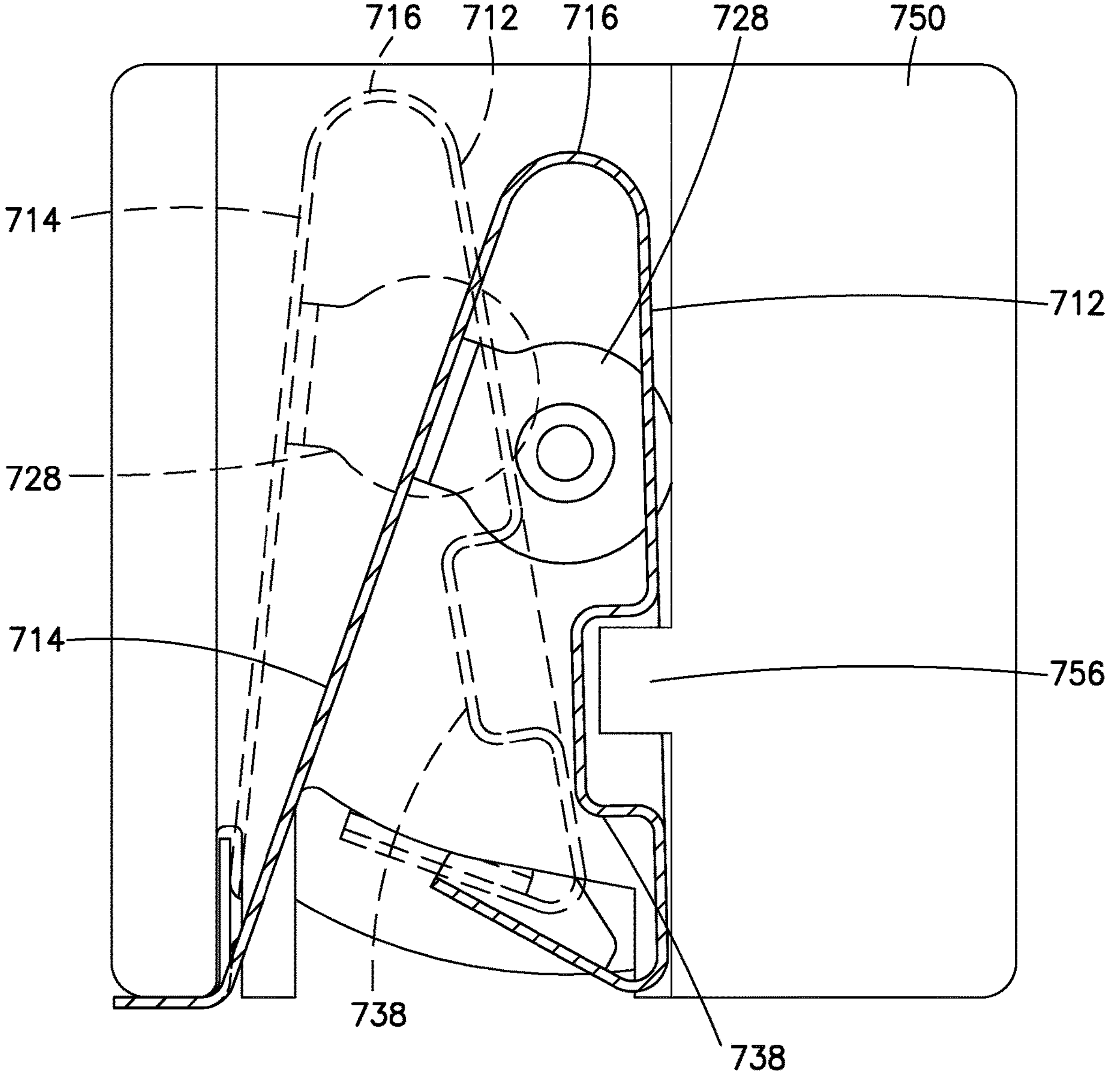
FIG. 64 illustrates a side cross sectional view of the V-shaped metal clip of FIG. 61 in a first and second state disposed in a needle shield.

FIG. 64 illustrates the clip 710 mounted into the needle shield 750. The clip 710 is illustrated in two states. The first state is the compressed state, where the clip 710 is compressed to aid assembly into the needle shield 750. Additionally, the first state illustrates the condition where the needle of the needle shield 750 is in operation. During operation, the first leg 712 contacts the needle (not shown). In the first state, the mounting cavity 738 is not engaged to the mounting protrusion 756 of the needle shield 750.

In the second state, when the needle is retracted and the needle tip enters into the needle shield 750, the needle no longer contacts the first leg 712 (not shown) and the clip 710 is released. As a result, the mounting cavity 738 of the clip 710 engages a mounting protrusion 756 in the needle shield 750. Additionally, the flag 728 blocks the needle from exiting the needle shield 750.

Accordingly, the engagement between the mounting cavity 738 and the mounting protrusion 756 advantageously prevents the clip 710 from being accidentally released from the needle shield 750. The engagement also advantageously prevents undesired movement of the clip 710 in the needle shield 750 and tampering of the clip 710 by an unauthorized person.

Figure 65:
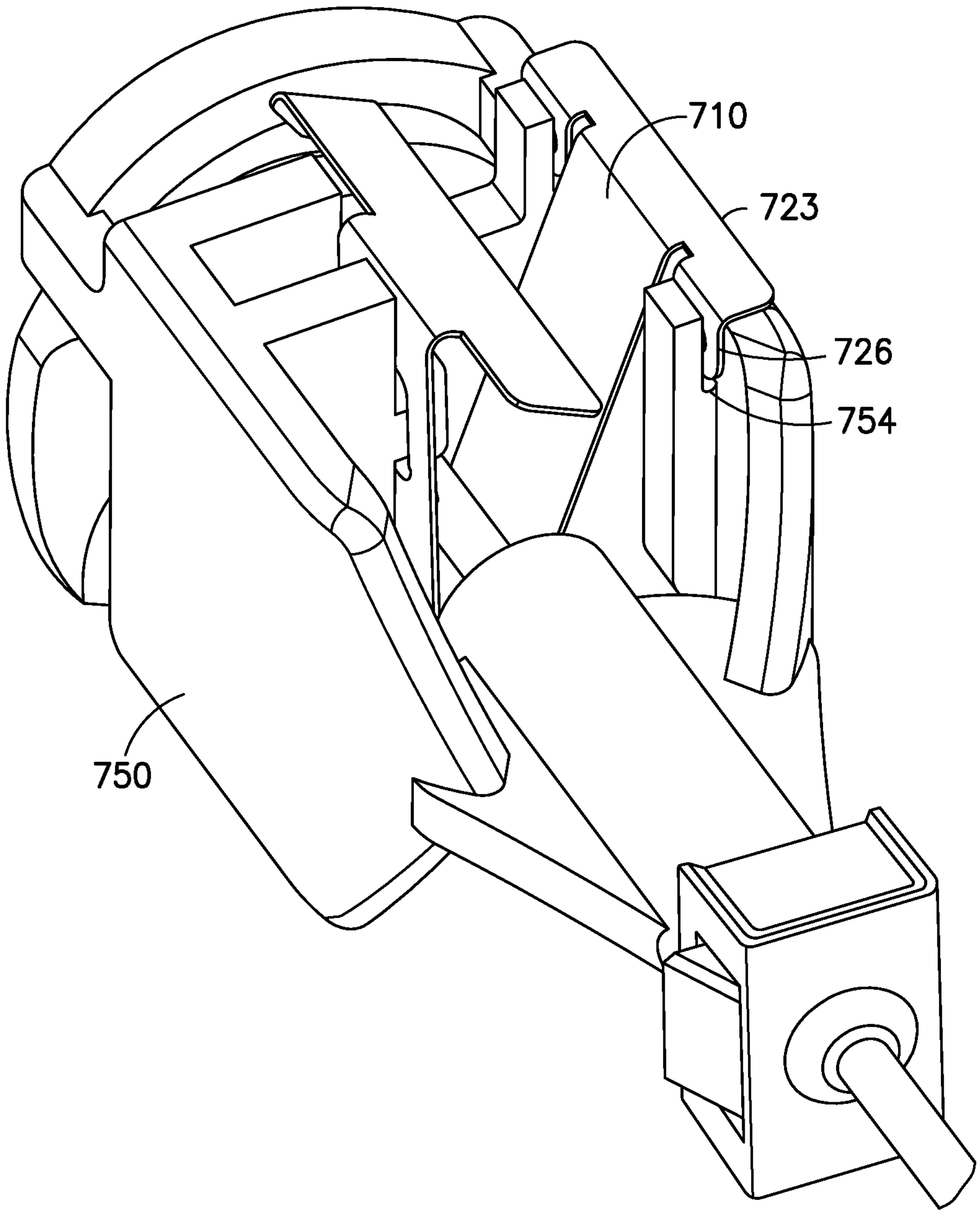
FIG. 65 illustrates a left, rear perspective view of the V-shaped metal clip of FIG. 61 inserted into a needle shield.

FIG. 65 illustrates the clip 710 assembled in the needle shield 750. The needle shield 750 includes a housing slot 754 that receives the barbs 726 of the clip 710. The ledge 723 is disposed on a bottom surface of the needle shield 750. Engagement of the barbs 726 in the housing slot 754 advantageously prevents the clip 710 from moving upward and exiting the needle shield 750. Additionally, the barbs 726 of the clip 710 replace the need for a spade that goes around the outer wall of the needle shield 750 to secure the clip 710. Accordingly, the width of the clip 710 and the needle shield assembly is reduced.

Figure 66:
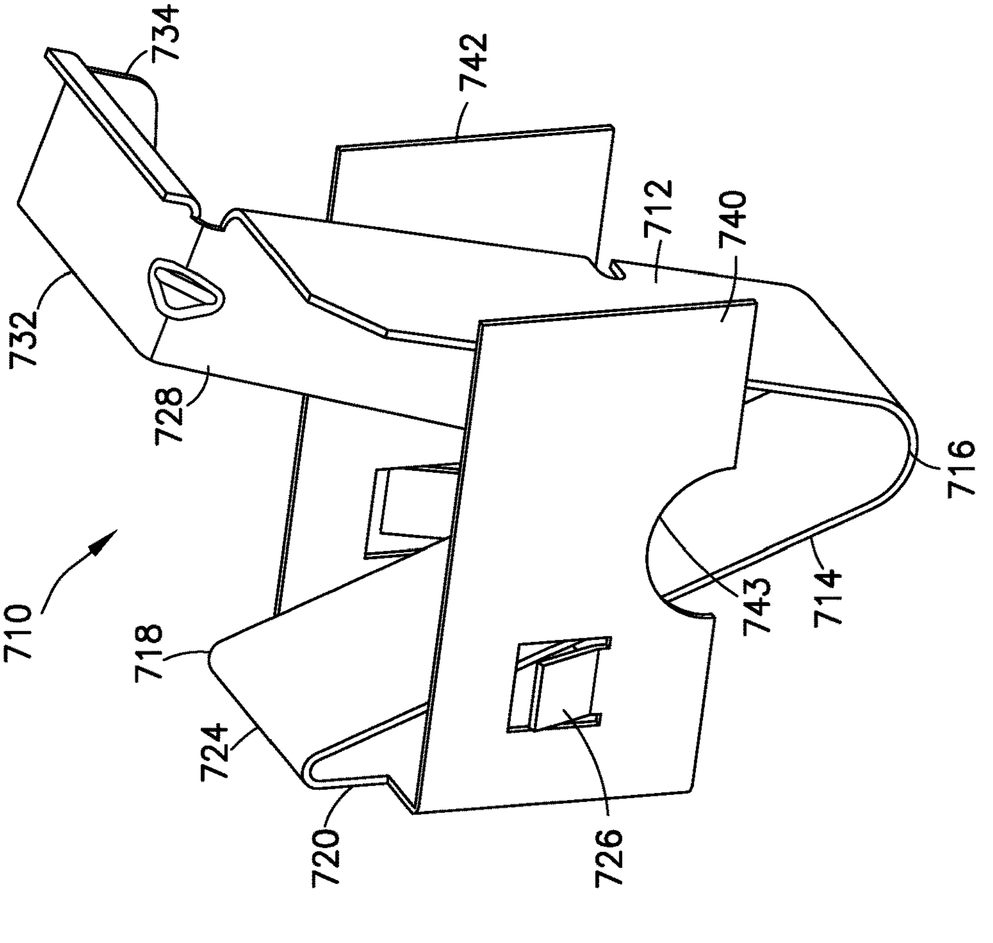
FIG. 66 illustrates a right perspective view of an alternate embodiment of the V-shaped metal clip of the catheter assembly.

FIG. 66 illustrates an alternate embodiment of a clip 710 including a front wall 742 and a rear wall 740. The front and rear walls 742, 740 are perpendicular to a longitudinal axis of a needle in the needle shield (not shown). Specifically, an outer wall 720 of the spade 718 is bent approximately 90 degrees inward on each side of the second leg 714 toward the longitudinal axis of the needle. The front and rear walls 742, 740 includes holes 743 to allow the needle to pass through during operation. Barbs 726 are disposed on each of the rear and front walls 740, 742 for appropriate mounting into the needle shield.

Figure 67:
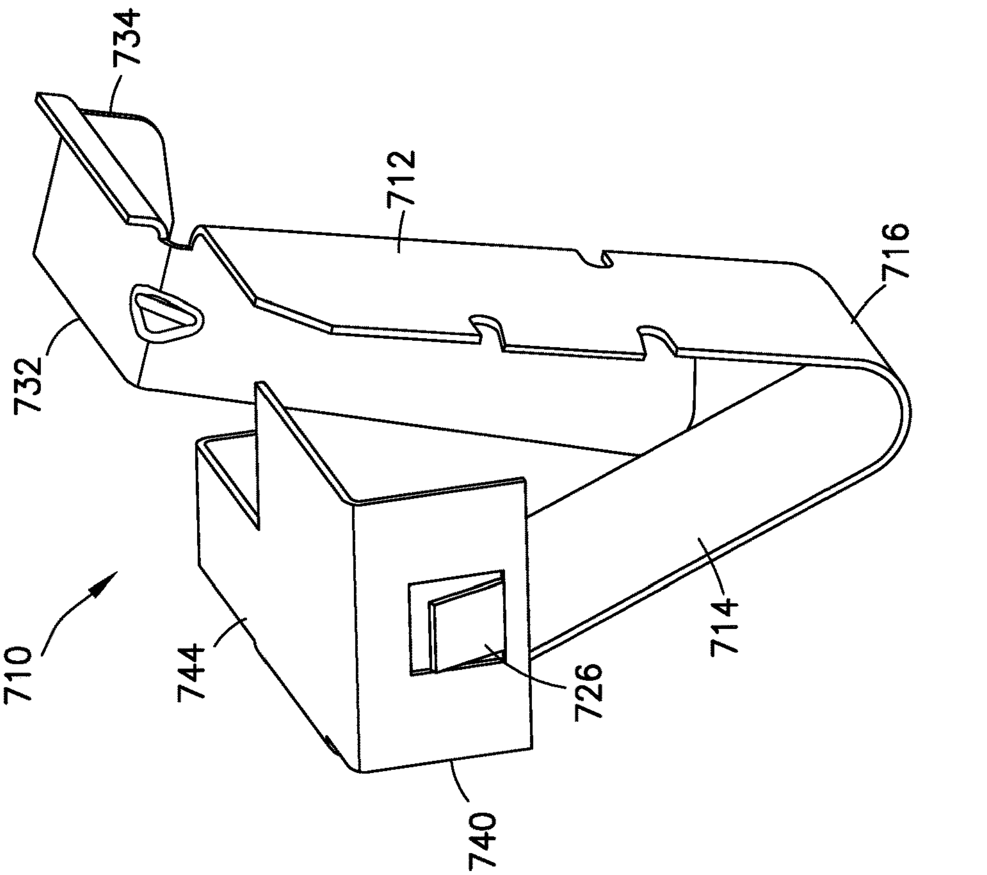
FIG. 67 illustrates a right perspective view of an alternate embodiment of the V-shaped metal clip of the catheter assembly.

FIG. 67 illustrates an alternate embodiment of a clip 710 similar to the embodiment of FIG. 66. The clip 710 includes a rear wall 740 but does not include a front wall 742. Specifically, an upper portion of the second leg 714 is bent inward at approximately 80 degrees into a top wall 744. The rear end of the top wall 744 is bent downwardly at approximately 90 degrees to form a rear wall 740. A barb 726 is disposed on the rear wall 740 to securely mount to the needle shield.

Figure 68:
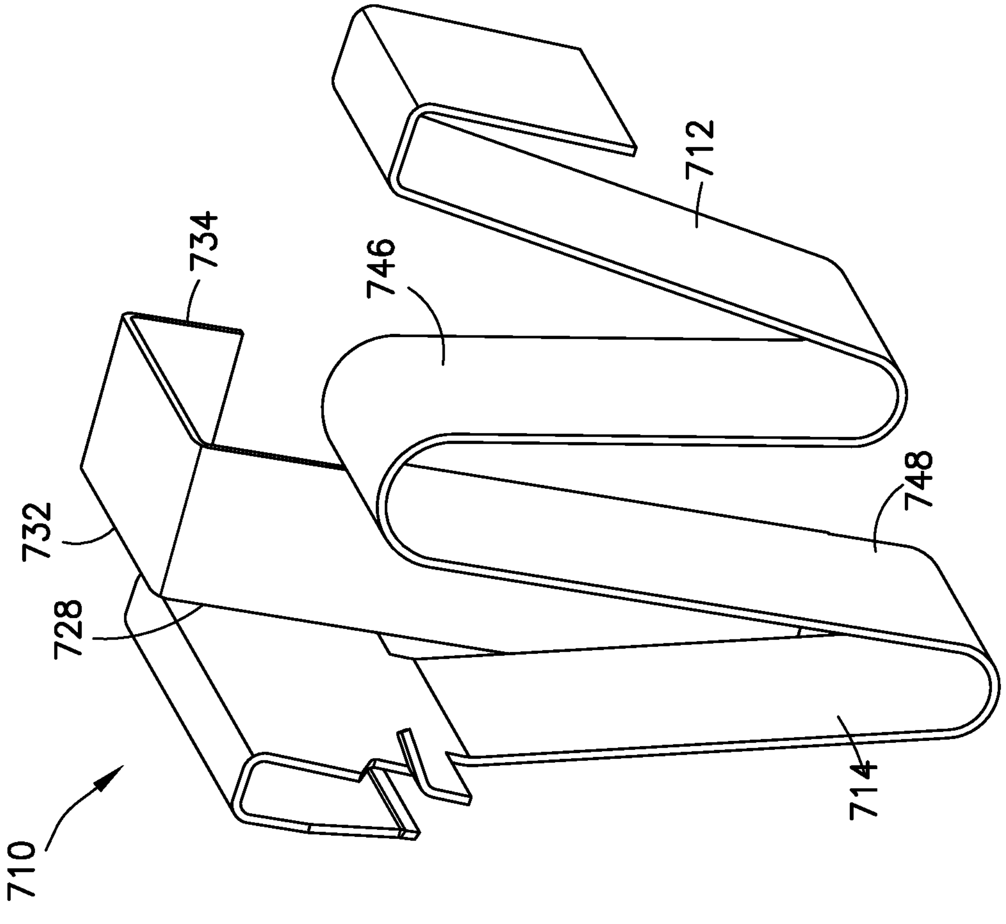
FIG. 68 illustrates a right perspective view of an alternate embodiment of the V-shaped metal clip of the catheter assembly.

FIG. 68 illustrates an alternate embodiment of a clip 710 that acts as an extension spring instead of a compression spring. In all of the other embodiments of the clip described herein, the needle compresses the clip during operation (like a compression spring). When the needle is removed and enters into the needle shield, the clip releases and blocks the needle from exiting (release of the compression spring).

According to this embodiment, however, the clip 710 includes a first intermediate leg 746 and a second intermediate leg 748 disposed between the first leg 712 and the second leg 714. The first and second legs 712, 714 are attached to opposing surfaces of the needle shield.

When the needle is in operation, the needle contacts the second intermediate leg 748 causing the clip 710 to be in an extended position. Such a position causes the second intermediate leg 748 to act as an extension spring. Specifically, the second intermediate leg 748 naturally tends to move toward the first leg 712 but the needle prevents that from occurring.

When the needle is retracted into the needle shield, the second intermediate leg 748 is released and moves toward the first leg 712 (the extension spring returns to a normal position). Accordingly, the flag 728 moves in front of the needle and blocks the needle from exiting the needle shield.

Figure 69:
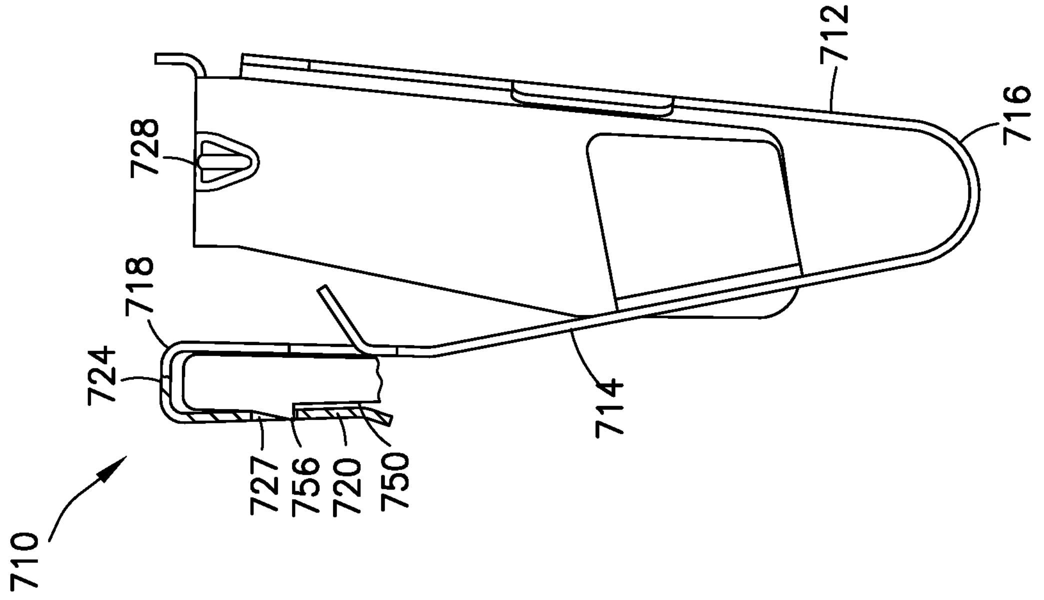
FIG. 69 illustrates a front cross sectional view of an alternate embodiment of the V-shaped metal clip of the catheter assembly.

FIG. 69 illustrates an alternate embodiment of a clip 710 including an outer wall 720 of the spade 718 having an opening 727. The opening 727 receives a mounting protrusion 756 of the needle shield 750 when the clip 710 is assembled. Such a configuration advantageously provides another simple manner to mount and secure the clip 710 to the needle shield 750.

According to an alternate embodiment of the clip 710 of FIG. 69, the outer wall 720 can include two barbs disposed perpendicular and extending away from the outer wall 720. The two barbs pinch or latch onto an inner rib or an inner wall of the needle shield. Such a feature advantageously allows the clip 710 to be reliably retained while minimizing the overall width of the clip 710.

Figure 70:
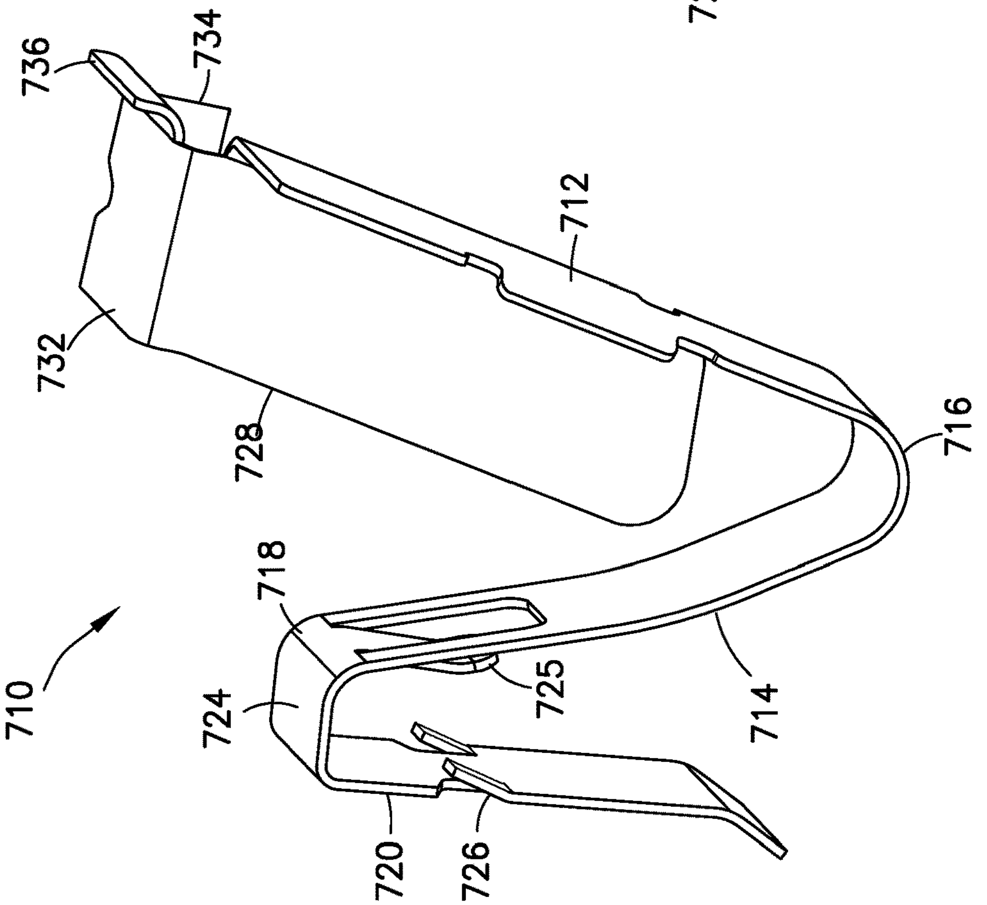
FIG. 70 illustrates a right perspective view of an alternate embodiment of the V-shaped metal clip of the catheter assembly.

FIG. 70 illustrates an alternate embodiment of a clip 710 including a modified spade 718. Specifically, the spade 718 includes an outer wall 720 with barbs 726 and an inner wall 722 with a flap 725. The barbs 726 and flap 725 can also respectively be switched and disposed on opposite walls 720, 722 of the spade 718. When the clip 710 is mounted into the needle shield, the barbs 726 and the flap 725 each contact a side of a wall of the needle shield to secure the clip 710. In other words, the contact between the barbs 726 and the flap 725 pinch and fix the clip 710 to the needle shield.

Figure 71:
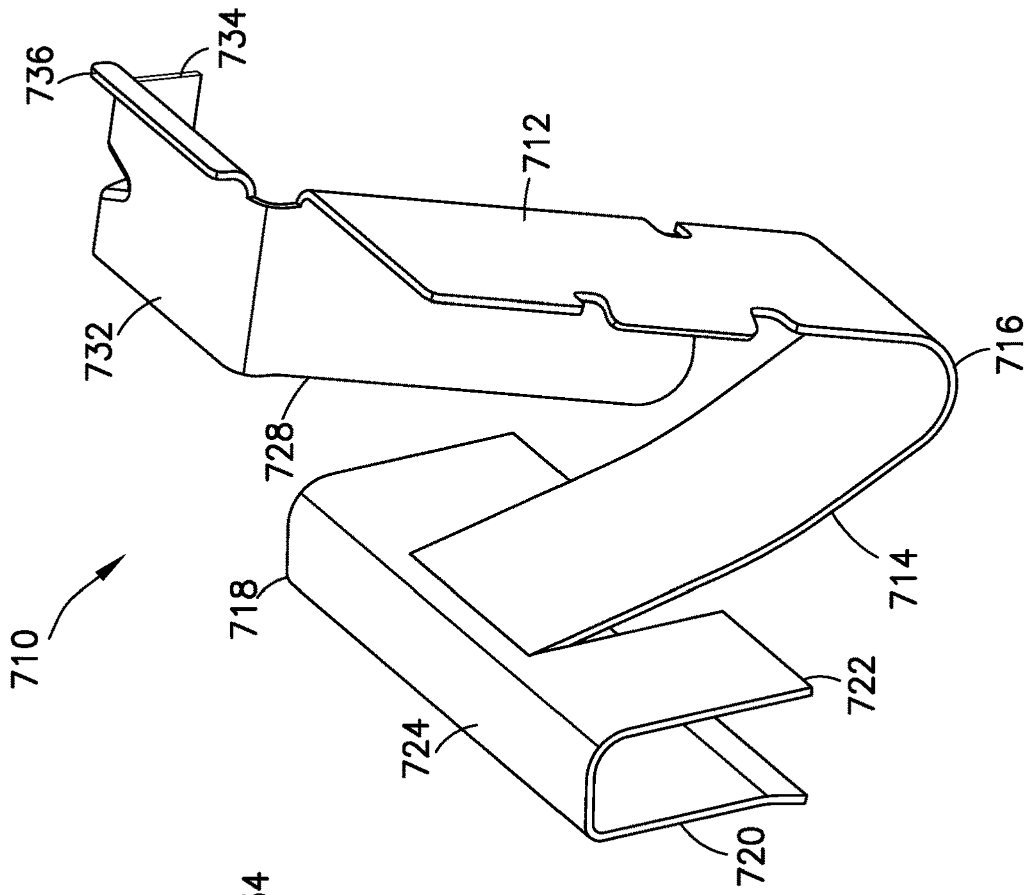
FIG. 71 illustrates a right perspective view of an alternate embodiment of the V-shaped metal clip of the catheter assembly.

FIG. 71 illustrates an alternate embodiment of a clip 710 similar to FIG. 70 where the outer and inner walls 720, 722 are extended in a widthwise direction of the clip 710.

Specifically, the outer and inner walls 720, 722 are extended beyond the width of the second leg 714 on both sides to advantageously provide a larger surface are to secure the clip 710. Although not illustrated, the outer and inner walls 720, 722 can include barbs 726 and flaps 725, as described in FIG. 70.

Figure 73:
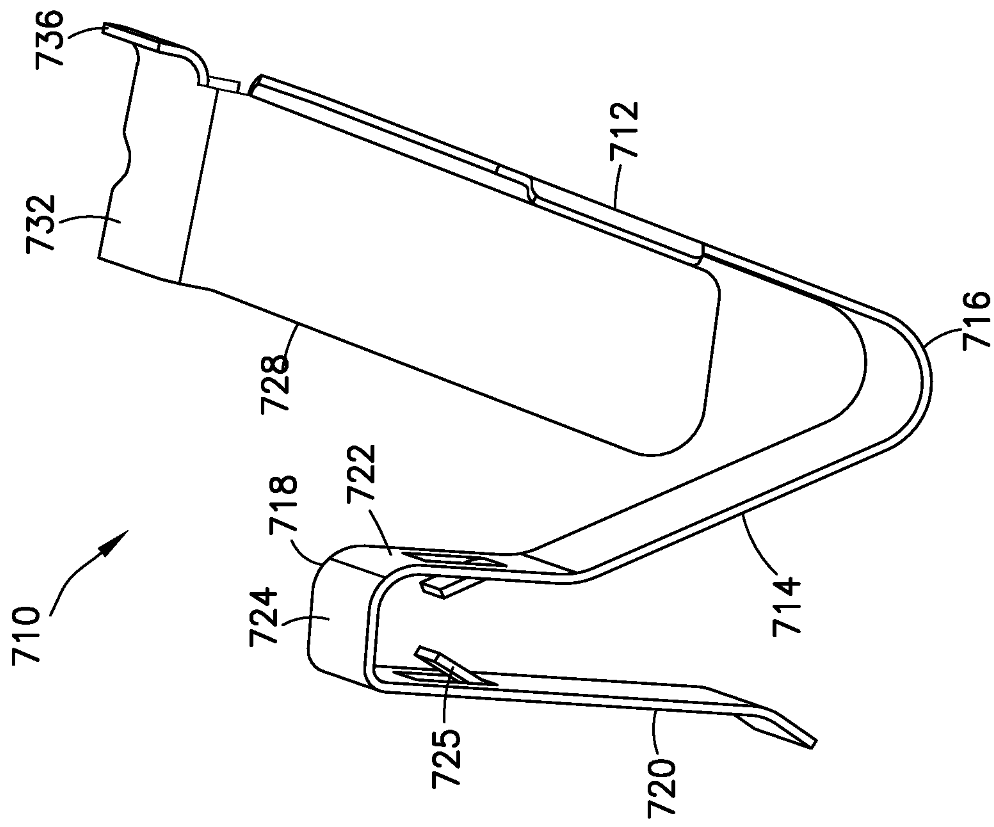
FIG. 73 illustrates another right perspective view of the V-shaped metal clip of FIG. 72 of the catheter assembly.
Figure 72:
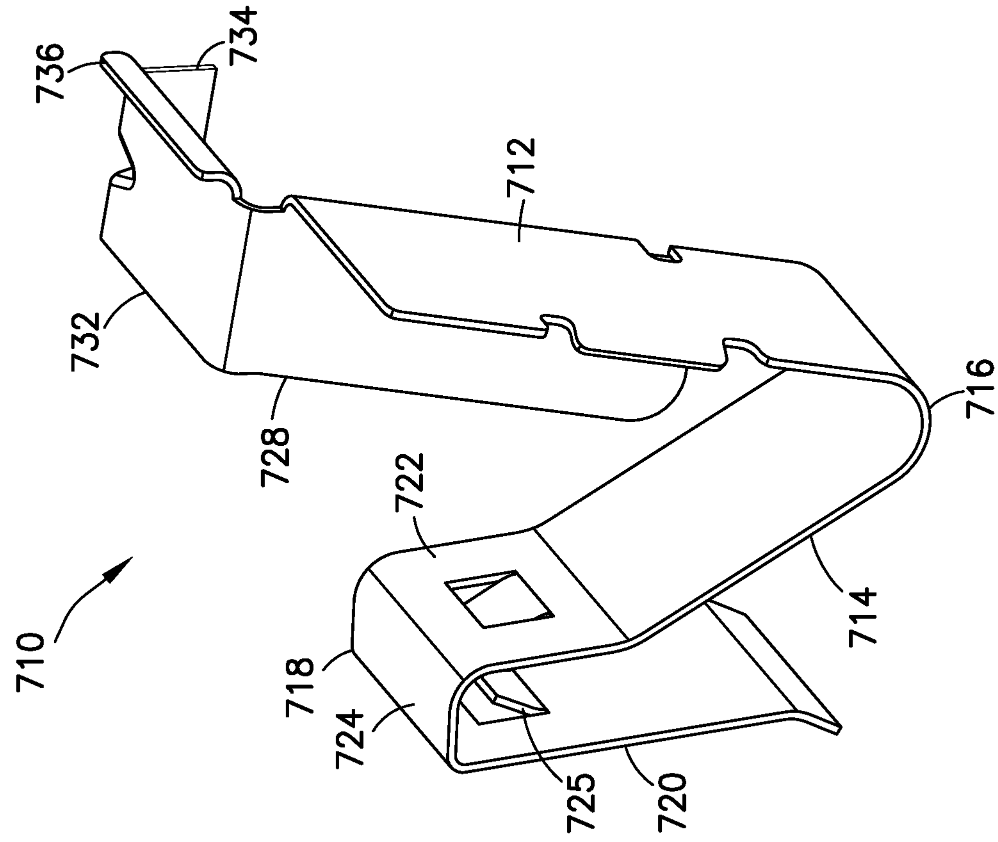
FIG. 72 illustrates a right perspective view of an alternate embodiment of the V-shaped metal clip of the catheter assembly.

FIGS. 72 and 73 illustrate an alternate embodiment of a clip 710 including a shorter second leg 714. A bend is disposed between the second leg 714 and the inner wall 722 of the spade 718 causing the second leg 714 to be shorter. As a result, the second leg 714 advantageously provides a stiffer and stronger clip 710.

Figure 74:
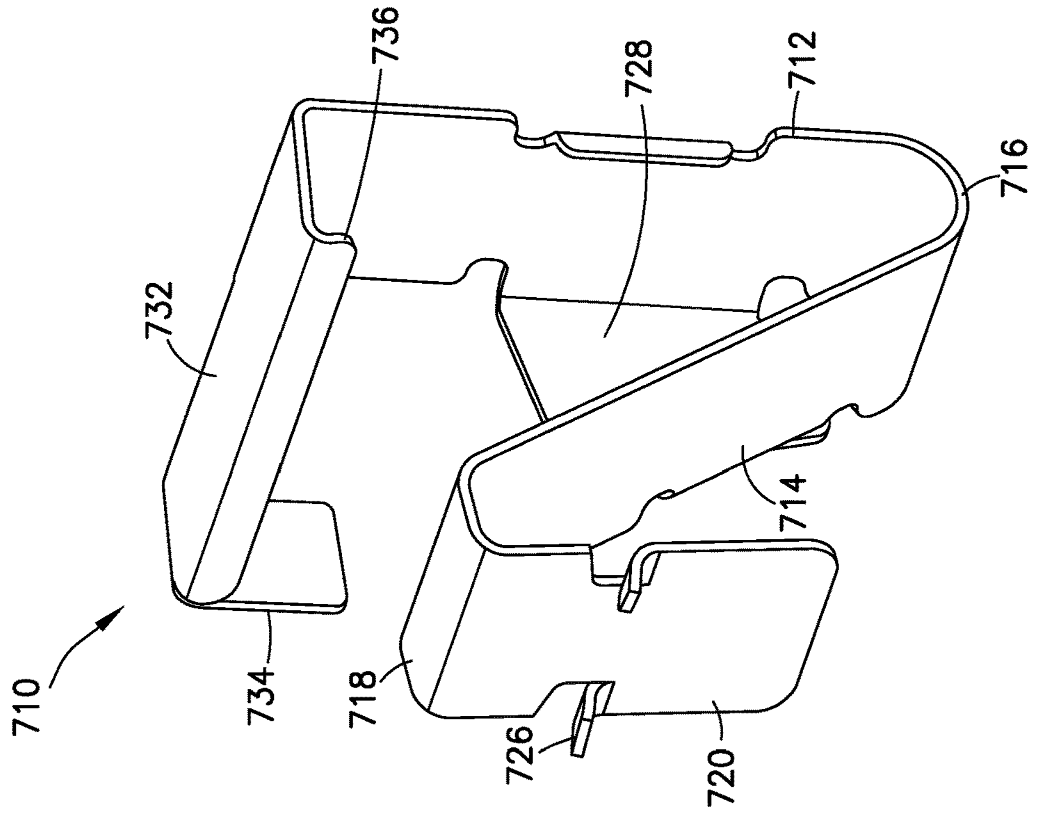
FIG. 74 illustrates a left perspective view of an alternate embodiment of the V-shaped metal clip of the catheter assembly.
Figure 77:
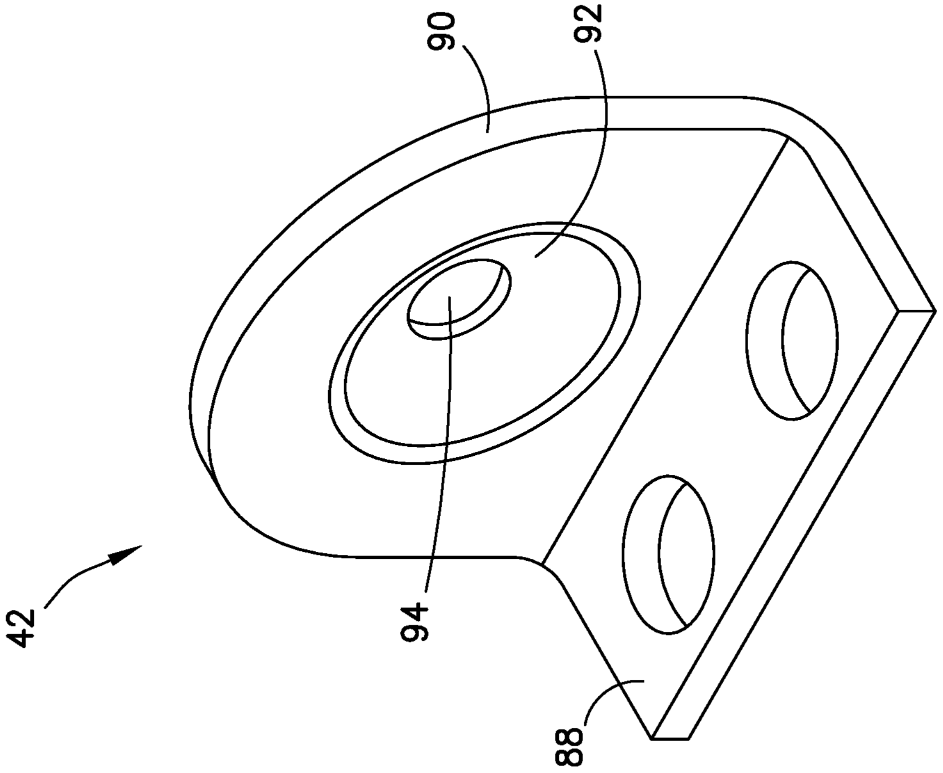
FIG. 77 illustrates a left perspective view of the washer of the catheter assembly.
Figure 76:
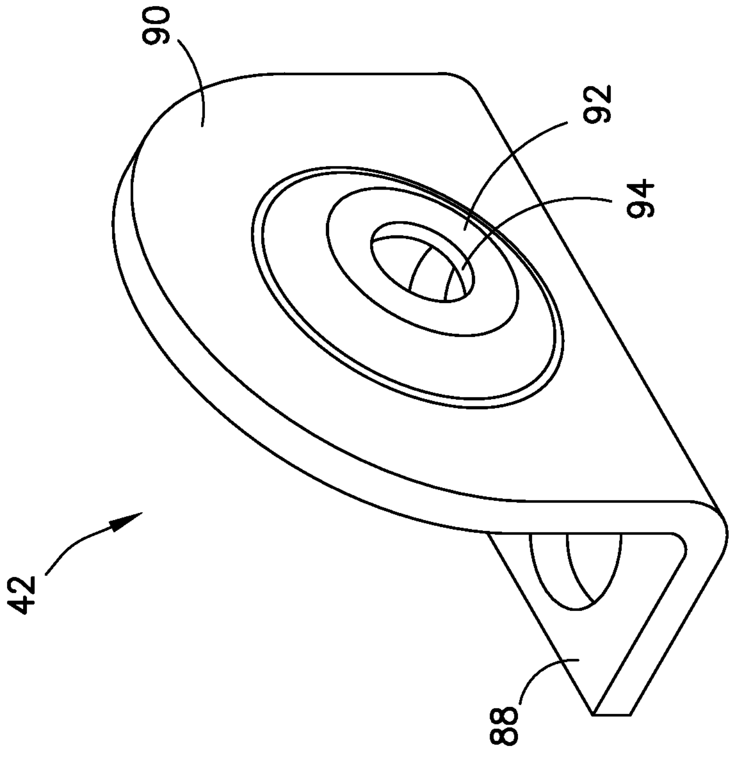
FIG. 76 illustrates a right perspective view of the washer of the catheter assembly.
Figure 78:
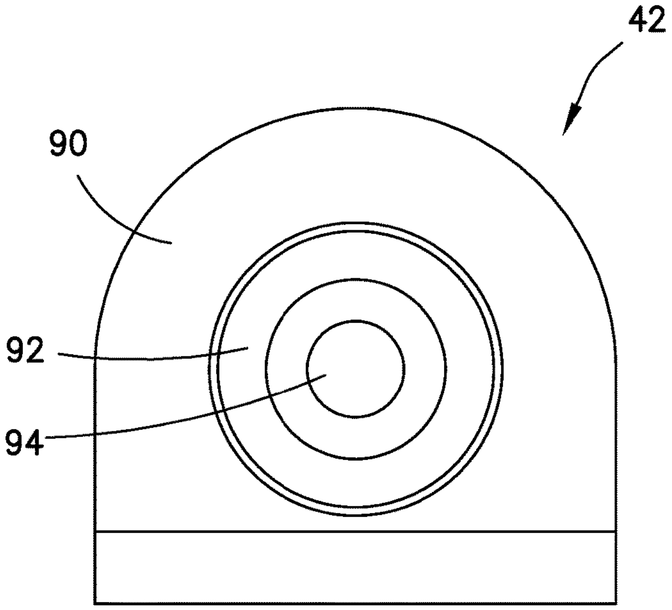
FIG. 78 illustrates a front elevation view of the washer of the catheter assembly.
Figure 79:
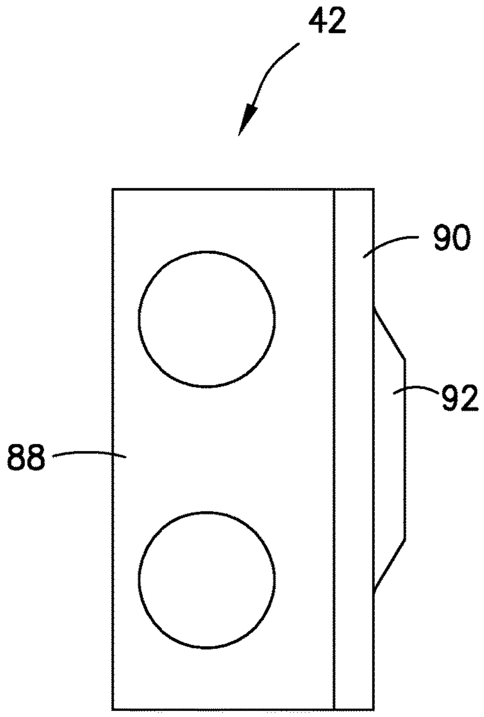
FIG. 79 illustrates a bottom plan view of the washer of the catheter assembly.
Figure 80:
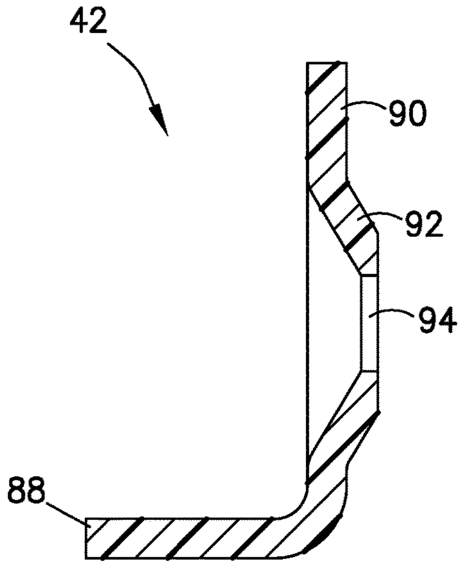
FIG. 80 illustrates a cross sectional view of a left side elevation view of the washer of the catheter assembly.
Figure 81:
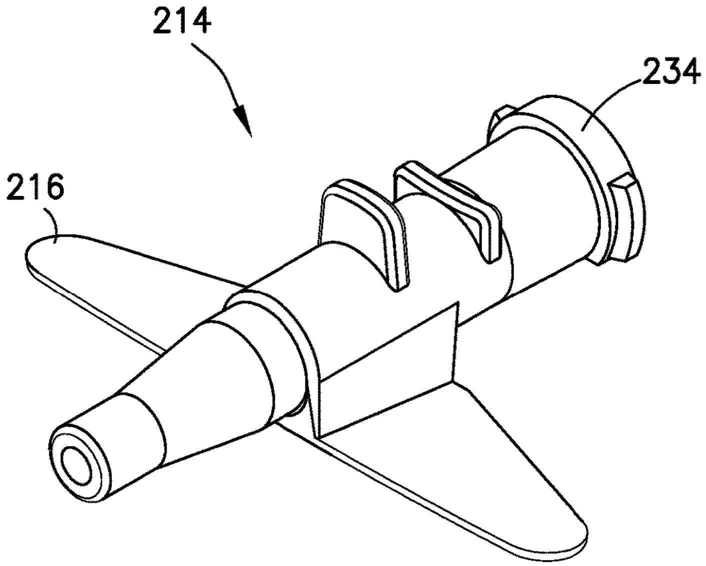
FIG. 81 illustrates a right perspective view of an alternative catheter hub with wings.
Figure 82:
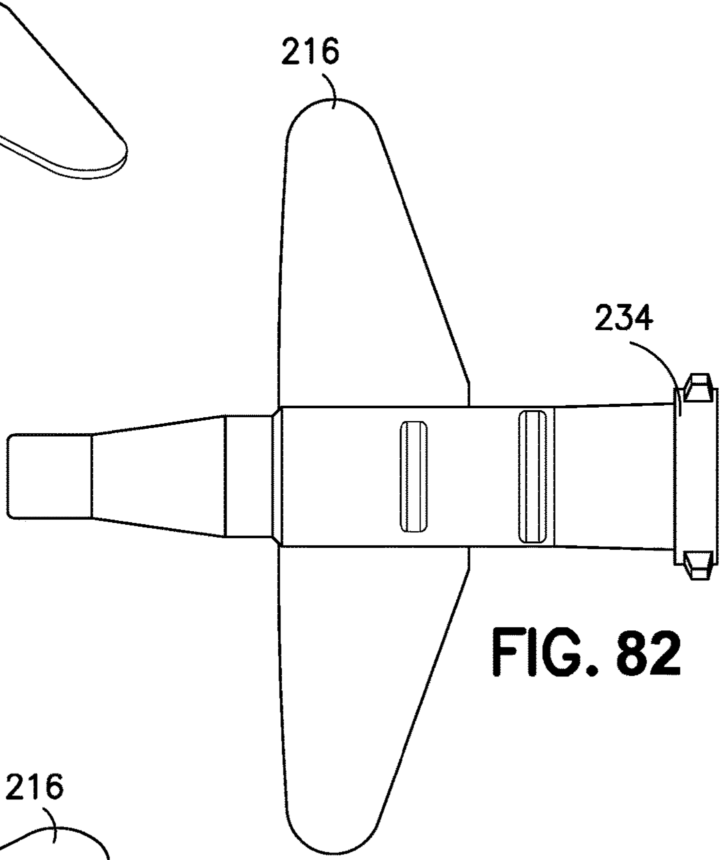
FIG. 82 illustrates a top plan view of the catheter hub with wings.
Figure 83:
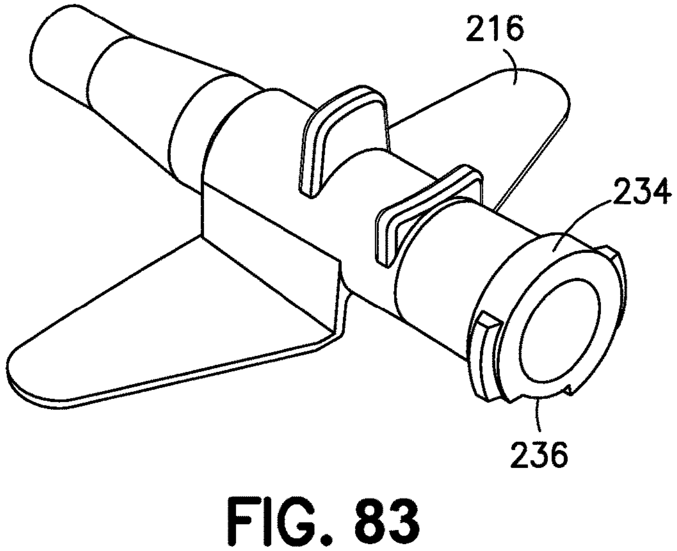
FIG. 83 illustrates a left perspective view of the catheter hub with wings.
Figure 84:
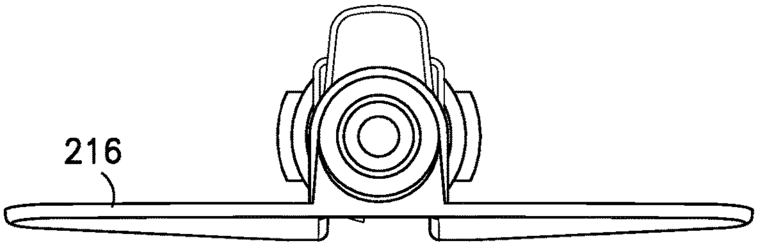
FIG. 84 illustrates a front view of the catheter hub with wings.
Figure 85:
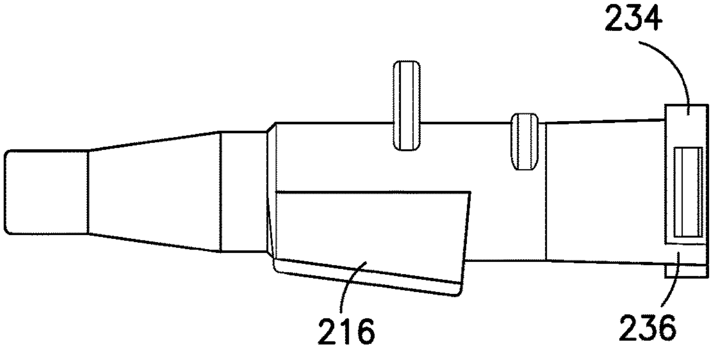
FIG. 85 illustrates a left side elevation view of the catheter hub with wings.
Figure 86:
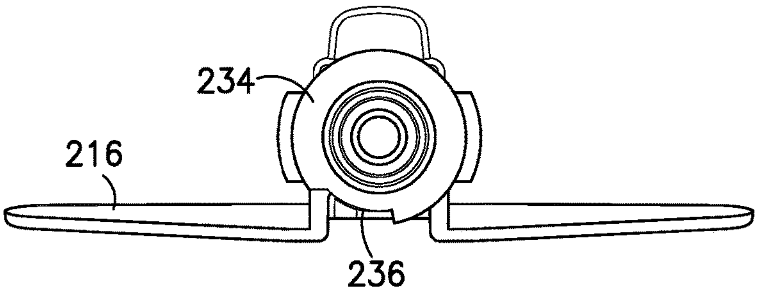
FIG. 86 illustrates a rear elevation view of the catheter hub with wings.
Figure 87:
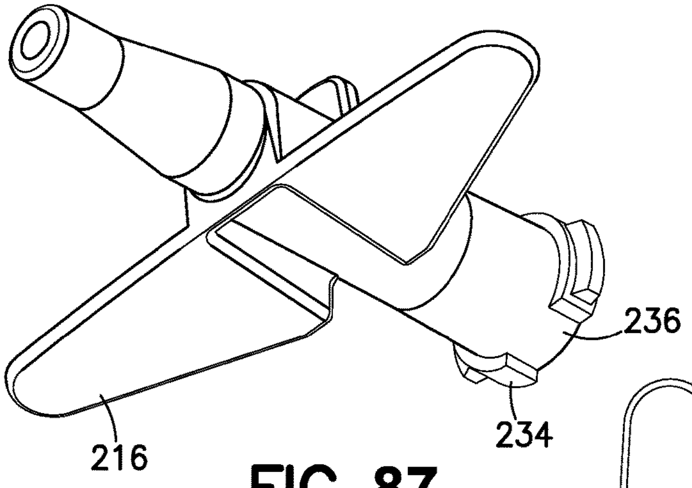
FIG. 87 illustrates a left perspective view of the catheter hub with wings.
Figure 88:
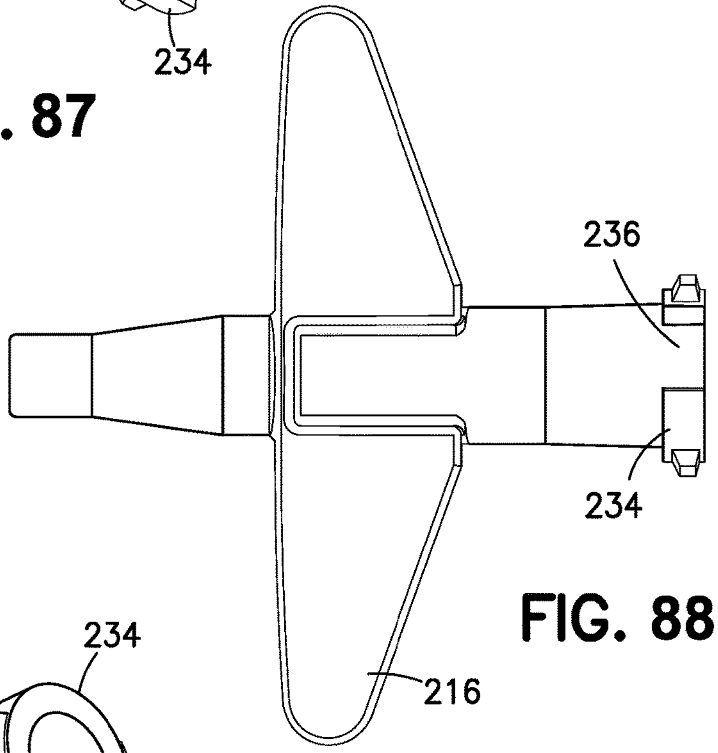
FIG. 88 illustrates a bottom plan view of the catheter hub with wings.
Figure 89:
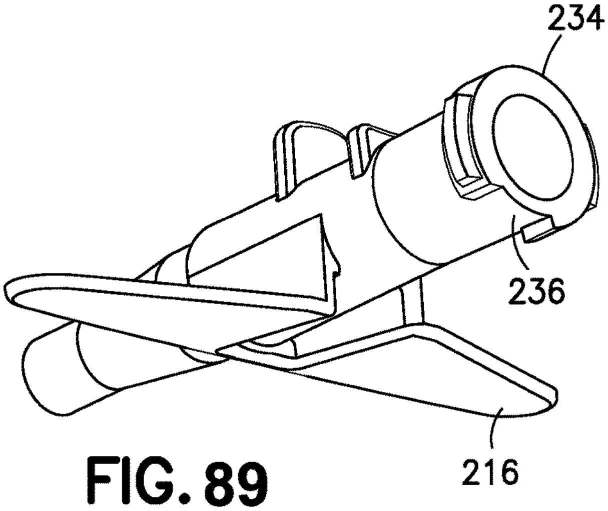
FIG. 89 illustrates a second right perspective view of the catheter hub with wings.
Figure 90:
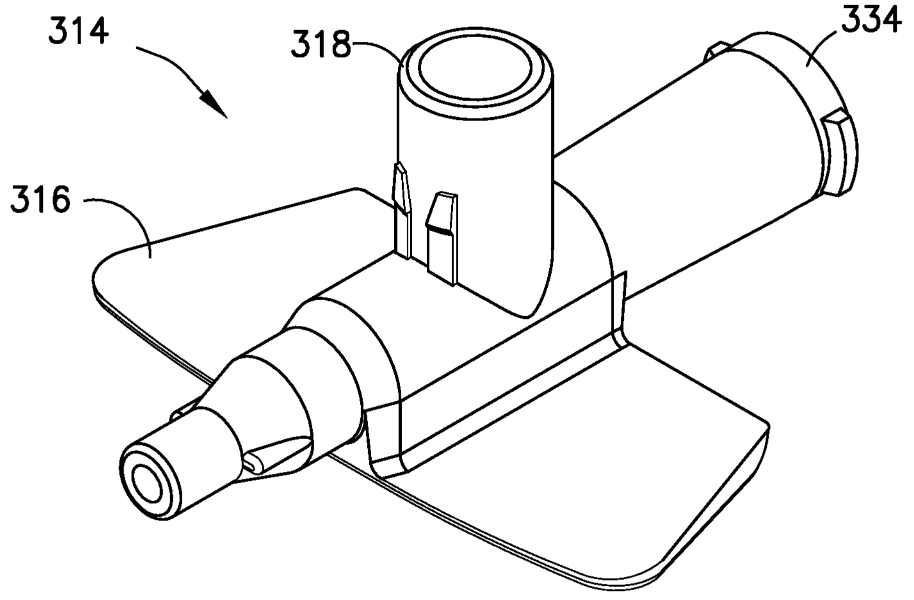
FIG. 90 illustrates a right perspective view of an alternative side port catheter hub.
Figure 91:
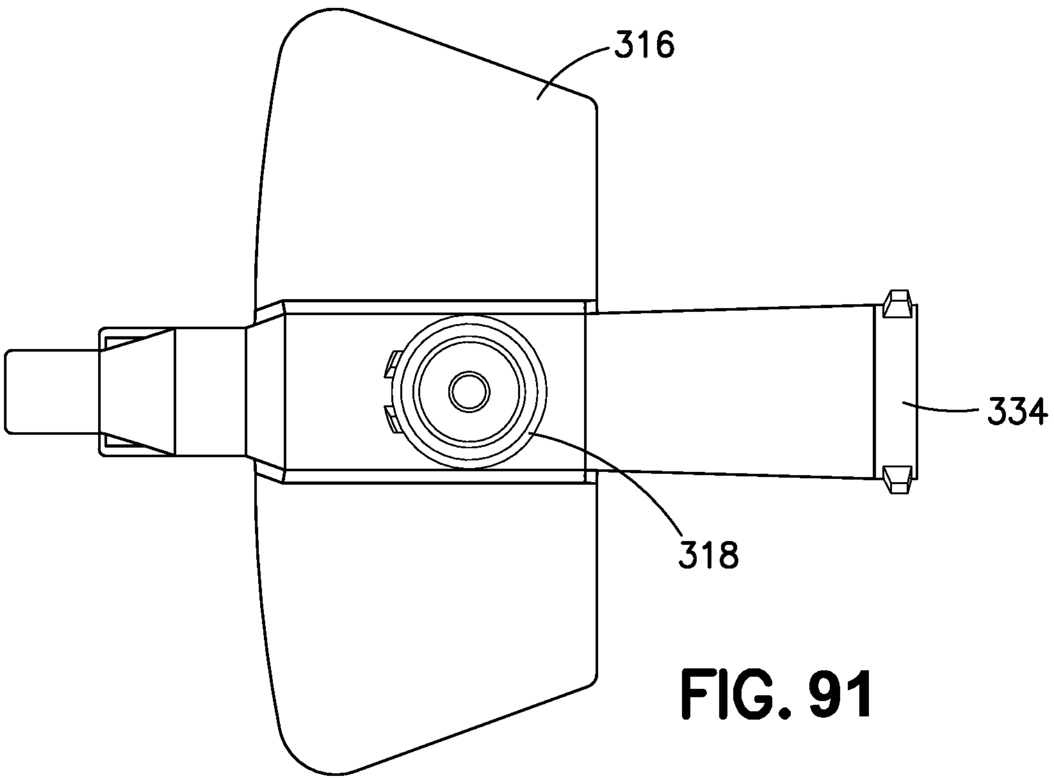
FIG. 91 illustrates a top plan view of the side port catheter hub.
Figure 92:
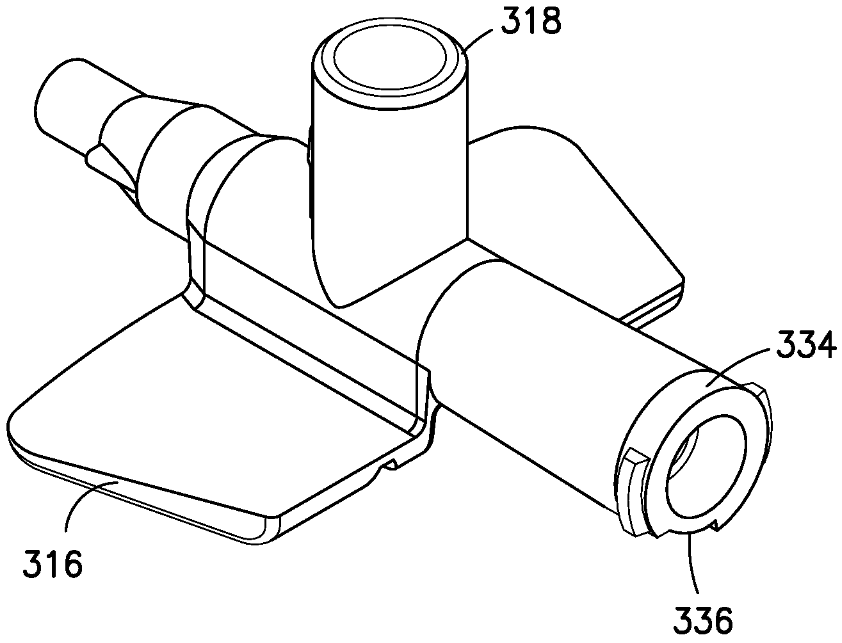
FIG. 92 illustrates a left perspective view of the side port catheter hub.
Figure 93:
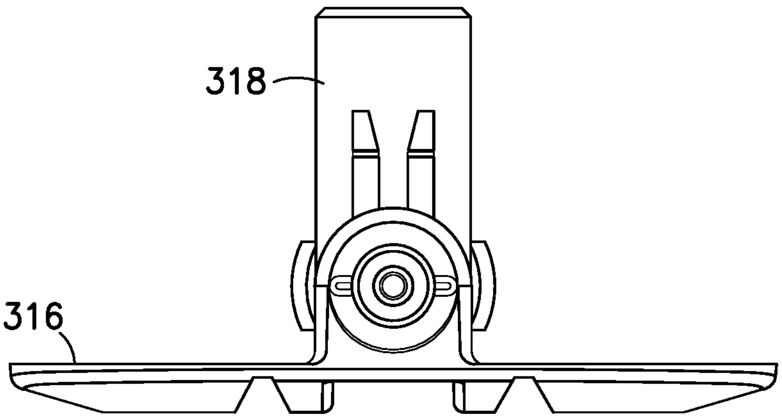
FIG. 93 illustrates a front elevation view of the side port catheter hub.
Figure 94:
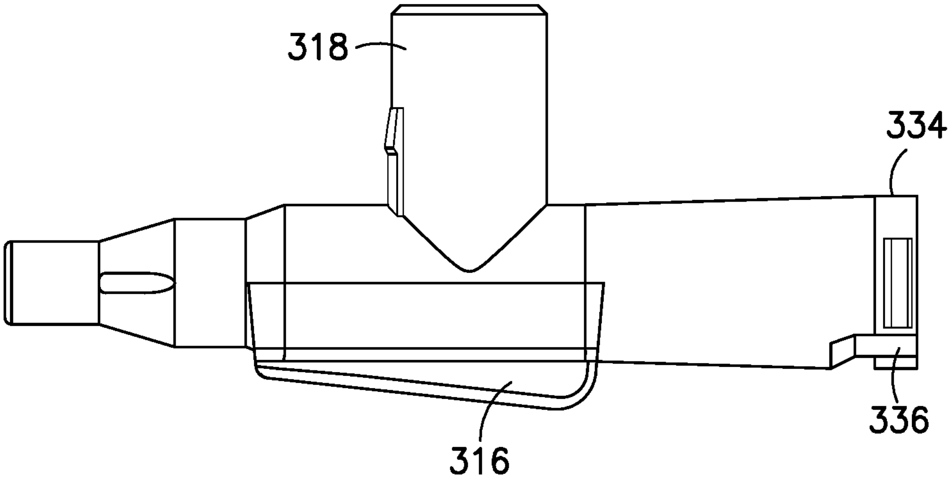
FIG. 94 illustrates a right side elevation view of the side port catheter hub.
Figure 95:
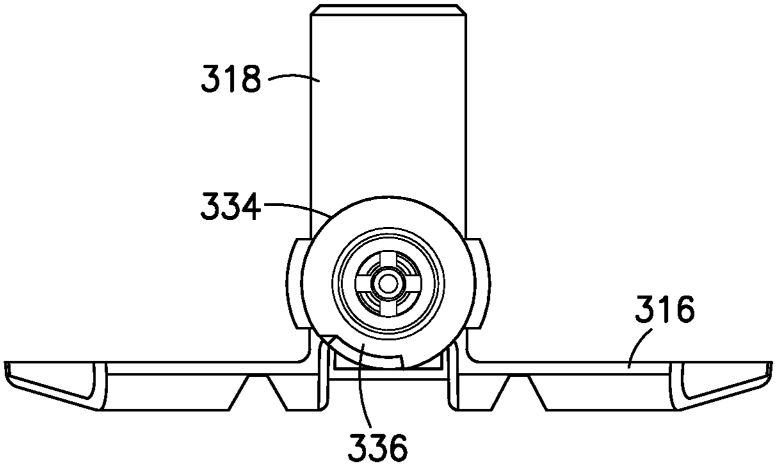
FIG. 95 illustrates a rear elevation view of the side port catheter hub.
Figure 96:
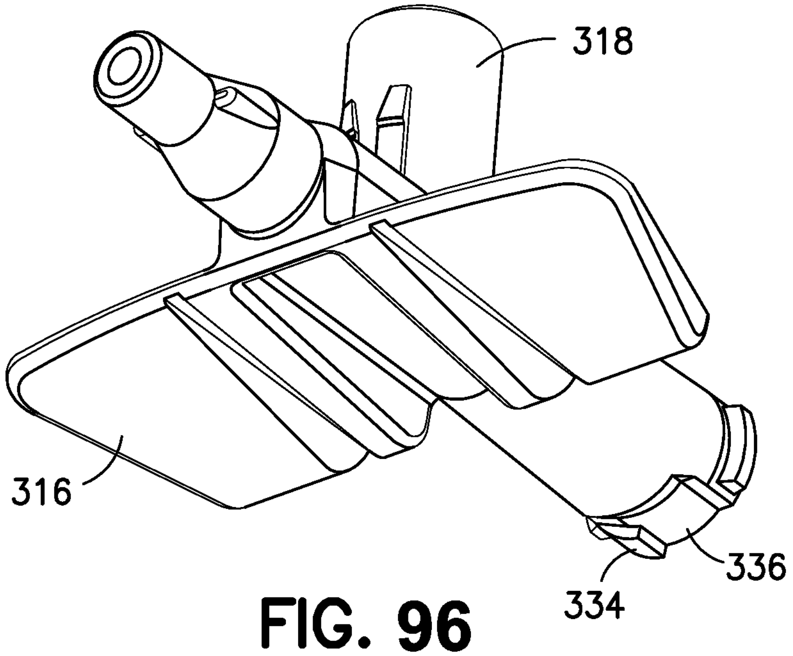
FIG. 96 illustrates a second left perspective view of the side port catheter hub.
Figure 97:
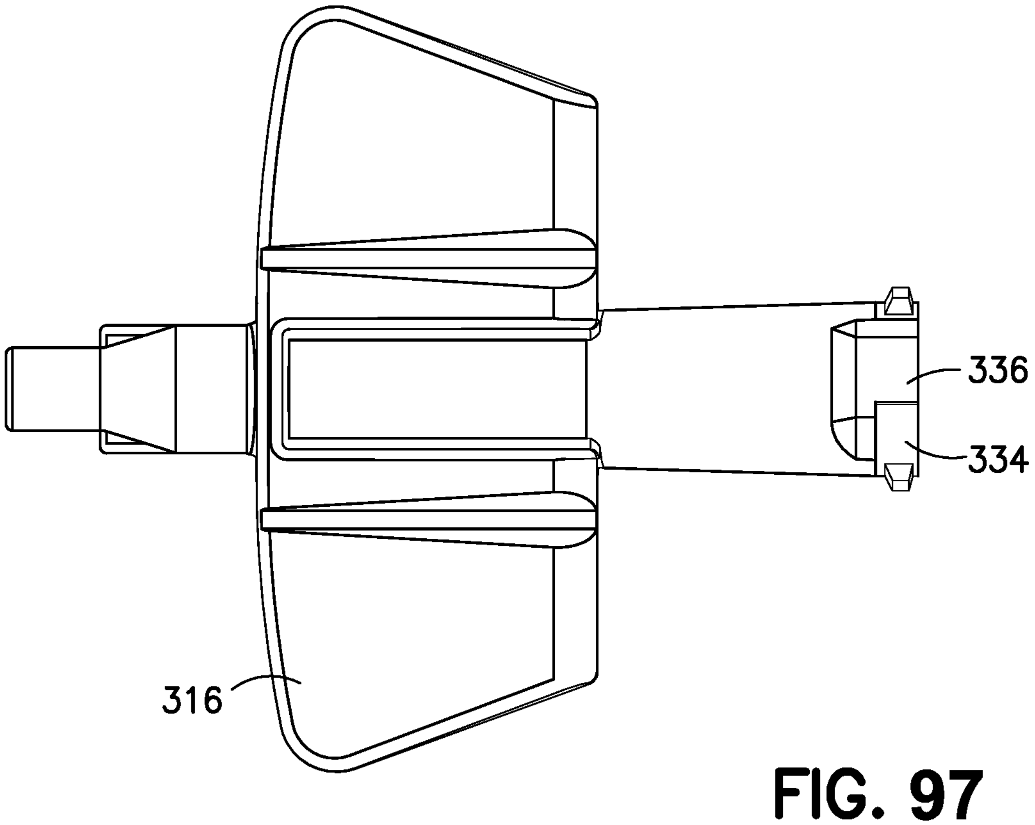
FIG. 97 illustrates a bottom plan view of the side port catheter hub.
Figure 98:
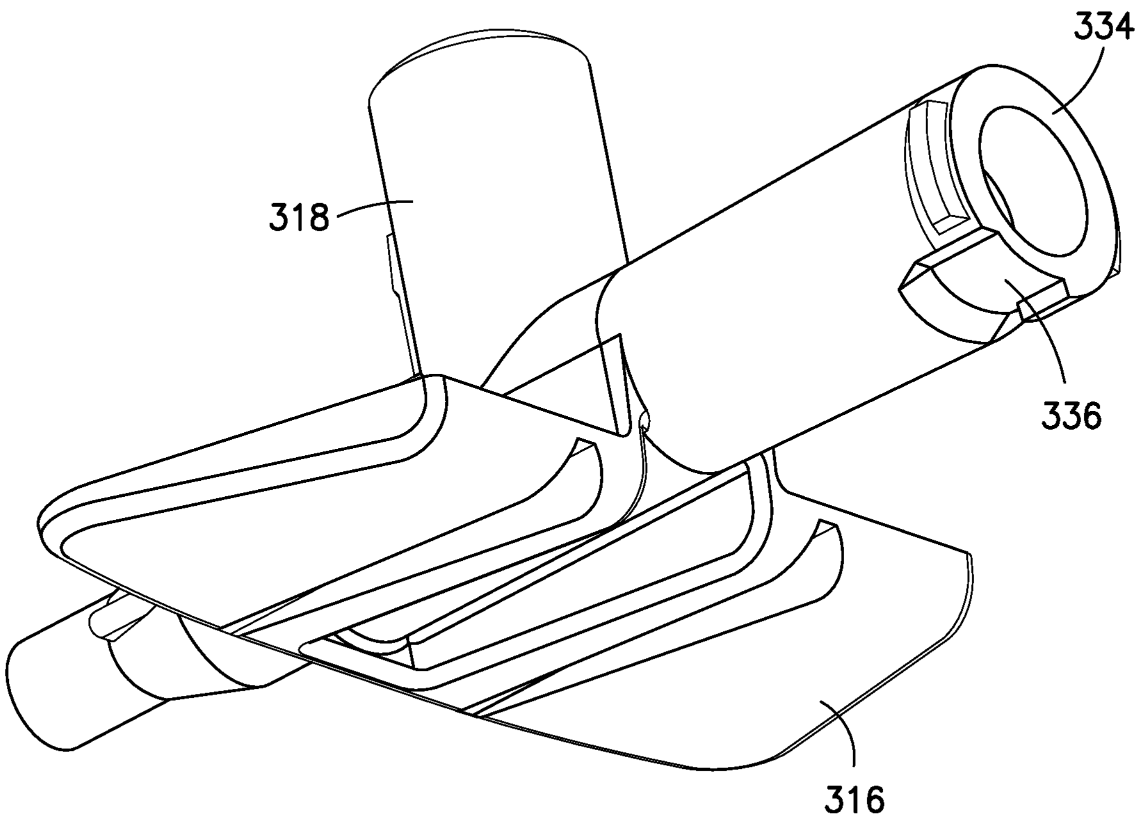
FIG. 98 illustrates a second right perspective view of the side port catheter hub.
Figure 99:
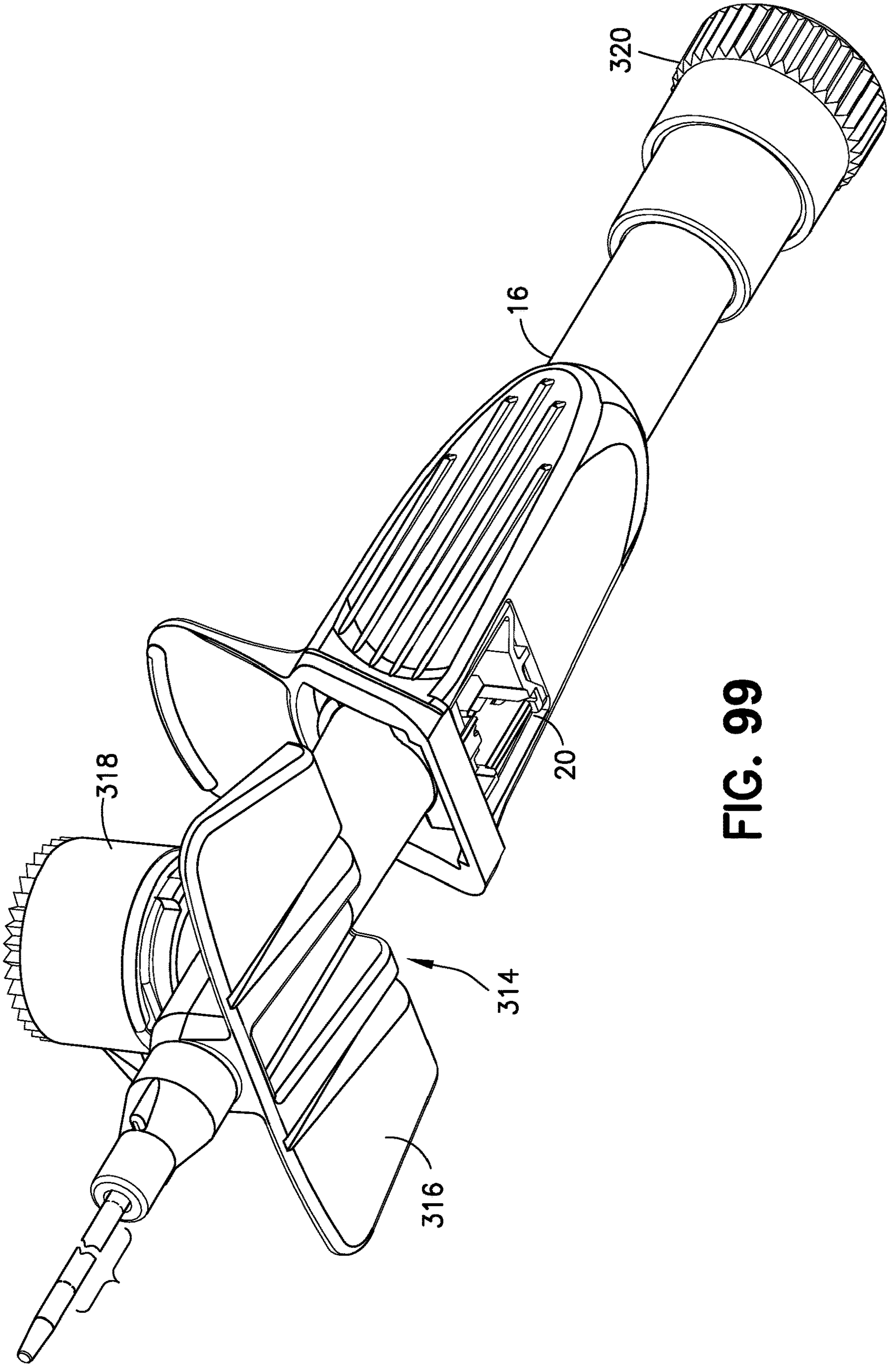
FIG. 99 illustrates a left perspective view of the alternative side port catheter hub assembly with a needle shield and needle hub.
Figure 100:
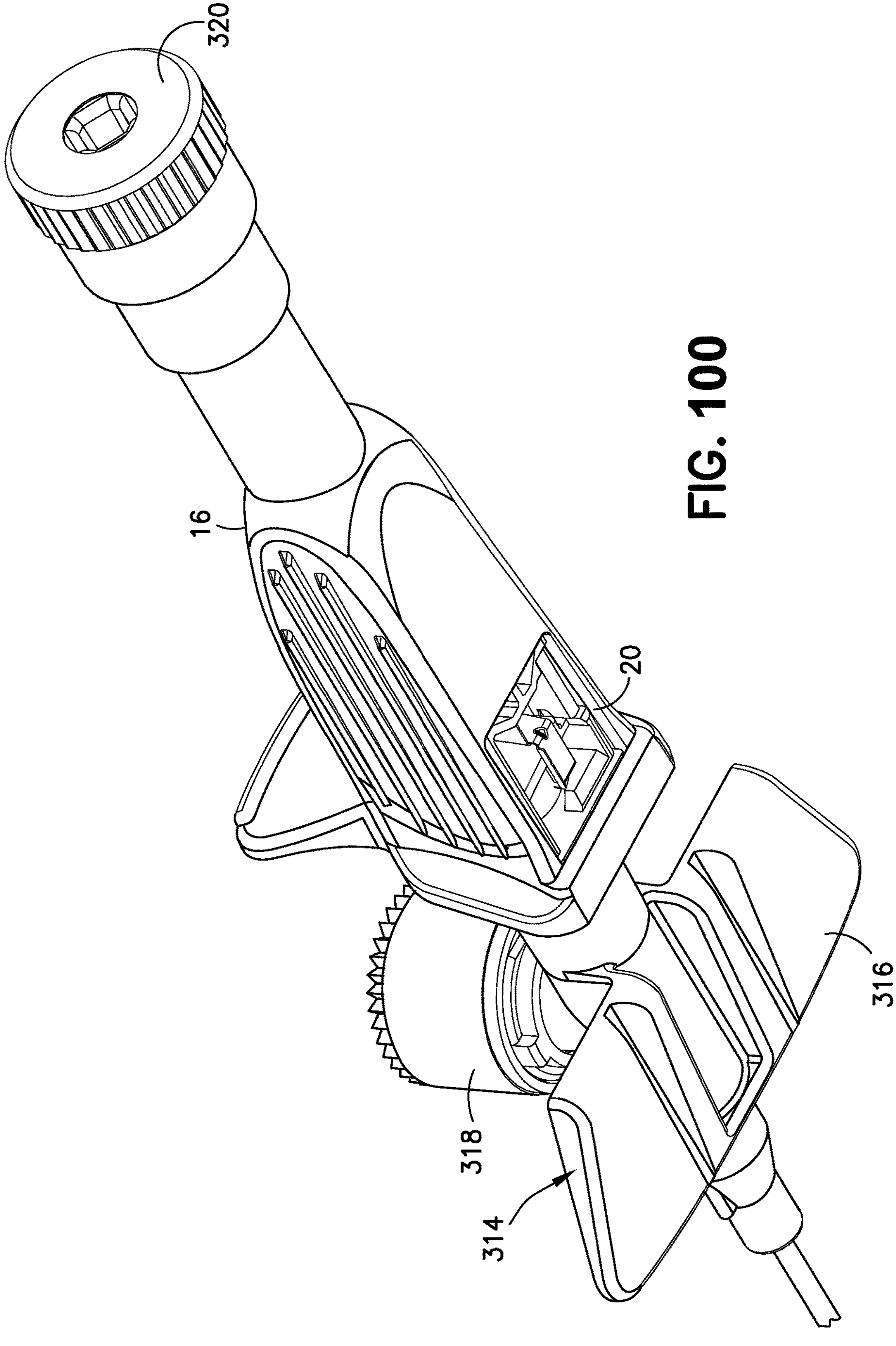
FIG. 100 illustrates a right perspective view of the alternative side port catheter hub assembly with a needle shield and needle hub.
Figure 101:
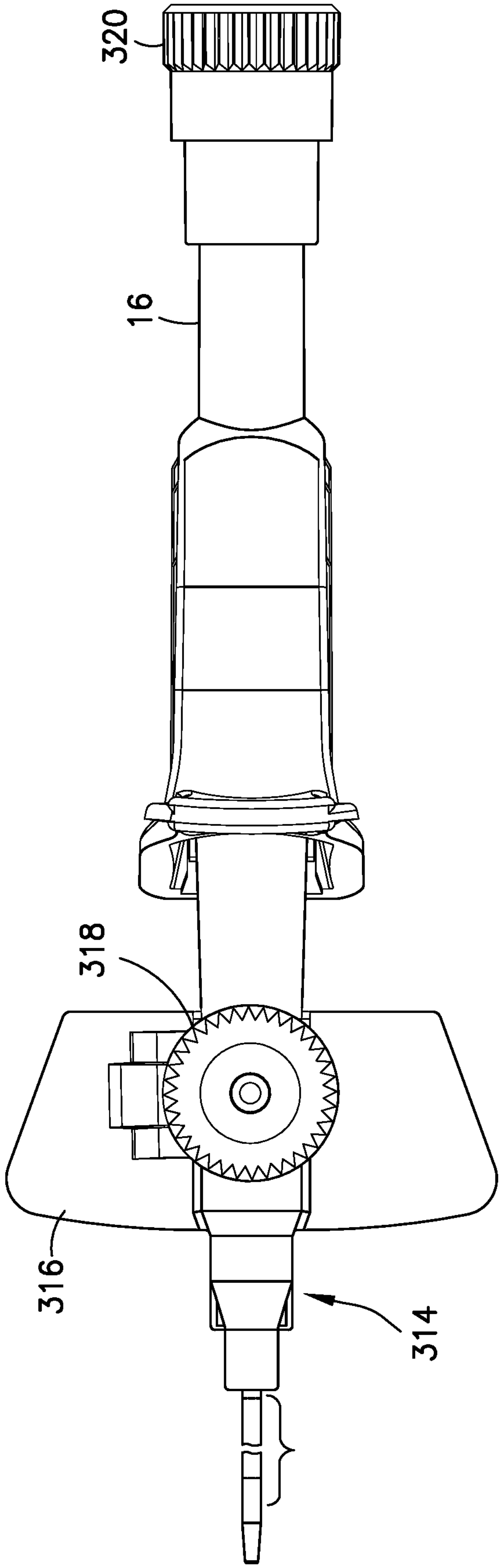
FIG. 101 illustrates a top plan view of the alternative side port catheter hub assembly with a needle shield and needle hub.
Figure 102:
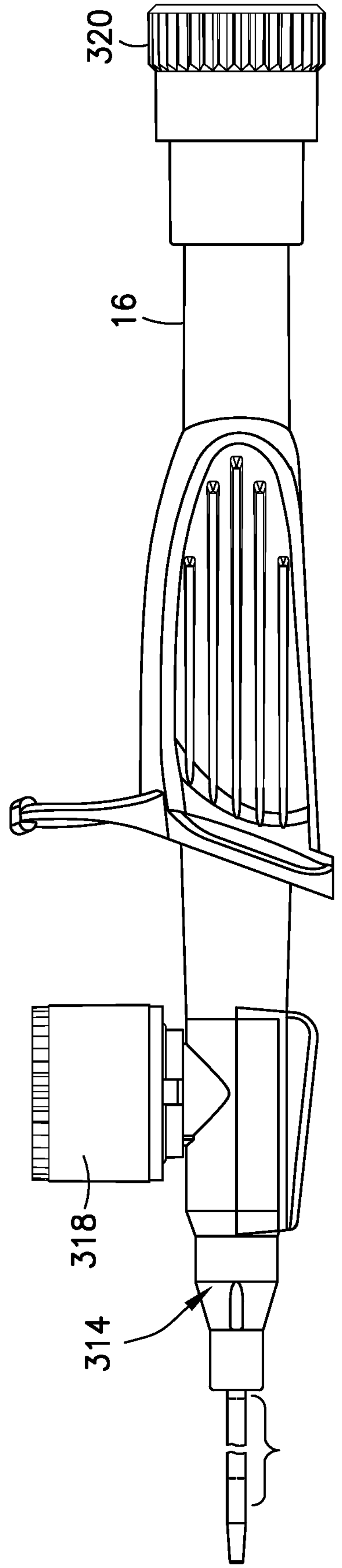
FIG. 102 illustrates a right side view of the alternative side port catheter hub assembly with a needle shield and needle hub.
Figure 103:
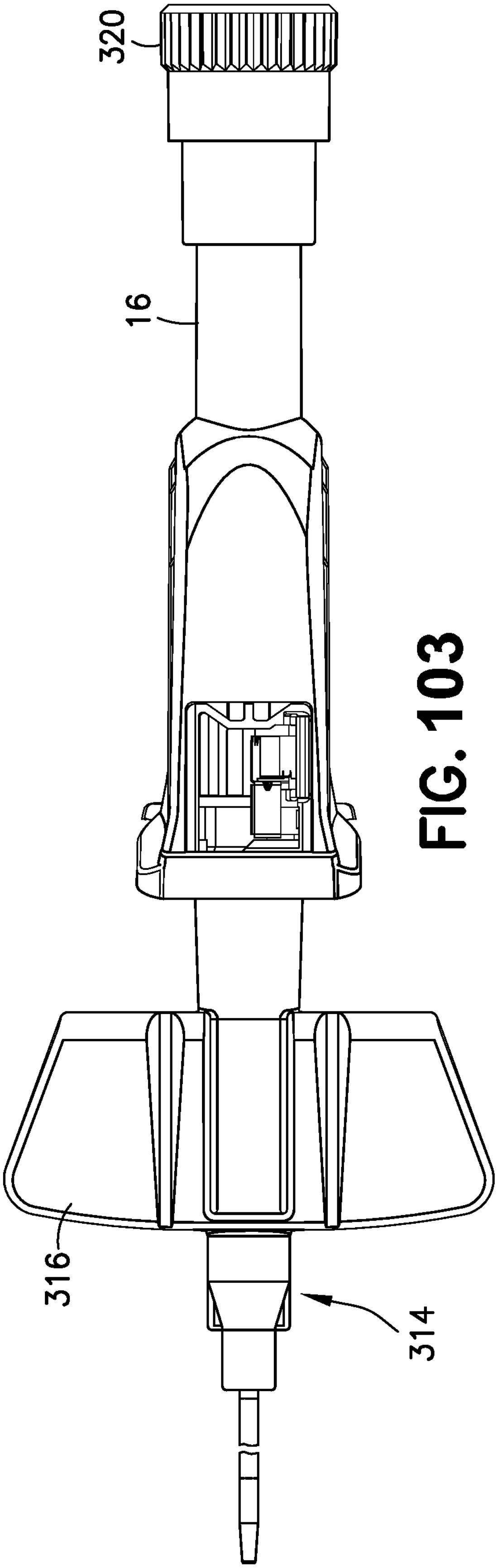
FIG. 103 illustrates a bottom plan view of the alternative side port catheter hub assembly with a needle shield and needle hub.
Figure 104:
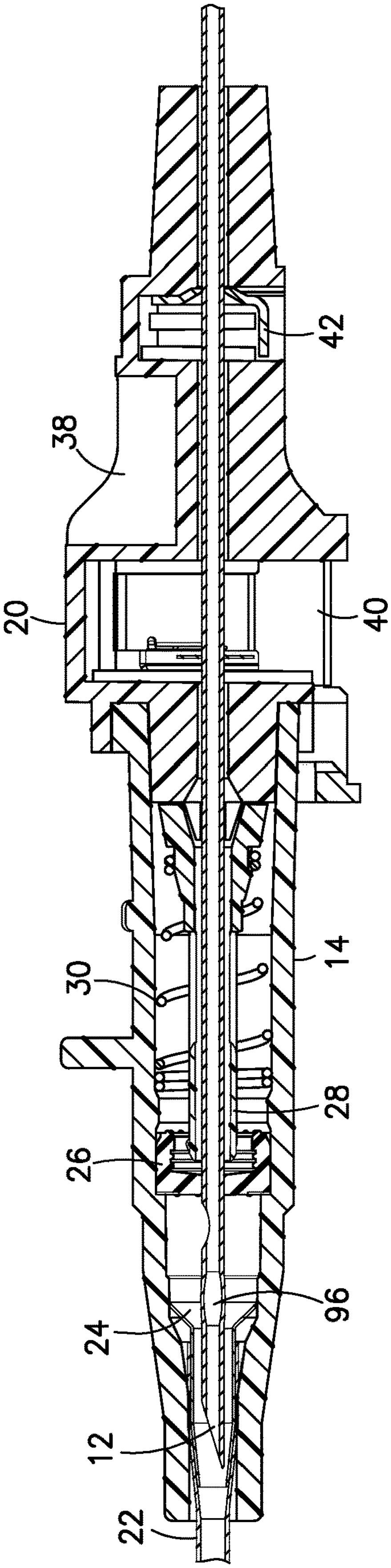
FIG. 104 illustrates a cross sectional view of the catheter assembly of FIGS. 1-12 as the introducer needle is being withdrawn.
Figure 105:
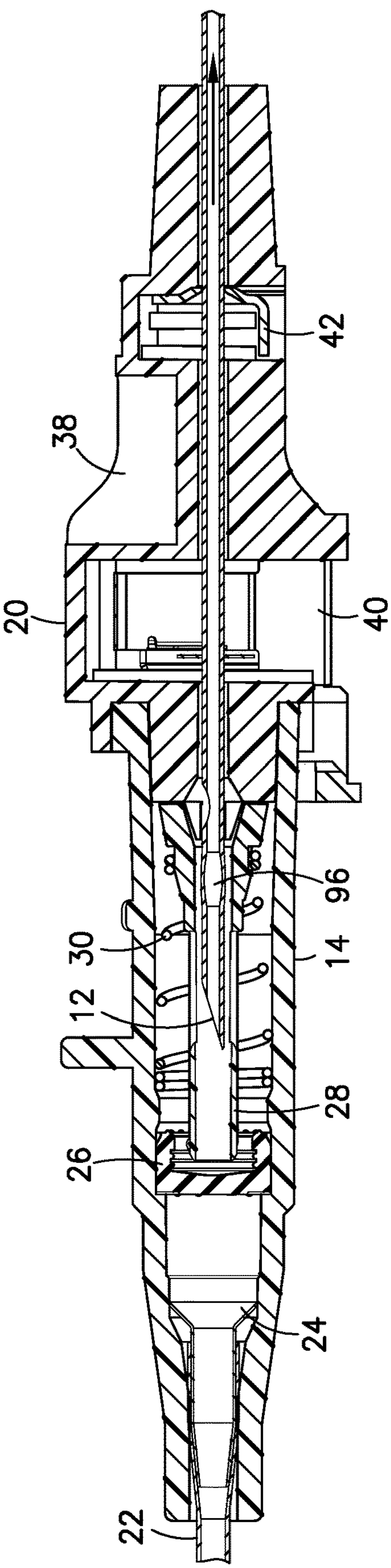
FIG. 105 illustrates a second cross sectional view of the catheter assembly of FIGS. 1-12 as the introducer needle is being withdrawn.
Figure 106:
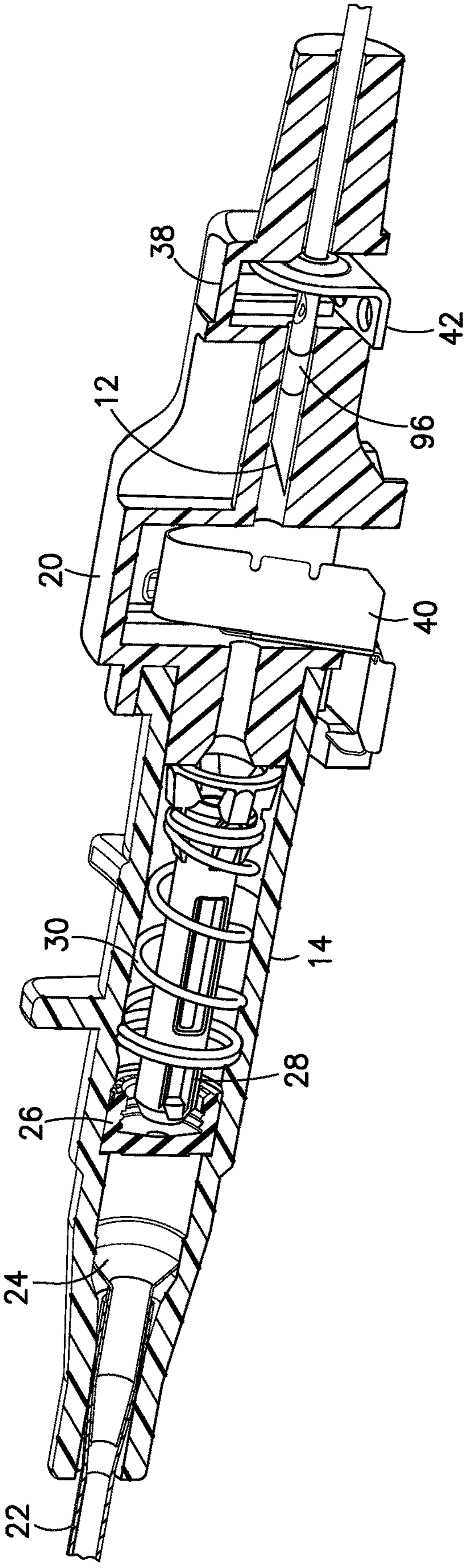
FIG. 106 illustrates a cross sectional view of the catheter assembly of FIGS. 1-16 as the introducer needle is moved past the V-shaped metal clip and the needle shield is separated from the catheter hub.

FIG. 74 illustrates an alternate embodiment of a clip 710 including a foot 732 and latch 734 being disposed between the first and second legs 712, 714. The foot 732 includes a rib 736 to provide improved stiffness and strength. Additionally, the flag 728 is directly connected to the first leg 712. The flag 28 is not directly connected to the foot 732 and latch 734. The design of the clip 710 where the flag 728 attaches only to the first leg 712 advantageously provides extra space for tooling during manufacturing and improves assembly.

Figure 75:
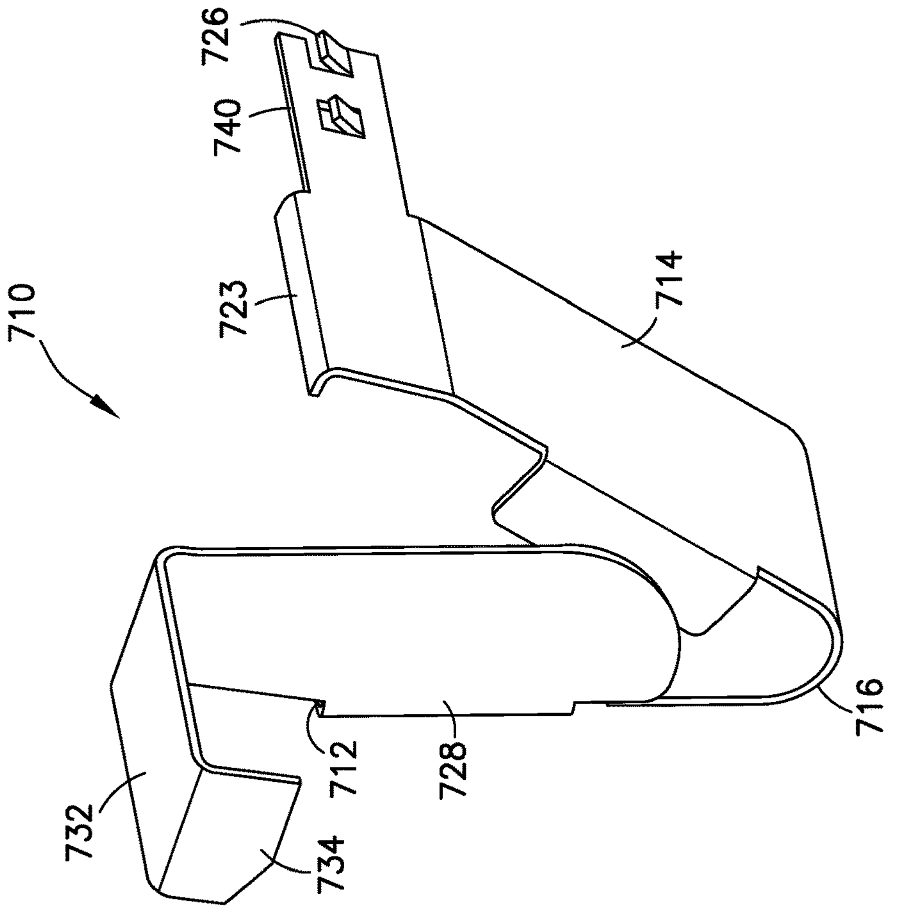
FIG. 75 illustrates a right, rear perspective view of an alternate embodiment of the V-shaped metal clip of the catheter assembly.

FIG. 75 illustrates an alternate embodiment of a clip 710 including a second leg 714 having a ledge 723 at a top portion of the second leg 714. The second leg 714 further includes a rear wall 740 disposed below the ledge 723. The rear wall 740 bends approximately 90 degrees inward toward the first leg 712. The rear wall 740 includes barbs 726 that mount on to the needle shield to secure the clip 710.

Referring to the earlier drawings, the clip 40 of FIGS. 40-48 is connected to the outer housing 38 with the spade 66 being positioned around an exterior wall of the outer housing 38. The spade 66 is attached to the exterior wall of the outer housing 38 so that the outer wall 70 of the spade 66 is exposed to the outside of the needle shield 20. This configuration advantageously reduces the width of the needle shield 20, compared to an arrangement wherein the spade 66 is received within an internal cavity of the outer housing 38 such that the outer wall 70 is not exposed to the outside of the outer housing 38. As best shown in FIGS. 106-112, the inner wall 72 of the spade 66 is positioned in a recess and the two barbs 76 extend away from the inner wall 72 to engage a pair of projections 89 in the needle shield 20. The two barbs 76 aid in securely fastening the clip 40 to an inner surface of the needle shield 20. The clip 40 may be formed from a metal, elastomer, polymer, or composite material. In various exemplary embodiments, the clip 40 is formed from a thin piece of resilient metal, such as stainless steel.

According to an exemplary embodiment illustrated in FIGS. 76-80, the washer 42 includes a base 88 and a side wall 90 connected together in a substantially L-shape. The side wall 90 includes a funnel 92 and an opening 94. The needle 12 includes a deformation 96, for example a crimp or protrusion formed near the distal end of the needle 12. The opening 94 in the washer 42 is sized to allow passage of the needle shaft, but not the deformation 96. The funnel 92 makes it easier for the proximal end of the needle 12 to be initially inserted through the washer 42 during assembly.

FIGS. 81-89 depict an alternative exemplary catheter hub 214 having a pair of stabilization wings 216. FIGS. 90-103 depict another alternative exemplary side port catheter hub 314 having a pair of stabilization wings 316 and a side port 318. The side port communicates with an internal tubular valve (not shown) as described in U.S. Pat. No. 4,231,367, which is incorporated herein by reference. The alternative catheter hubs 214, 314 each have a collar 234, 334 with an opening 236, 336 to receive the latch 84 of the needle shield 20.

The catheter assemblies can include a plug 320 that is initially attached to the needle hub 16. After the needle hub 16 and needle shield 20 have been removed from the catheter hub, the plug 320 can be removed from the needle hub 16 and attached to the open, proximal end of the catheter hub. Although depicted with only the side port catheter 314, the plug 320 can be used with any of the catheter hubs 14, 214, 314.

Figure 107:
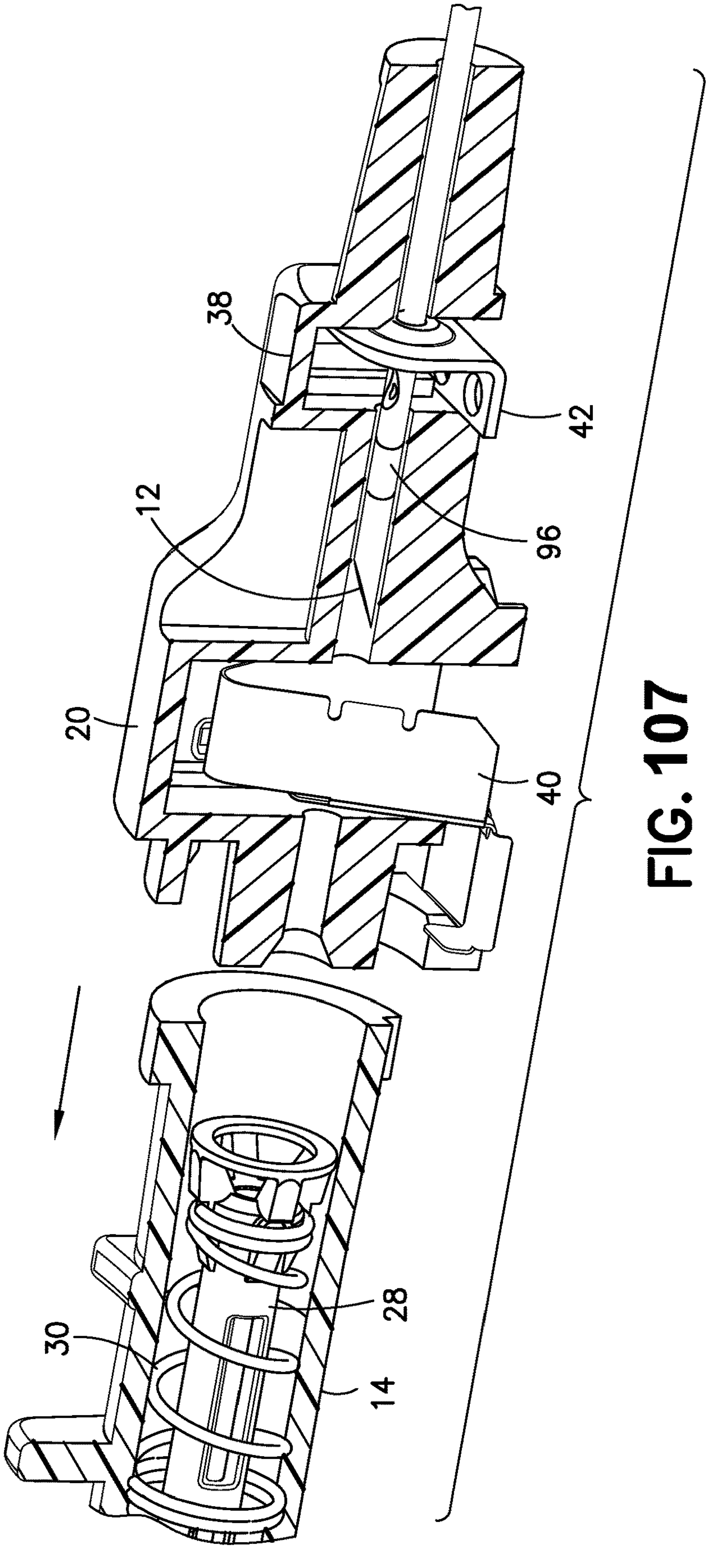
FIG. 107 illustrates a second cross sectional view of the catheter assembly of FIGS. 1-16 as the introducer needle is moved past the V-shaped metal clip and the needle shield is separated from the catheter hub.
Figure 108:
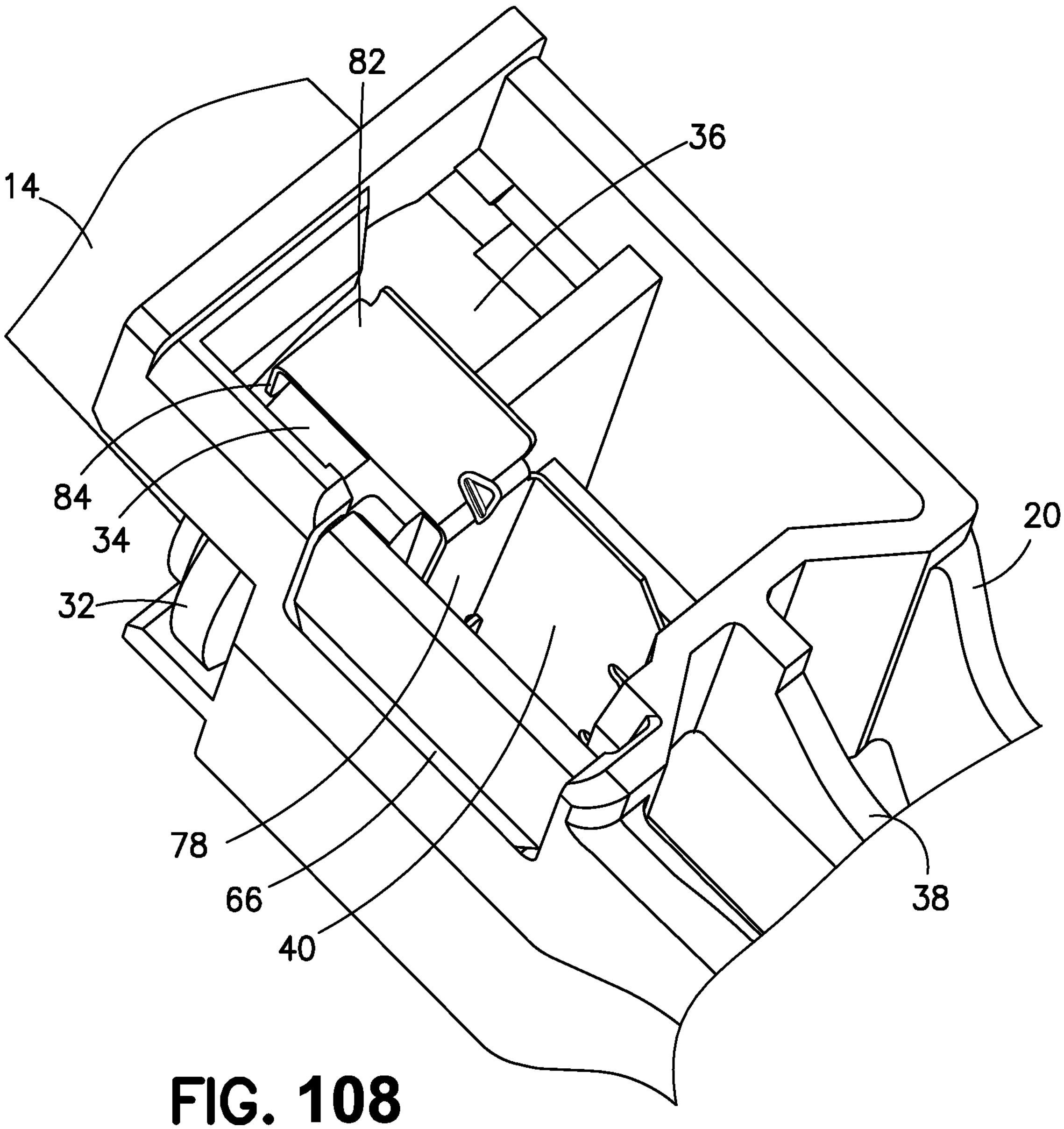
FIG. 108 illustrates a latch of the V-shaped metal clip engaged with the catheter hub.
Figure 109:
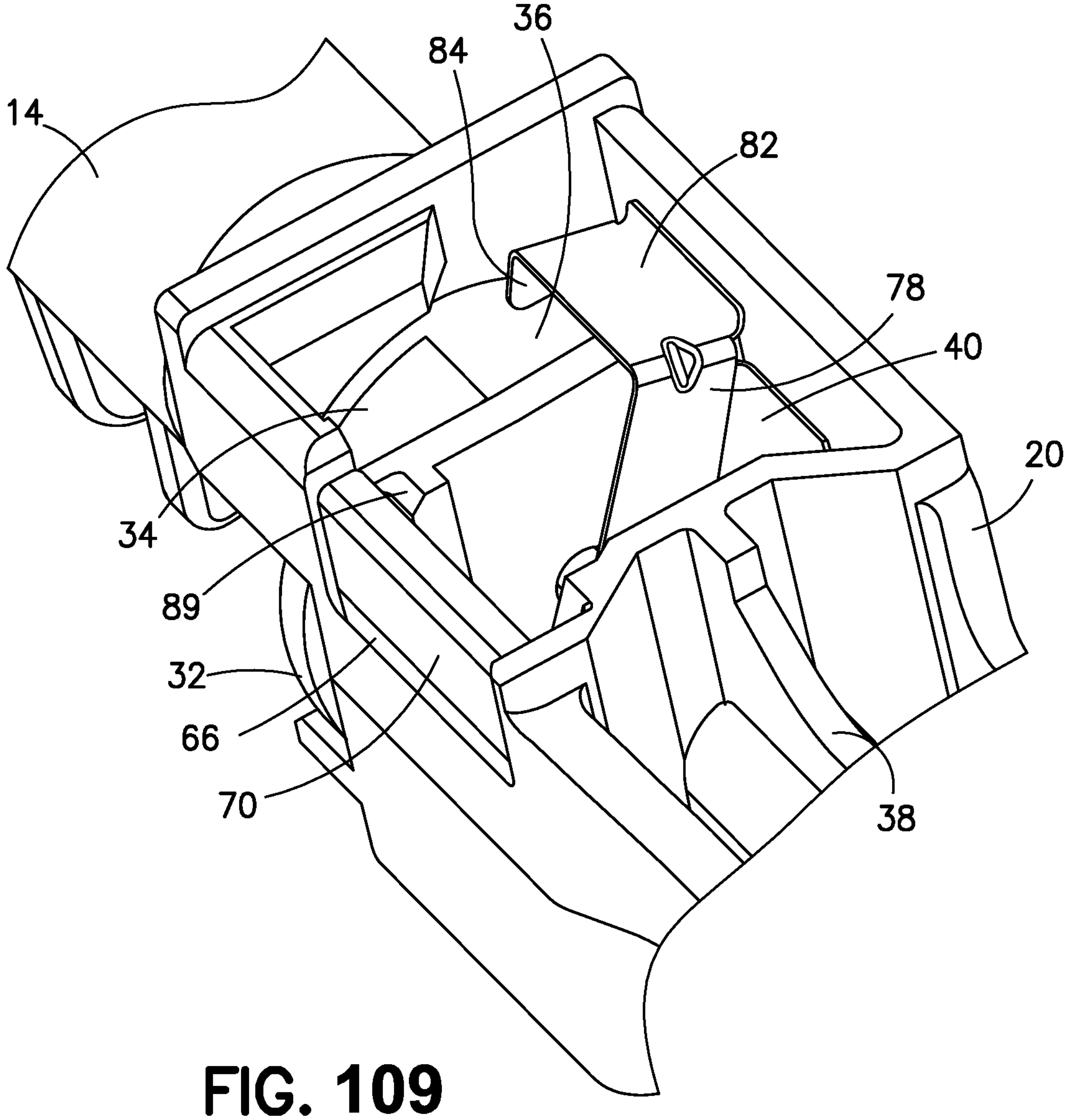
FIG. 109 illustrates the latch of the V-shaped metal clip disengaged from the catheter hub.
Figure 110:
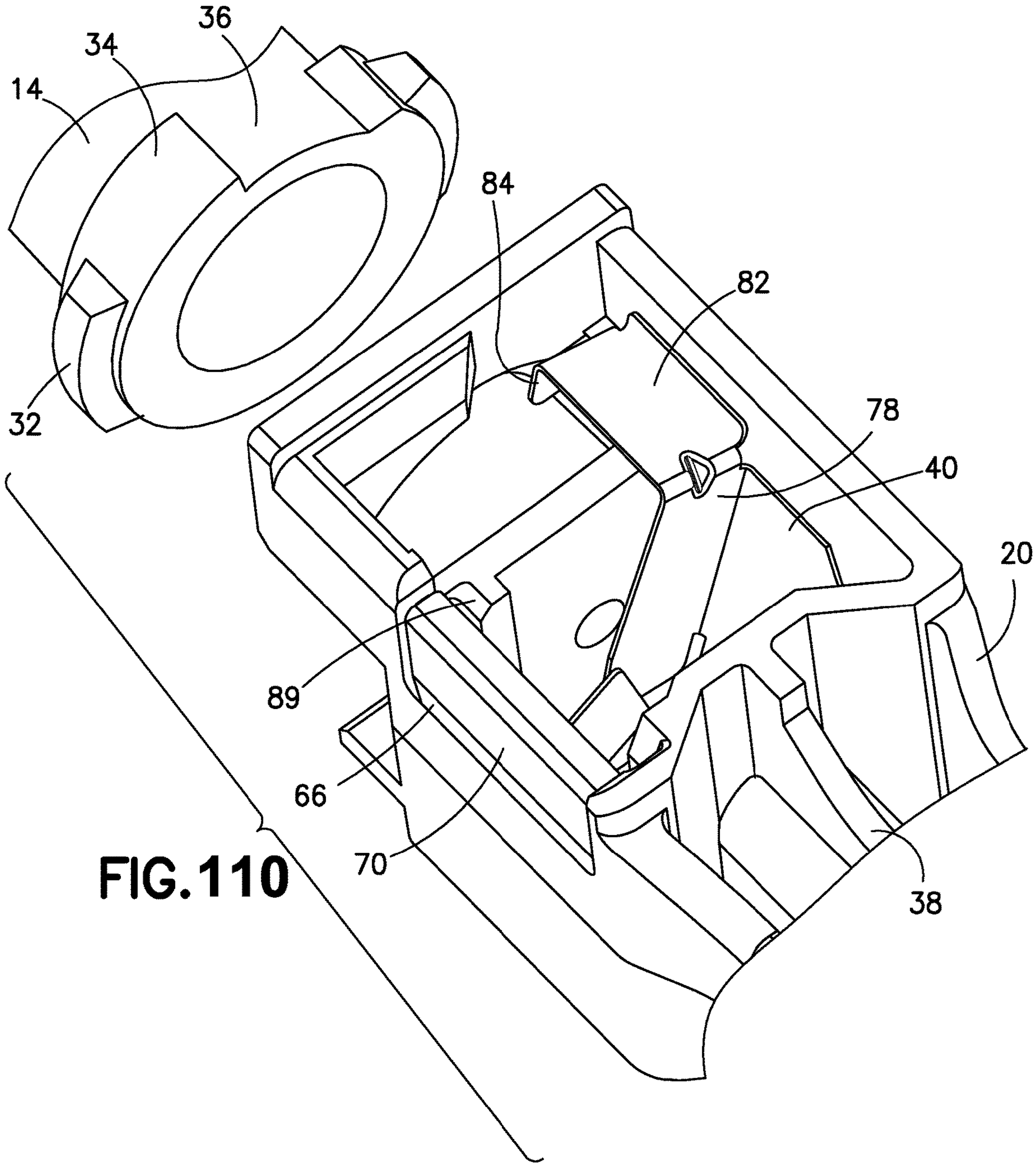
FIG. 110 illustrates the latch of the V-shaped metal clip disengaged from the catheter hub and separated.
Figure 111:
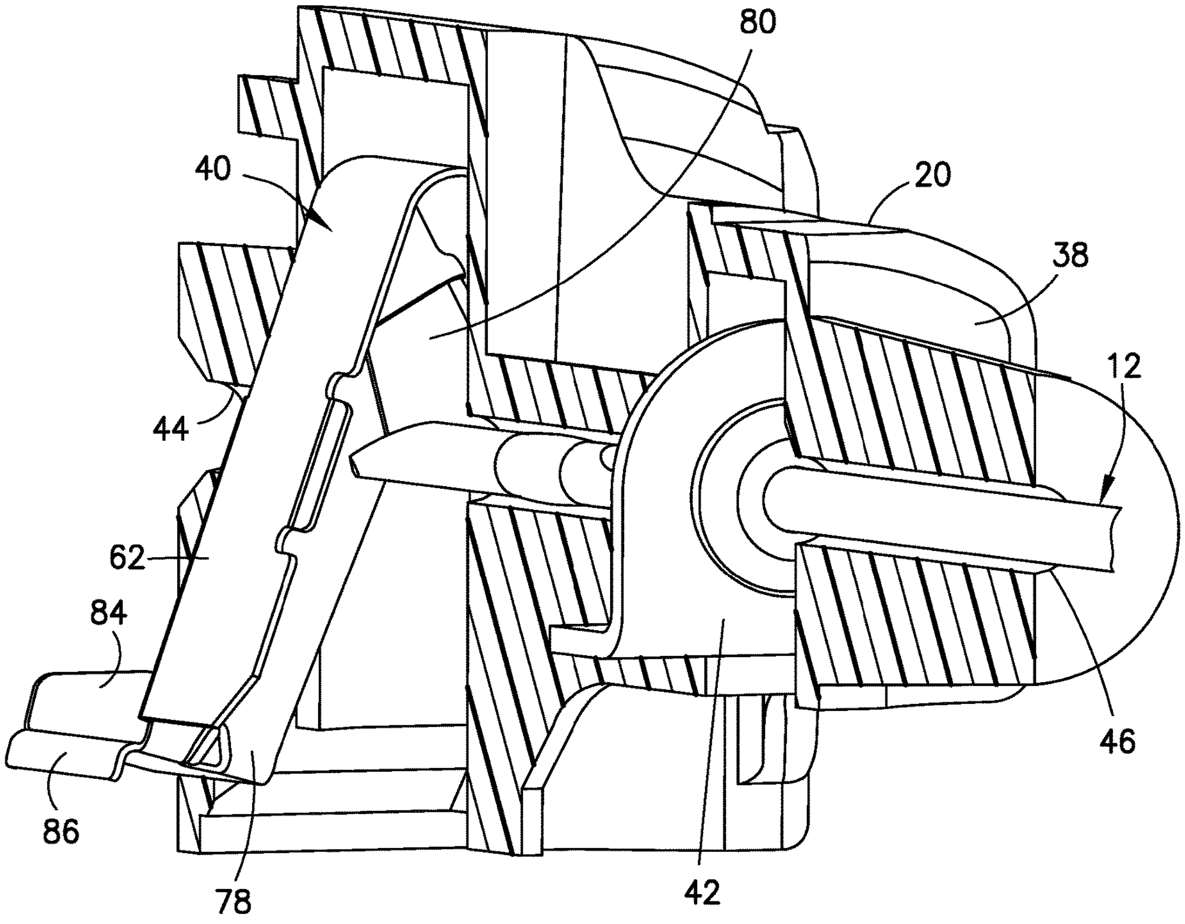
FIG. 111 illustrates a view of the V-shaped metal clip blocking the needle.
Figure 112:
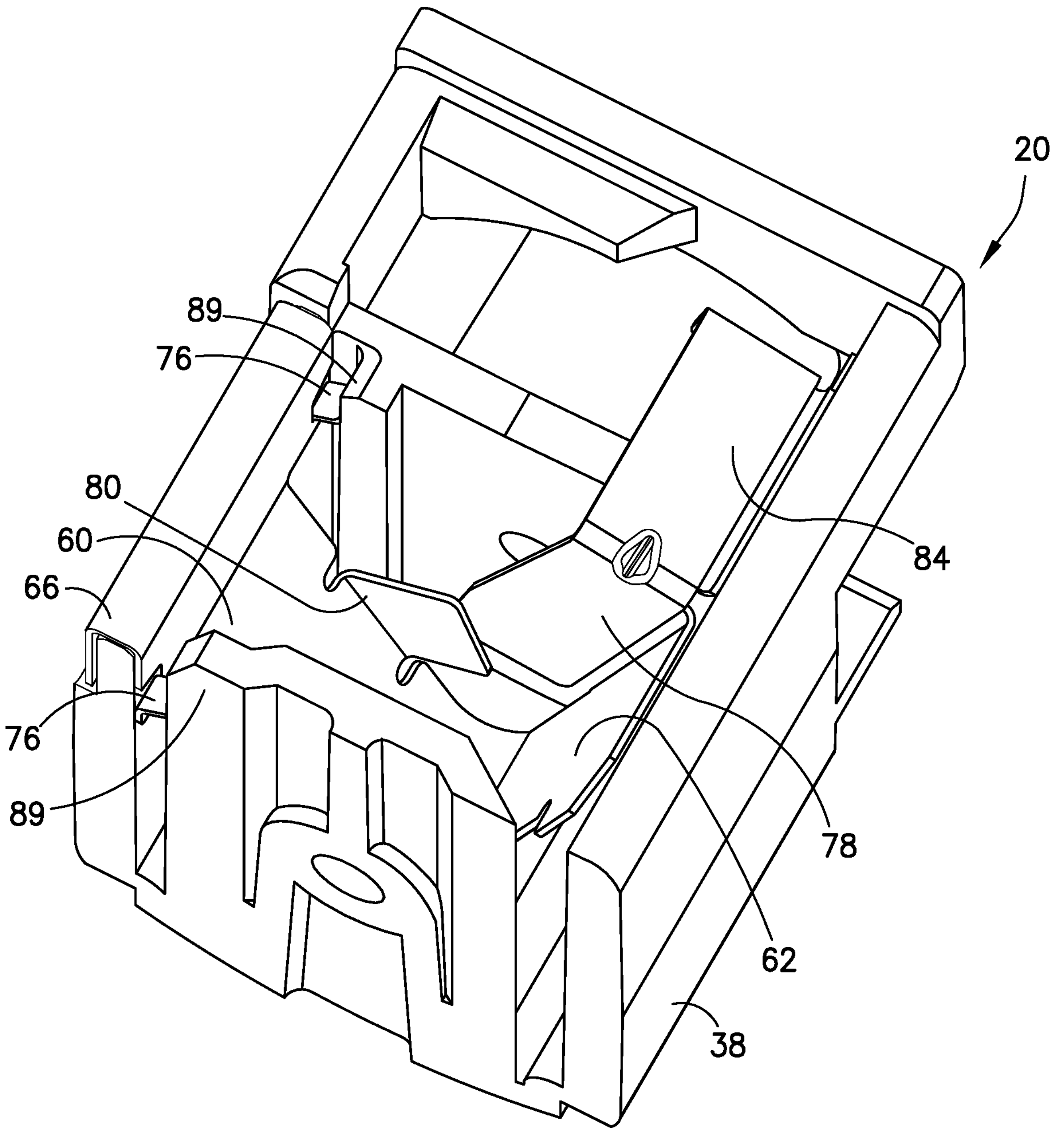
FIG. 112 illustrates a view of the V-shaped metal clip in the closed position.
Figure 113:
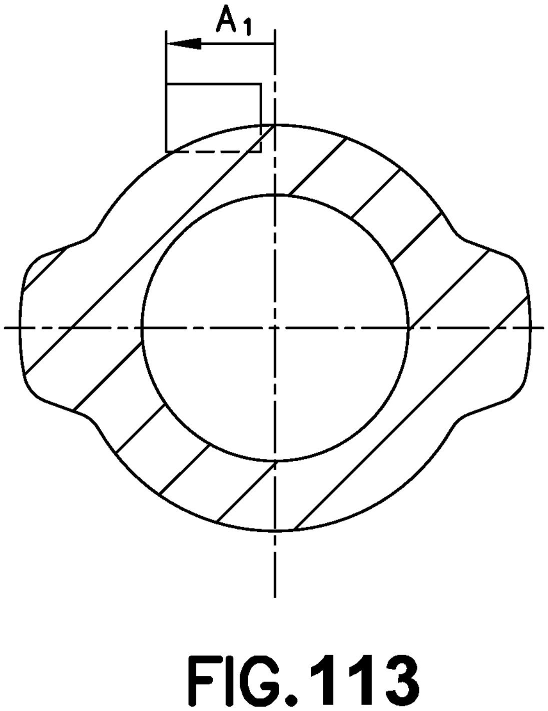
FIG. 113 illustrates a schematic view of the working envelope of the V-shaped metal clip and catheter hub collar without a notch.
Figure 114:
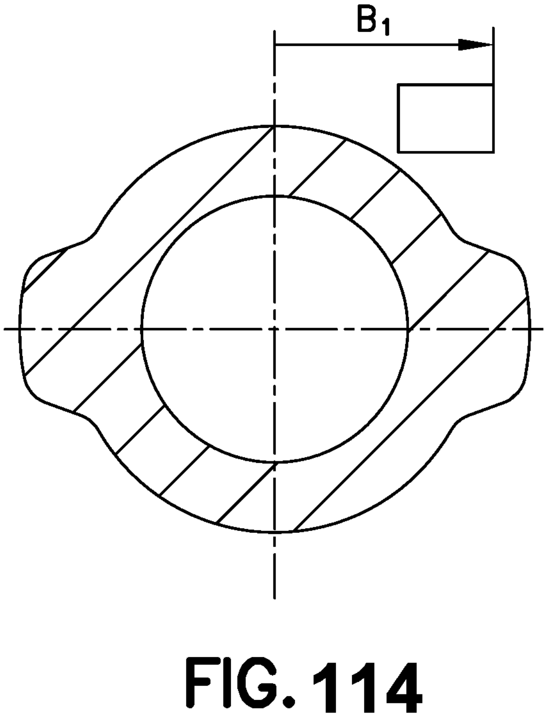
FIG. 114 illustrates a schematic view of the working envelope of the V-shaped metal clip and catheter hub collar without the notch.
Figure 115:
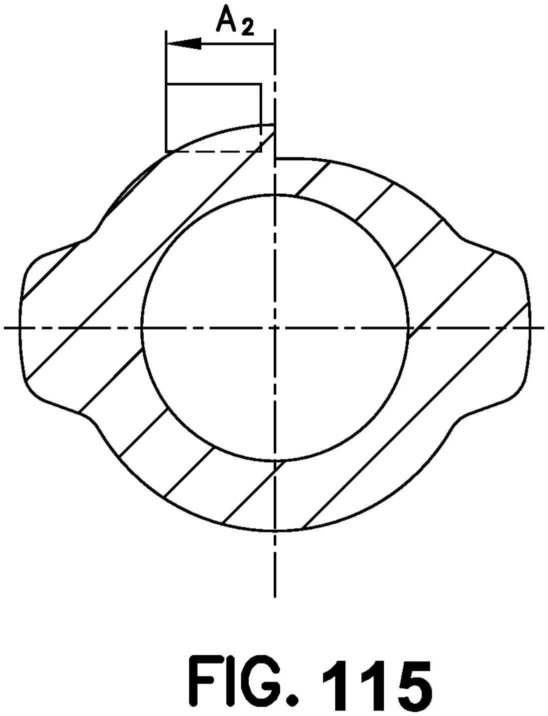
FIG. 115 illustrates a schematic view of the working envelope of the V-shaped metal clip and notched catheter hub collar.
Figure 116:
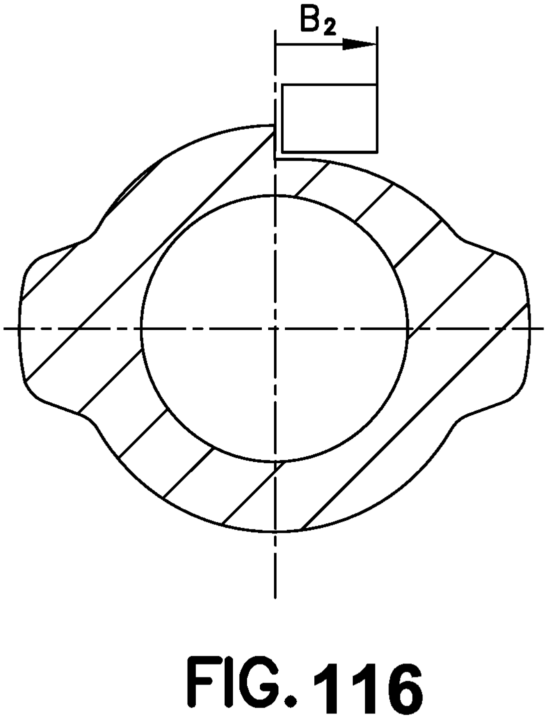
FIG. 116 illustrates a schematic view of the working envelope of the V-shaped metal clip and notched catheter hub collar.

FIGS. 104-112 depict the catheter assembly 10 of FIGS. 1-12 during operation. Initially, the needle shield 20 is connected to the catheter hub 14 and the introducer needle 12 passes through the catheter hub 14 and the needle shield 20. The nose 48 of the needle shield 20 (labeled in FIG. 30) may or may not extend into the catheter hub 14 when the needle 12 is in use (first position). The needle 12 cooperates with the clip 40 by biasing the clip 40 into a locked position via pressing the first and second arms 60, 62 toward one another. In the locked position, the latch 84 engages the collar 34, preventing removal of the needle shield 20 from the catheter hub 14, as best shown in FIG. 108. At the same time, in the locked position, the latch 84 is offset from the collar opening 36. The position of the latch 84 is off-center with respect to the needle 12. The clip 40 is also in an open position, allowing the needle 12 to traverse through the clip 40.

As the needle 12 is withdrawn from the catheter hub 14 and into the needle shield 20, the tip of the needle 12 clears the clip 40, and the clip 40 is allowed to resiliently expand, causing the second arm 62 to move away from the first arm 60. As the clip 40 expands laterally, the primary and secondary flags 78, 80 block the distal opening 44 of the outer housing 38 aperture, preventing the tip of the needle 12 from exiting the distal end of the outer housing 38.

Movement of the second leg 62 moves the latch 84 laterally from engagement with the collar 34 to a position aligned with the collar opening 36, allowing the needle shield 20 to be disengaged or unlocked from the catheter hub 14. The direction in which the latch 84 moves is lateral with respect to a centerline of the needle 12. The latch 84 movement is not radial toward or away from the needle 12. Moreover, as the latch 84 is adjusted, the latch 84 moves to a centered position and then ultimately moves off-center with respect to the needle 12. The off-center positions of the latch 84 in the first and second positions of the needle 12 are symmetrically opposite each other.

In the position when the flags 78, 80 block the needle 12, the clip 40 moves to a closed position. At the same time, the needle 12 enters into a second position that is retracted from the first needle position, which prevents further use of the needle 12. The first position, as described above, is understood as, for example, all positions of the needle 12 prior to entering the second position.

As the needle 12 is pulled further in the proximal direction, the shaft of the needle 12 slides through the needle shield 20 until the deformation 96 formed near the distal end of the needle 12 cooperates with and engages the washer 42, as shown in FIG. 107. The opening in the washer 42 is sized to allow passage of the needle shaft, but not the deformation 96. Thus, the washer 42 prevents the distal tip of the needle 12 and the deformation 96 from exiting the needle shield 20 when the needle 12 is in the second position. The combination of the washer 42 and the needle shield 20 enclose or cover the distal tip of the needle 12 in this second position. Further proximal movement of the needle 12 results in the needle shield 20 being pulled away from the catheter hub 14.

The combination of the clip 40 and the washer 42 act as an exemplary needle tip protection mechanism. This needle tip protection mechanism encloses or covers the distal needle tip and the deformation 96 and prevents these portions of the needle 12 from exiting the needle shield 20.

More information regarding needle tip protection mechanisms of the type used in this embodiment can be found in U.S. Pat. Nos. 6,749,588 and 7,604,616, and U.S. Patent Application Publication No. 2014/0364809, the contents of which are hereby incorporated by reference. The features described in this embodiment, including the needle protection features, can be used in combination with the features described throughout this application.

As depicted in FIGS. 113-116, the use of the clip 40 and the notched collar 34 allows for a smaller, more compact design. Without the collar opening 36, the latch 84 would have to move a distance B1 to clear the collar and allow disengagement of the needle shield 20. With the collar opening 36, the latch 84 does not have to clear the entire catheter hub 14 and only needs to move a distance B2 which is less than B1.

Figure 117:
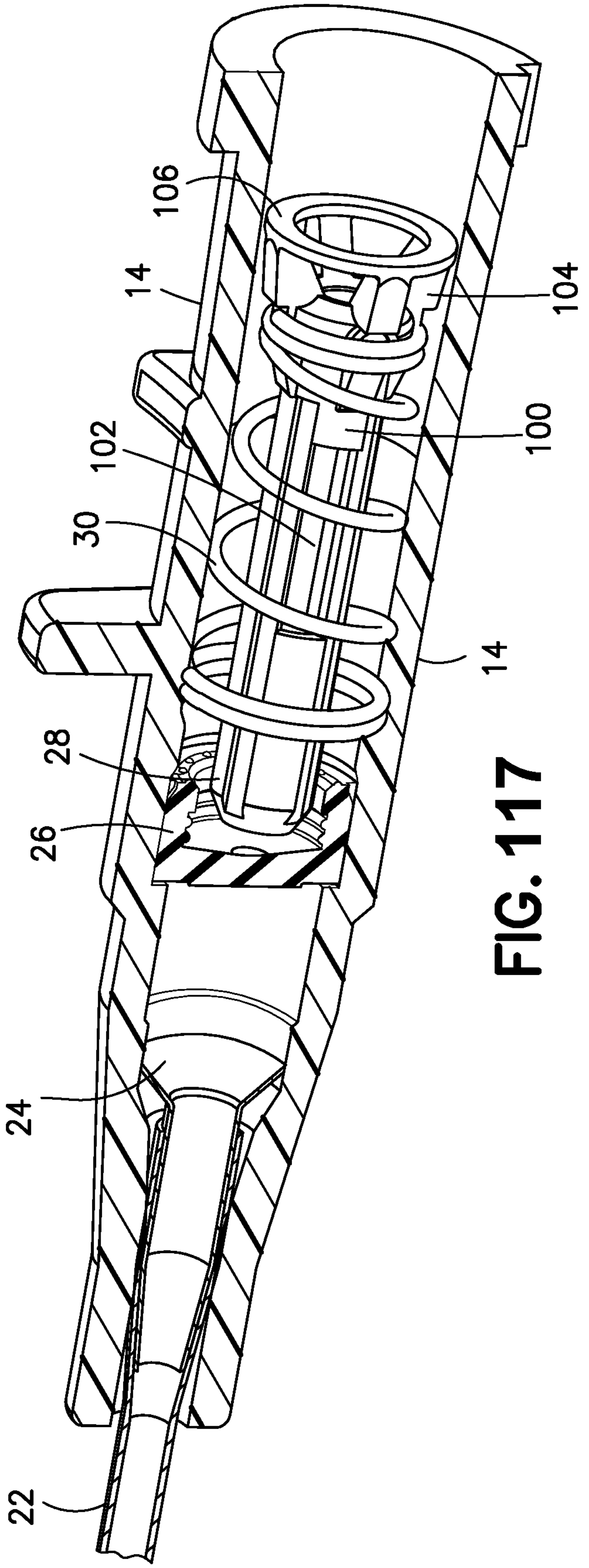
FIG. 117 illustrates the operation of the catheter hub valve actuator in a free state.
Figure 118:
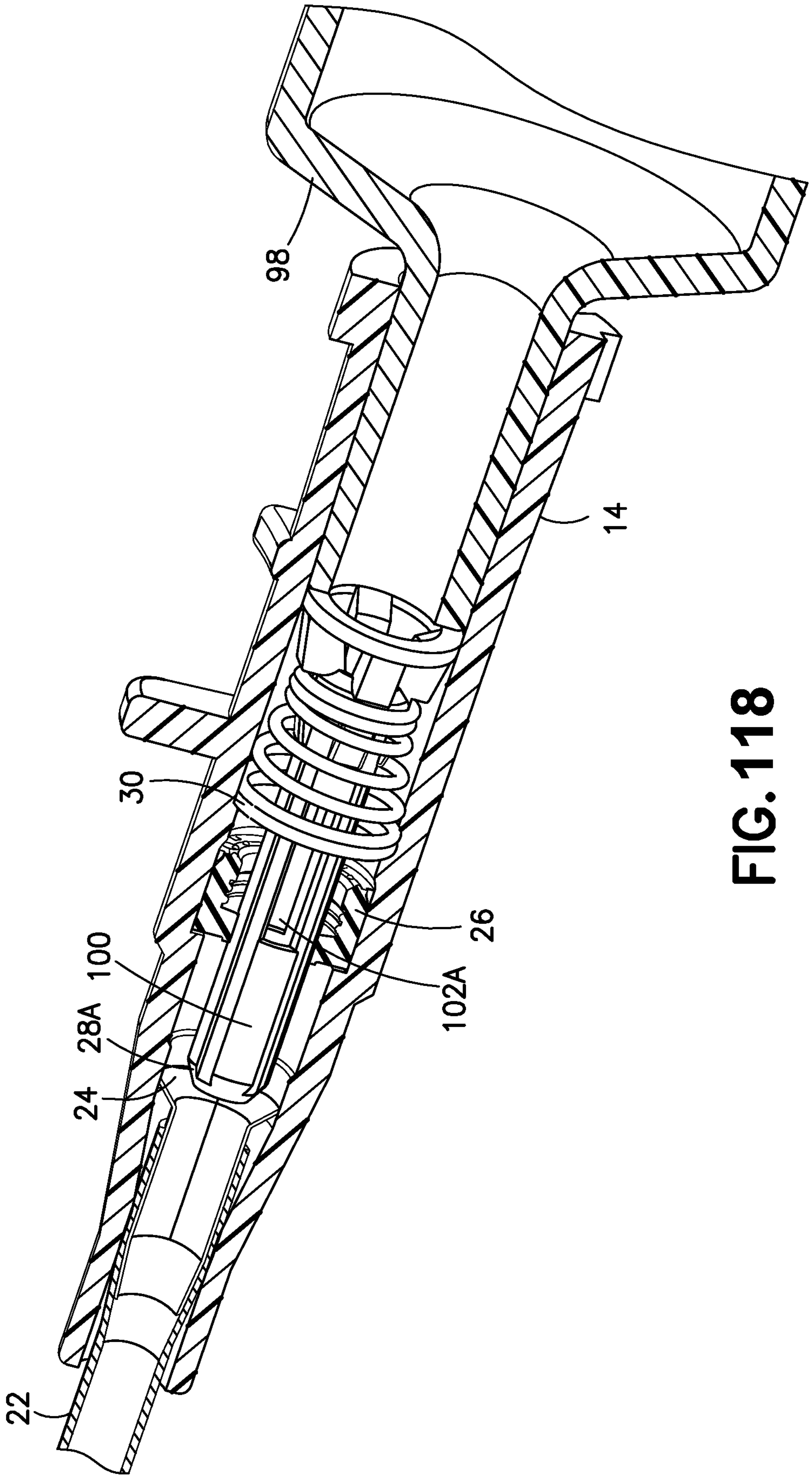
FIG. 118 illustrates the operation of the catheter hub valve actuator in a compressed state.

FIGS. 117 and 118 depict the use of the catheter valve actuator 28. The introducer needle 12 initially extends through the actuator 28, the septum 26, the wedge 24, and the catheter tube 22. After the introducer needle 12 and the catheter tube 22 are inserted into a patient, the needle 12 is withdrawn, closing the septum 26. As a male Luer connector 98 is inserted into the catheter hub 14, the Luer connector 98 abuts and moves the actuator 28 in the distal direction, compressing the biasing member 30. Further insertion of the Luer connector 98 moves the actuator 28 through the septum 26, opening the slits and allowing fluid to flow through the catheter hub 14.

When the Luer connector 98 is removed, the biasing member 30 moves the actuator 28 in the opposite direction, removing it from the septum 26, closing the slits, and preventing fluid from flowing therethrough. This allows the catheter to be reused while in the patient's vein, as opposed to a single-use catheter where the actuator would remain in the septum after a Luer connector 98 is removed. However, a single-use catheter can also be used with the needle shield 20 described herein.

The actuator 28 has an actuator barrel 100 surrounding an internal passage. The actuator barrel 100 is a substantially tubular member and the internal passage is substantially cylindrical. A first end of the actuator barrel 100 has a nose with a chamfered outer surface to engage the septum 26. The tubular member has one or more openings 102 to permit fluid flow through and around the actuator barrel 100. The actuator 28 includes a rear portion for engaging a male Luer connector.

In a first exemplary embodiment shown in FIG. 117, the actuator 28 includes first and second sets of openings 102 in the barrel with the first set of openings near the nose. Openings are also illustrated in the actuator 28 of FIGS. 106-107. The rear portion of the actuator 28 of FIG. 117 also includes a set of legs 104 extending from the barrel and connected to a ring 106. The features described in this embodiment can be used in combination with the features described throughout this application.

Figure 119:
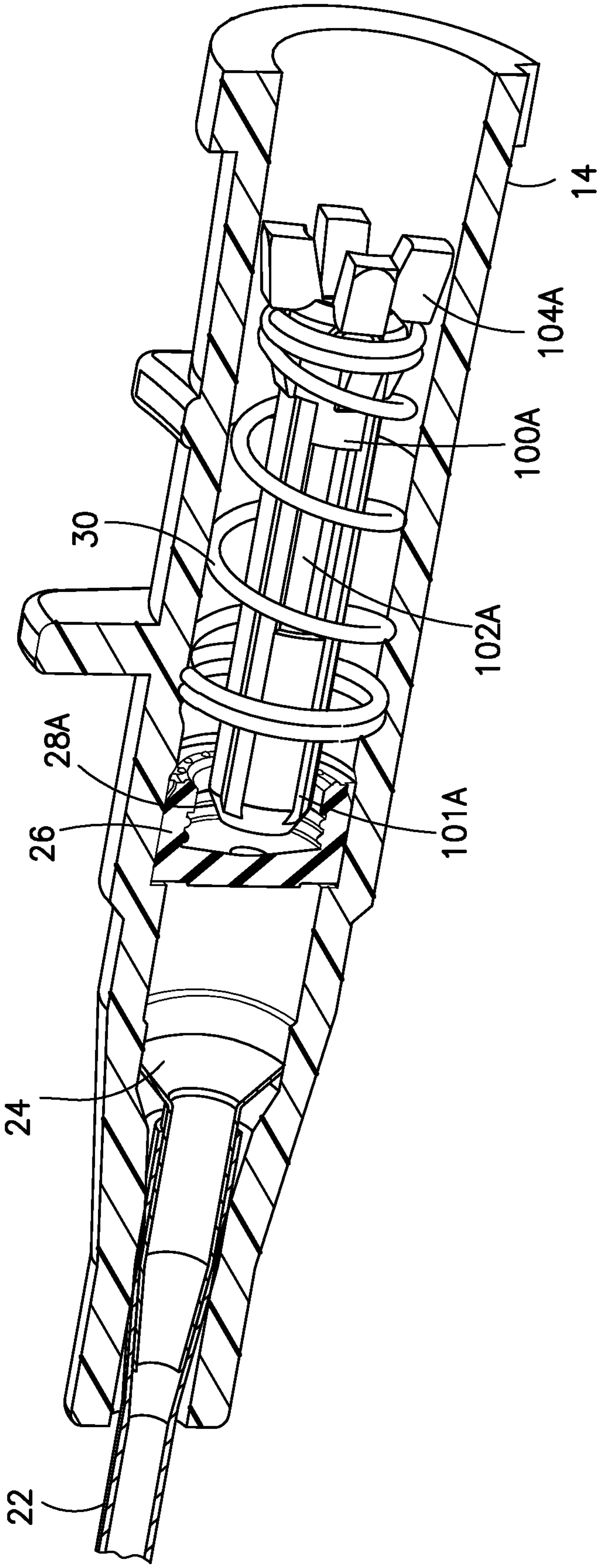
Figure 120:
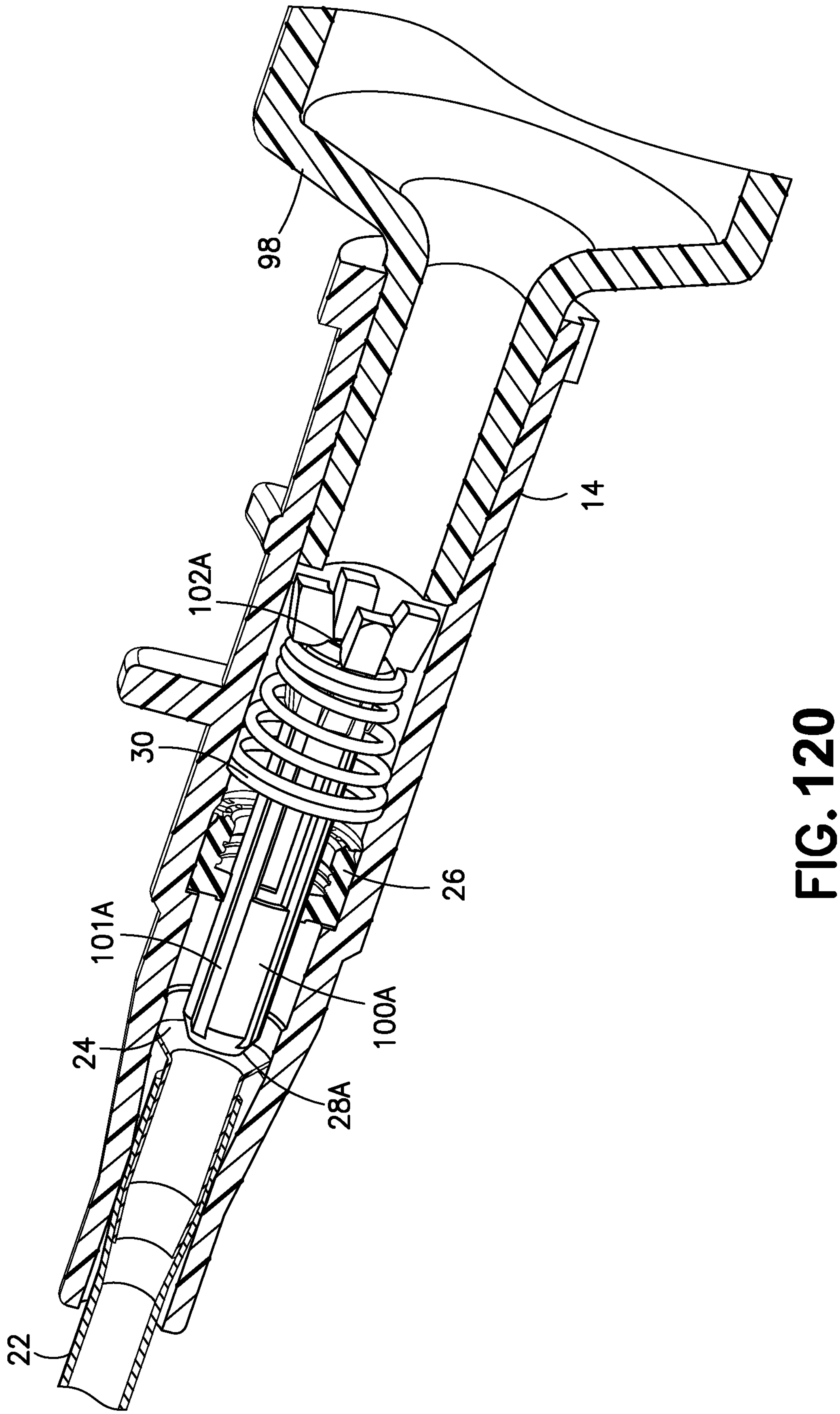
Figure 121:
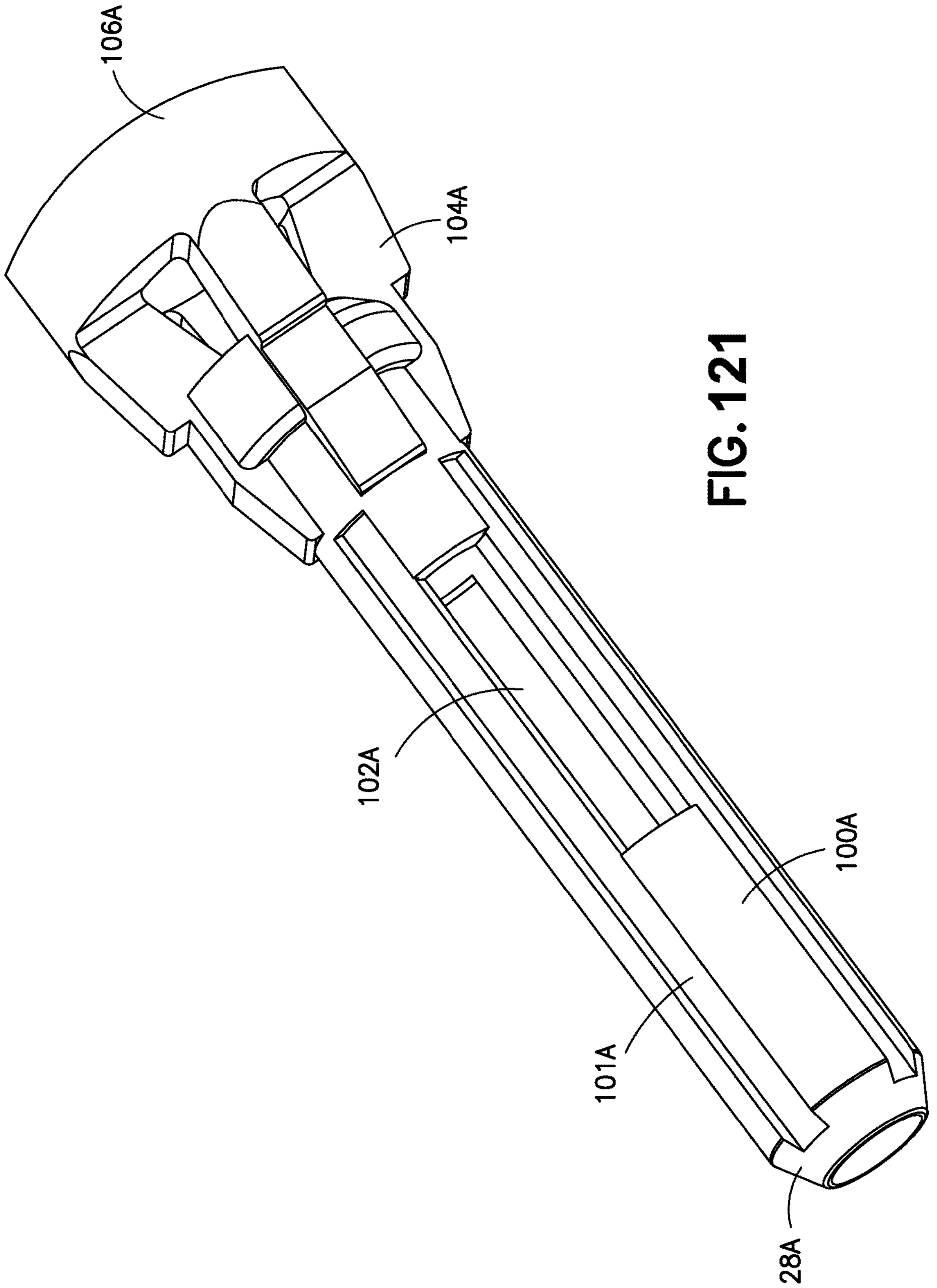
Figure 122:
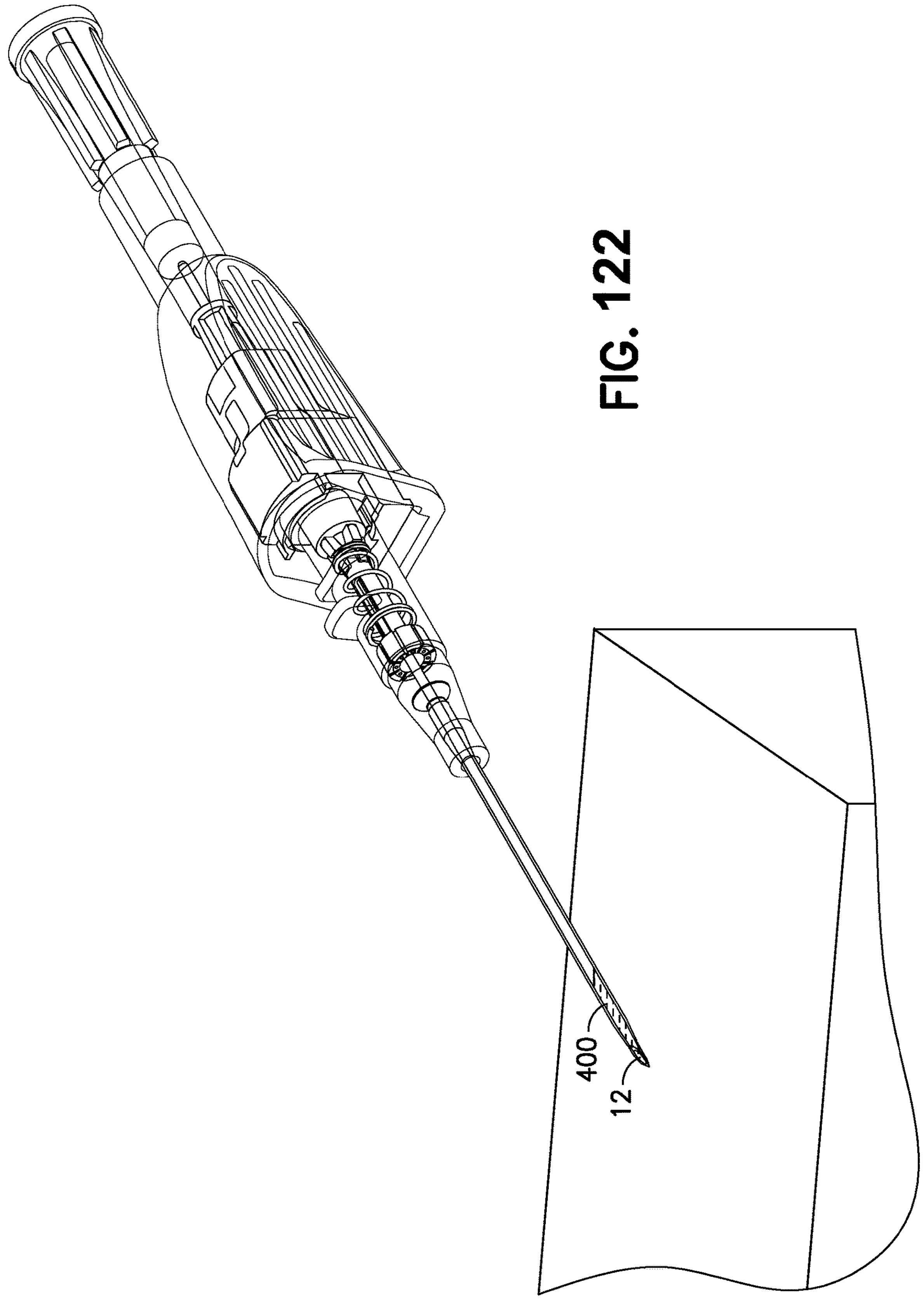
Figure 123:
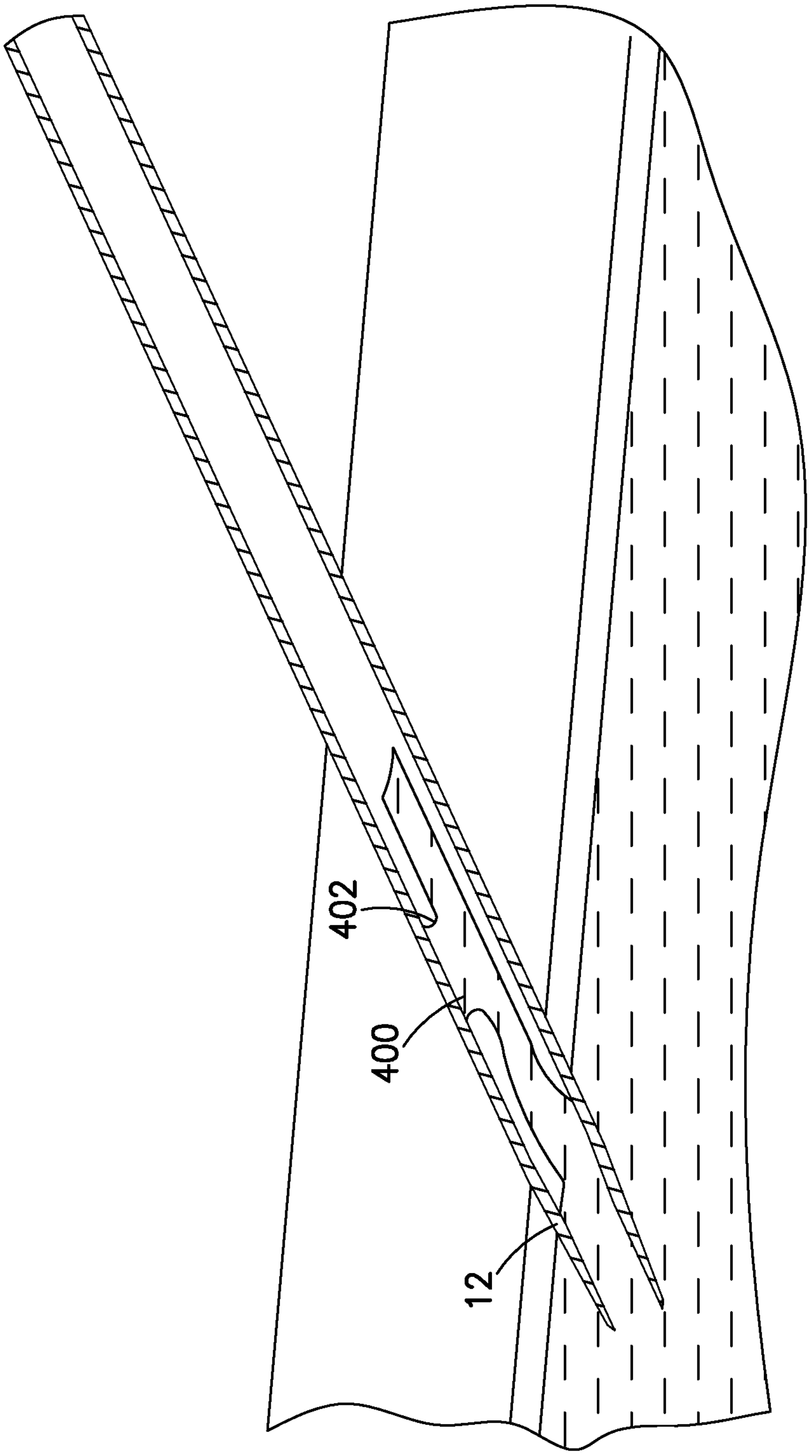
Figure 124:
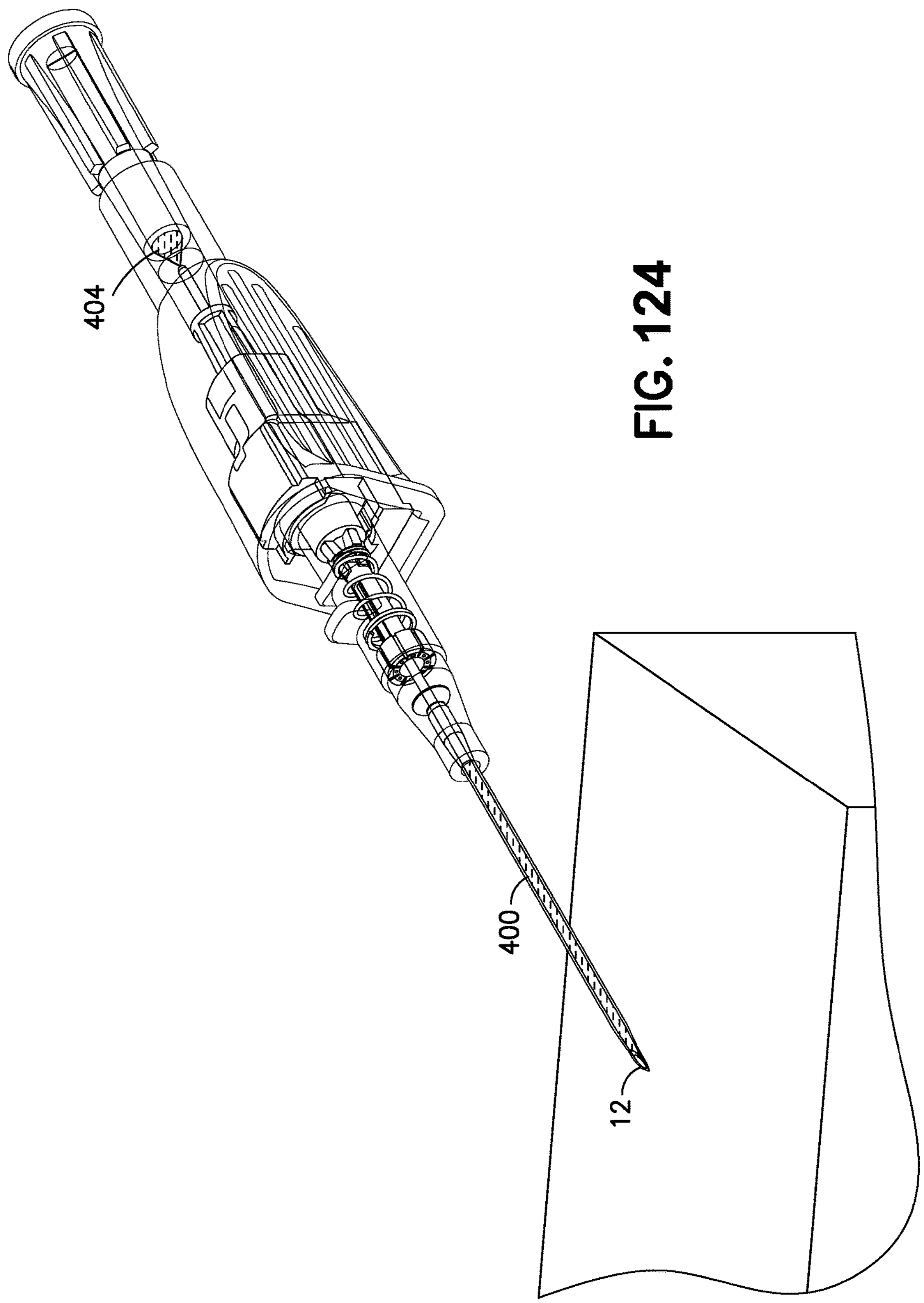
Figure 125:
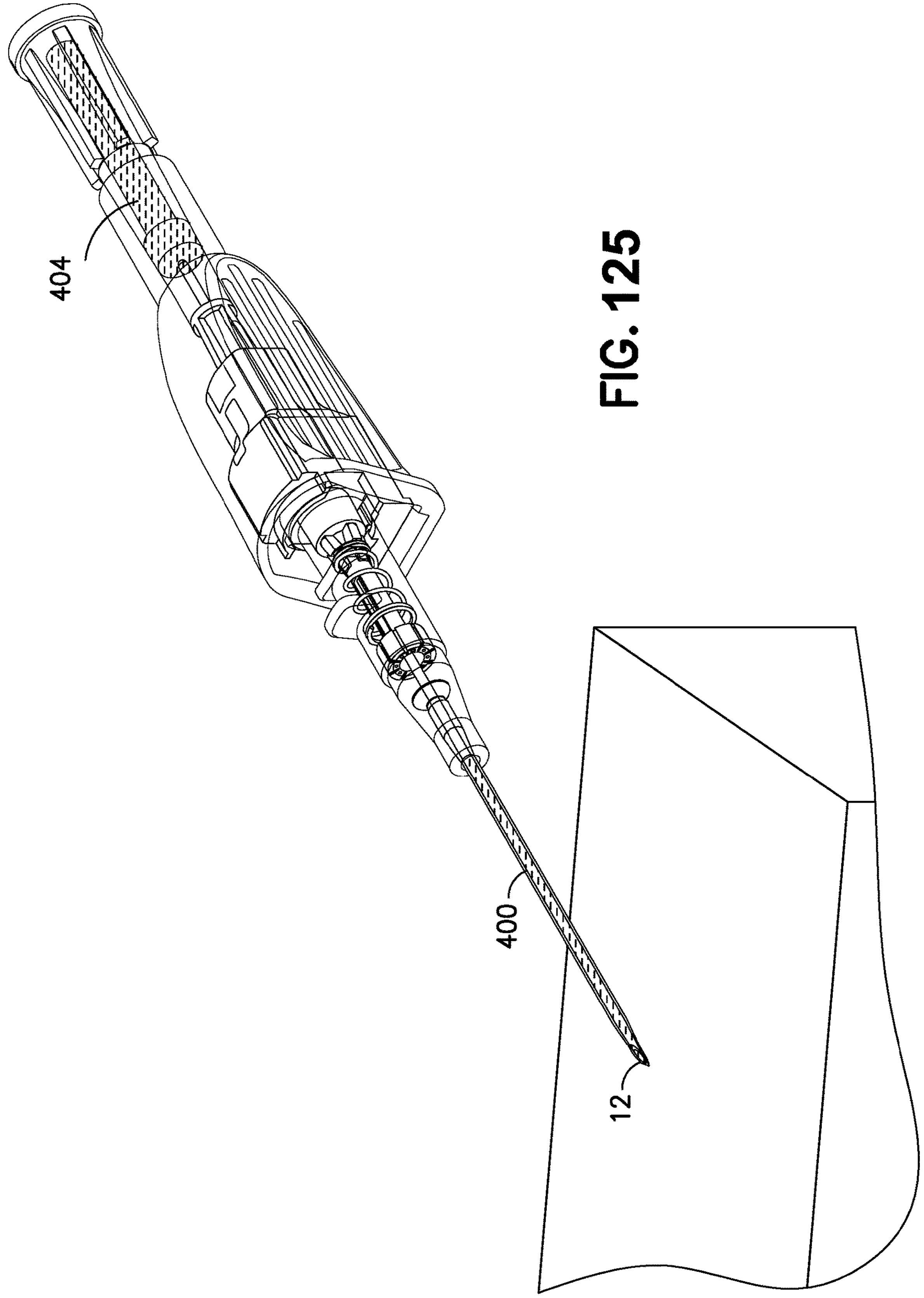
Figure 126:
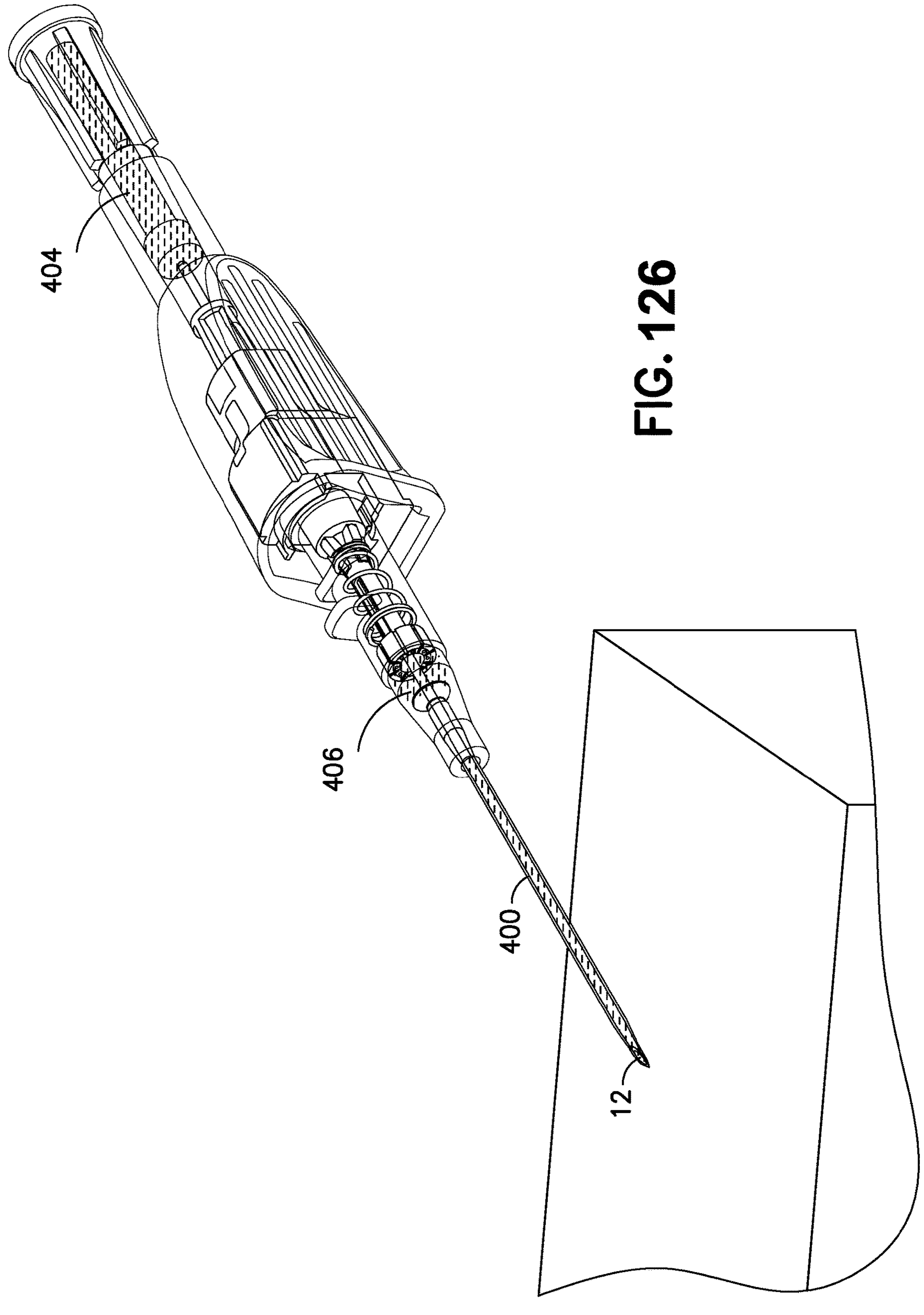

In a second exemplary embodiment shown in FIGS. 119-121, the actuator 28A includes a set of grooves 101A and a set of openings 102A. The grooves 101A extend from the nose toward the back of the actuator barrel 100A. The openings 102A are positioned towards the rear of the barrel 100A. When the actuator 28A extends through the septum 26, the grooves 101A channel fluid to the openings 102A which remain on the proximal side of the septum 26. The grooves 101A may be positioned on the side of the openings 102A or directly in line with the openings 102A. The rear portion of the actuator includes a set of legs 104A extending from the barrel. As illustrated in FIG. 121, a ring 106A may be connected to the legs 104A to engage a Luer connector 98 or the Luer connector 98 may directly engage the legs 104A as illustrated in FIGS. 119 and 120. The features described in this embodiment can be used in combination with the features described throughout this application.

In an exemplary embodiment, the biasing member 30 is a spring, for example a helical compression spring with a distal end and a proximal end. The spring may be made from metal, plastic, an elastomer, or another suitable resilient material. The distal end of the spring forms an interference fit with the inner surface of the catheter hub 14. The interference fit may be sufficient to retain the spring, even during loading. The proximal end of the spring connects to the actuator 28. The features described in this embodiment can be used in combination with the features described throughout this application.

FIGS. 122-126 depict various exemplary blood flashback features of the catheter assembly. Flashback is the visibility of blood that confirms the entry of the needle tip into the vein. Primary flashback 400 is seen through the catheter tubing as blood travels into the open distal end of the hollow needle 12, out a notch or opening 402 (also visible in FIG. 13) in the needle 12 near the needle tip, and up through the internal annular space between the needle 12 and the inside of the catheter tubing 22. The secondary flashback 404 is seen in the needle hub/grip 16 when it comes out of the back of the needle 12 and enters a flash chamber in the needle hub/grip. Air is vented by the plug in the back of the needle hub/grip 16 by a porous membrane or micro grooves. Tertiary flashback 406 is in the catheter hub 14 when the blood from the primary flashback 400 flows into it and stops at the blood control septum 26. Air is vented by micro grooves in the periphery of the blood control septum 26. The features described in this embodiment can be used in combination with the features described throughout this application.

Figure 127:
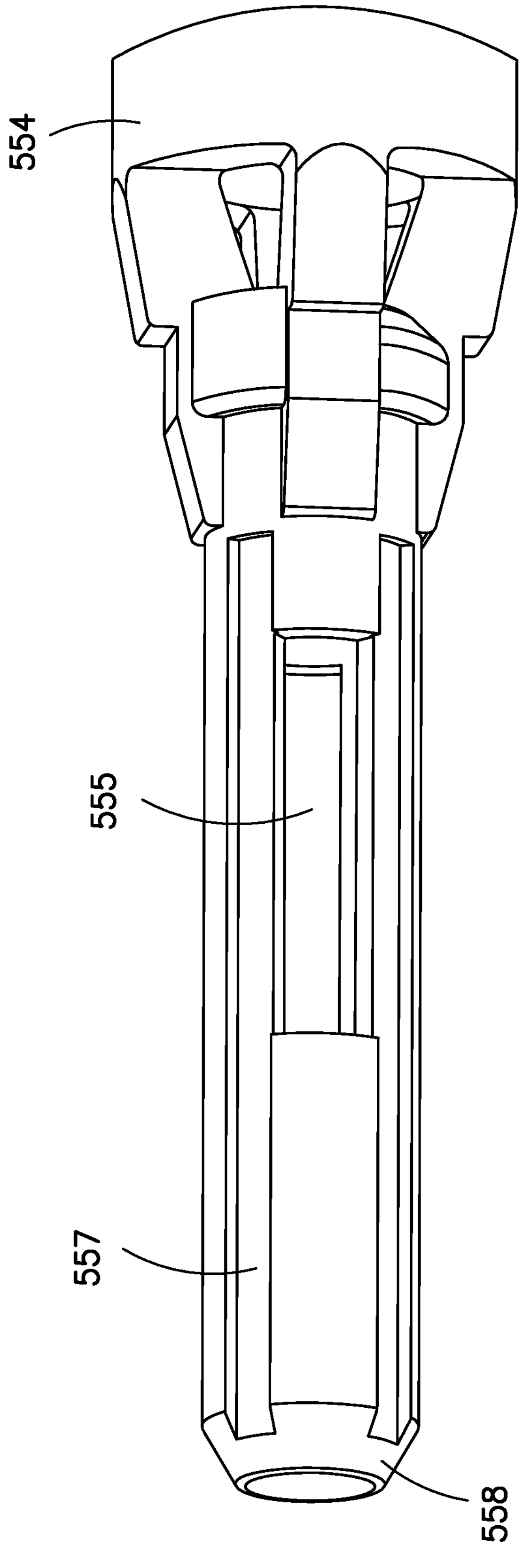

FIG. 127 illustrates the actuator of FIG. 121 in further detail. The actuator 554 can be used in the catheter assemblies illustrated in FIG. 117-120. The actuator 554 includes a nose 558 that reduces friction when the actuator 554 penetrates into a septum 538 of a catheter hub assembly. The actuator 554 further includes openings 555 that extend through the actuator 554 in a direction perpendicular to a centerline of the actuator 554. For example, the actuator 554 can include two rectangular shaped openings 555, although more or less are contemplated.

The actuator 554 also includes a plurality of grooves 557 that extend axially along the distal portion of an outer surface of the actuator 554 in a plane parallel to the centerline of the actuator 554. For example, four grooves 557, substantially radially equidistant from each other, can be present along an external surface of the distal portion of the actuator 554, although more or less grooves 557 are contemplated. The grooves 557 can be of varying depths into the actuator 554. The grooves 557 are different from the openings 555 because the grooves 557 do not extend through the actuator 554.

The openings 555 and the grooves 557 advantageously provide increased area for the fluid to move inside the catheter hub assembly. The increased area advantageously allows for fluid flushing and to prevent coagulation of fluid in the proximal and distal ends of the septum. Additionally, the openings 555 and the plurality of grooves 557 advantageously minimize the stagnation of fluid and allow for greater mixing. The grooves 57 further prevent the septum from sealing on an outside surface of the actuator during operation. By not forming a sealing interface, the fluid is permitted to leak through the septum via the grooves 57 and provide additional flushing.

Figure 128:
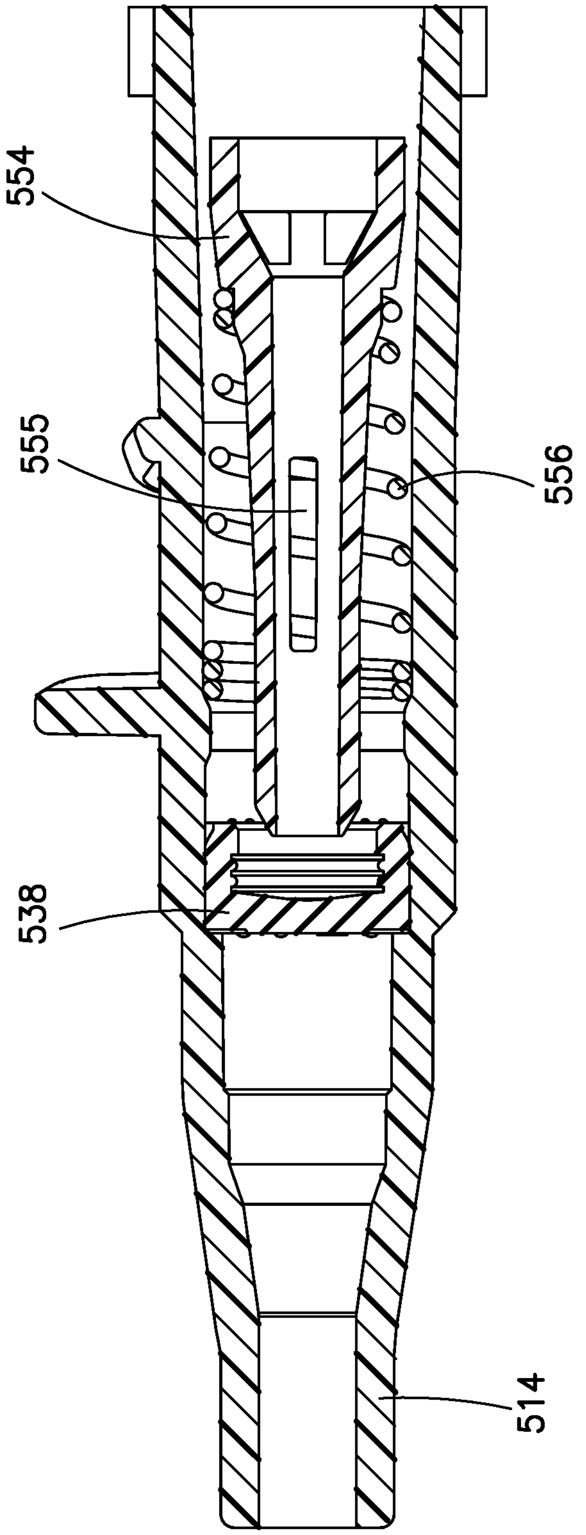

FIG. 128 illustrates the actuator 554 of FIG. 127 in the catheter hub assembly. Similar to the embodiments described above, the catheter hub assembly further includes a catheter hub 514, a septum 538 and a biasing member 556. As illustrated, the openings 555 and the grooves 557 of the actuator 554 provide more area for fluid flow inside the catheter hub 514, thus achieving the advantages described above.

Figure 129:
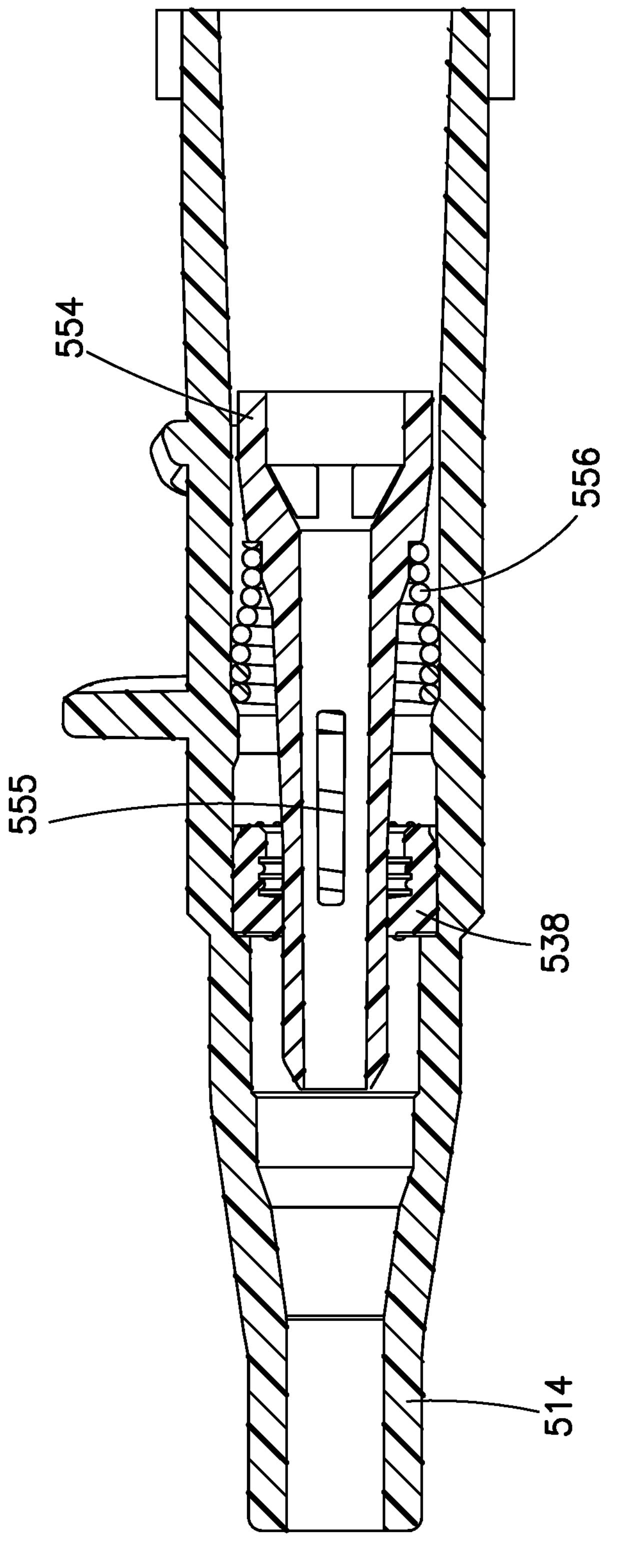
Figure 130:
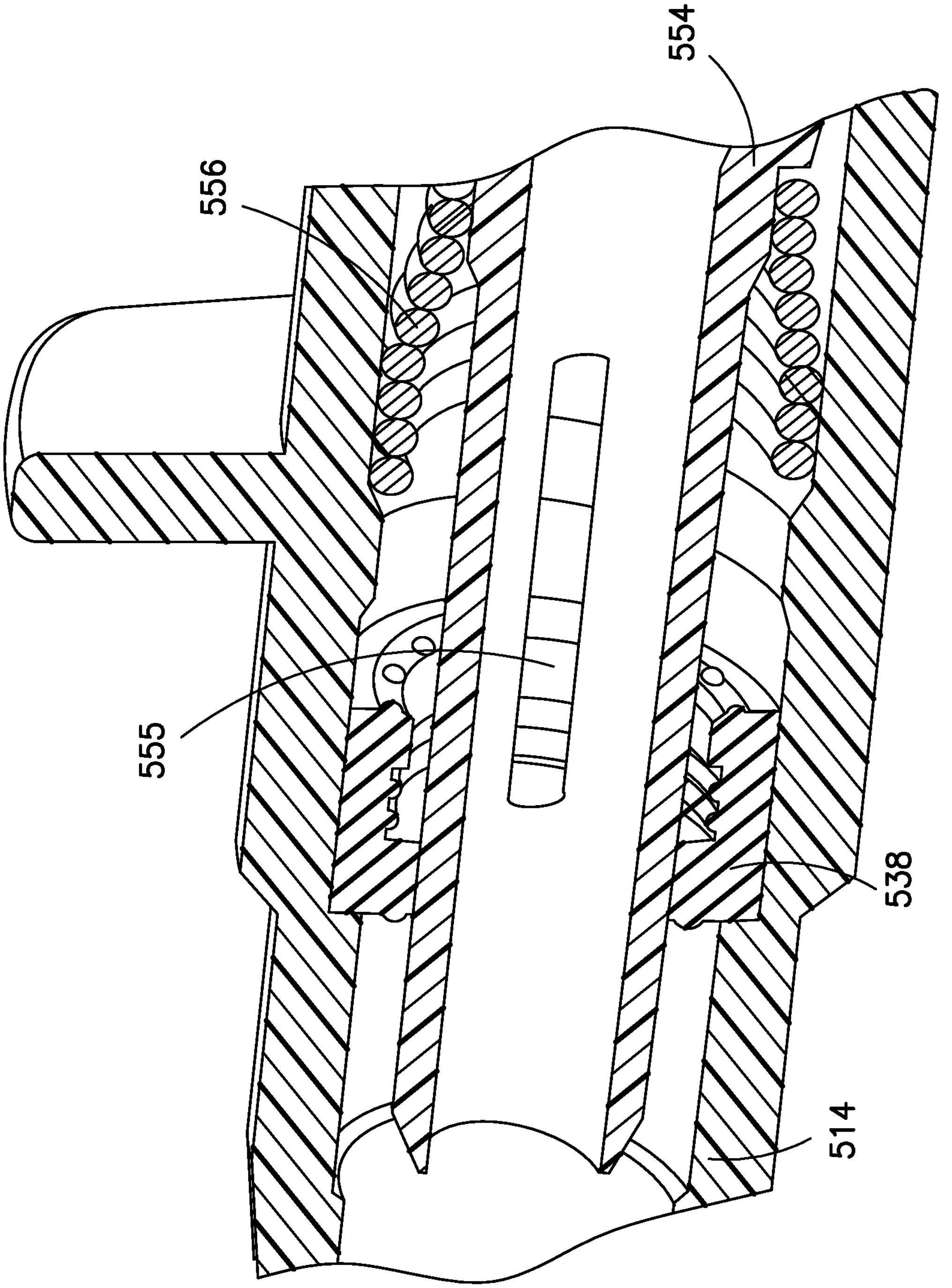

FIGS. 129 and 130 illustrate the catheter hub assembly when the biasing member 556 is compressed and the actuator 554 penetrates the septum 538. The catheter hub assembly may be configured such that the openings 555 and/or the grooves 557 of the actuator 554 optionally penetrates the septum 538. In this embodiment, the openings 555 in the actuator 554 do not penetrate the septum 538. However, the grooves 557 in the actuator 554 penetrate the septum 538. This configuration allows for increased fluid flow from the proximal end to the distal end of the septum 38 through the grooves 557, in addition to the advantages described above. After operation of the catheter assembly is complete, the actuator 554 is retracted from the septum 538 via the force exerted by the biasing member 556. The catheter assembly is configured for multiple uses upon depression of the actuator 554. The features described in this embodiment, including the actuator, can be used in combination with the features described throughout this application.

FIG. 131 illustrates another embodiment of an actuator 664 in a catheter hub assembly. The catheter hub assembly includes a catheter hub 662 having a side port 668. The side port 668 provides secondary access to the fluid flow in the catheter hub 662. The intersection of the main bore of the catheter hub 662 and the side port 668 includes a sleeve 672. The sleeve 672 provides selective fluid communication between the side port 668 and the catheter hub 662. Specifically, when sufficient fluid pressure is applied through the side port 168, the sleeve 672 compresses. The compression of the sleeve 672 allows for fluid to enter the catheter hub 662. The catheter hub assembly further includes a septum 670 and a biasing member 666 that provides tension to the actuator 664.

The actuator 664 includes a plurality of openings 665 that extend through the actuator 664 in a similar manner as described above. The actuator 664 includes two rows of four openings 665 having different sizes and similar spacing, although various quantities, sizes and spacing of the openings 665 are contemplated. As illustrated, the openings 665 provide more area for fluid flow inside the catheter hub 662, thus achieving similar advantages described above with respect to FIGS. 127-130.

FIGS. 132 and 133 illustrate the catheter hub assembly when the actuator 664 penetrates the septum 670 and compresses the biasing member 666. The catheter hub assembly is configured such that the openings 665 of the actuator 664 optionally penetrate the septum 670. In this embodiment, the openings 665 in the actuator 664 do not penetrate the septum 670. This configuration allows for increased fluid flow between the side port 668 and the catheter hub 662 at the proximal end of the septum 670, in addition to the advantages described above. If the openings 665 in the actuator 664 penetrate the septum 670, increased mixing of fluid would also take place at a distal end of the septum 670.

When operation of the catheter assembly is complete, the actuator 664 is retracted from the septum 670 via the force exerted by the biasing member 666. The catheter assembly is configured for multiple uses upon depression of the actuator 664. The features described in this embodiment, such as the actuator, can be used in combination with the features described throughout this application.

In another exemplary embodiment, the collar of the catheter hub as described above can be replaced by any other structure that defines a notch. For example, the collar may be a groove or a recess in the catheter hub. Accordingly, the groove in the catheter hub can be used to engage and disengage a clip in a similar manner as described above. The features described in this embodiment can be used in combination with the features described throughout this application.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the exemplary embodiments disclosed. Any of the embodiments and/or elements disclosed herein may be combined with one another to form various additional embodiments not specifically disclosed. Accordingly, additional embodiments are possible and are intended to be encompassed within this specification and the scope of the appended claims. The specification describes specific examples to accomplish a more general goal that may be accomplished in another way.

As used in this application, the terms “front,” “rear,” “upper,” “lower,” “upwardly,” “downwardly,” and other orientational descriptors are intended to facilitate the description of the exemplary embodiments of the present invention, and are not intended to limit the structure of the exemplary embodiments of the present invention to any particular position or orientation. Terms of degree, such as “substantially” or “approximately” are understood by those of ordinary skill to refer to reasonable ranges outside of the given value, for example, general tolerances associated with manufacturing, assembly, and use of the described embodiments.

The invention claimed is:

1. A catheter assembly comprising:

a catheter;

a needle disposed in the catheter and having a distal tip;

a catheter hub attached to the catheter and enclosing the needle;

a needle shield configured to be connected to the catheter hub, the needle shield having a mounting protrusion including a projection extending from an inner surface of the needle shield, the mounting protrusion is integrated into the needle shield to form a unitary and monolithic structure;

a clip including a first leg defining a first plane, a second leg defining a second plane forming a first space between the first plane and the second plane, and a periphery of a mounting cavity, the clip being disposed in the needle shield;

wherein the clip has a first position that exposes the distal tip of the needle, the needle biases the clip in the first position, the clip includes a second position that shields the distal tip of the needle within the clip; and when the needle retracts, the clip transitions into the second position and while the clip substantially maintains an axial position, the needle unbiases the clip, causing the clip to deflect and shield the distal tip of the needle and causing the periphery of the mounting cavity to move into engagement with the mounting protrusion to secure the clip to the needle shield and avoid undesired movement or tampering of the clip, the periphery of the mounting cavity surrounds the mounting protrusion to engage the mounting protrusion, the periphery of the mounting cavity defining a second space outside of the first space;

wherein the periphery of the mounting cavity does not engage the mounting protrusion in the first position whereby the periphery of the mounting cavity does not surround the mounting protrusion;

wherein the needle compresses the second leg toward the first leg in the first position.

2. The catheter assembly of claim 1, wherein the clip is compressed by the needle in the first position.

3. The catheter assembly of claim 1, wherein the clip is not compressed by the needle in the second position.

4. The catheter assembly of claim 1, wherein the needle shield includes a housing slot that is configured to receive barbs of the clip to secure the clip to the needle shield.

5. The catheter assembly of claim 1, wherein the clip includes a ledge disposed on a bottom surface of the needle shield.

6. The catheter assembly of claim 5, wherein an outer surface of the ledge faces an outside of the catheter assembly.

7. The catheter assembly of claim 1, wherein the clip includes a flag disposed in one of the first and second legs, the periphery of the mounting cavity disposed in an other of the one of the first and second legs.

8. The catheter assembly of claim 7, wherein the first leg and the second leg are angled in a V shape and connected together by a radius, the needle extends between the first plane and the second plane when the clip is in the second position.

9. The catheter assembly of claim 1, wherein when the needle moves to the second position, the clip is unbiased to move the periphery of the mounting cavity to engage the mounting protrusion.

10. The catheter assembly of claim 1, wherein the periphery of the mounting cavity is interlocked to the needle shield to prevent relative movement in the second position.

11. The catheter assembly of claim 1, wherein the second leg includes the periphery of the mounting cavity.

12. The catheter assembly of claim 11, wherein the first leg includes a flag blocking the distal tip of the needle from exiting the needle shield in the second position.

13. A catheter assembly comprising:

a catheter;

a needle disposed in the catheter and having a distal tip;

a catheter hub attached to the catheter and enclosing the needle;

a needle shield configured to be connected to the catheter hub, the needle shield having a mounting protrusion including a projection extending from an inner surface of the needle shield, the mounting protrusion is integrated into the needle shield to form a unitary and monolithic structure;

a clip including a first leg including a flag, a second leg including a periphery of a mounting cavity, the clip being disposed in the needle shield; wherein the clip has a first position that exposes the distal tip of the needle, the needle biases the clip in the first position, the clip includes a second position that shields the distal tip of the needle within the clip; and when the needle retracts, the clip transitions into the second position and while the clip substantially maintains an axial position, the needle unbiases the clip, causing the clip to deflect and shield the distal tip of the needle and causing a periphery of the mounting cavity to surround the mounting protrusion to secure the clip to the needle shield and avoid undesired movement or tampering of the clip; wherein the periphery of the mounting cavity surrounds the mounting protrusion in the second position but not in the first position; and the flag blocks the distal tip of the needle in the second position; wherein the second leg moves away from the first leg when the clip moves from the first position to the second position.

* * * * *